US005494889A

United States Patent [19]

Brunner et al.

[11] Patent Number: 5,494,889

[45] Date of Patent: Feb. 27, 1996

[54] HERBICIDES

[75] Inventors: Hans-Georg Brunner, Lausen; Hans Moser, Magden, both of Switzerland; Georg Pissiotas, Lörrach, Germany

[73] Assignee: Ciba-Geigy Corporation, Tarrytown, N.Y.

[21] Appl. No.: 157,052

[22] PCT Filed: May 18, 1992

[86] PCT No.: PCT/EP92/01092

§ 371 Date: Dec. 2, 1993

§ 102(e) Date: Dec. 2, 1993

[87] PCT Pub. No.: WO92/21684

PCT Pub. Date: Dec. 10, 1992

[30] Foreign Application Priority Data

| | | | |
|---|---|---|---|
| Jun. 6, 1991 | [CH] | Switzerland | 1682/91 |
| Mar. 2, 1992 | [CH] | Switzerland | 642/92 |

[51] Int. Cl.[6] .......... C07D 513/04; A01N 43/90

[52] U.S. Cl. .......... 504/263; 544/105; 548/126

[58] Field of Search .......... 548/126; 504/263

[56] References Cited

U.S. PATENT DOCUMENTS

| | | | |
|---|---|---|---|
| 4,249,934 | 2/1981 | Wakabayashi et al. | 71/92 |
| 4,684,397 | 8/1987 | Nagano et al. | 71/96 |
| 4,801,408 | 1/1989 | Nagano et al. | 260/508 |
| 4,885,023 | 12/1989 | Yamaguchi et al. | 71/90 |

FOREIGN PATENT DOCUMENTS

| | | | |
|---|---|---|---|
| 614775 | 10/1988 | Australia . | |
| 238711 | 9/1987 | European Pat. Off. . | |
| 304920 | 3/1989 | European Pat. Off. . | |
| 311135 | 4/1989 | European Pat. Off. . | |
| 373461 | 6/1990 | European Pat. Off. . | |
| 409025 | 1/1991 | European Pat. Off. . | |
| 2526358 | 1/1976 | Germany . | |
| 3724098 | 2/1989 | Germany . | |
| 5213970 | 8/1993 | Japan | 548/126 |

OTHER PUBLICATIONS

Chem. Abst. vol. 114, 228728h (1991).

Chem. Abst. vol. 111, 174127x (1989).

Chem Abst. vol. 111, 7416j (1989).

A. Klemann et al, Pharmazie vol. 46, (1991) (8) 573–575.

O. Morgenstern et al., Pharmazie vol. 46 (1991) (6) 418–422.

J. Amer. Chem. Soc. 88, 3959–3963 (1966) Robert Crawford et al.

J. Org. Chem. 46, 442–446 (1981) C. G. Overberger et al.

*Primary Examiner*—Robert Gerstl

*Attorney, Agent, or Firm*—Marla J. Mathias; William A. Teoli, Jr.

[57] ABSTRACT

Thiadiazabicyclooctanes and thiadiazabicyclooctenes of formula I

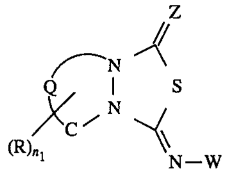

(I)

wherein the substituents are as defined herein, having good pre- and post-emergence selective herbicidal properties.

27 Claims, No Drawings

HERBICIDES

The present invention relates to novel herbicidally active thiadiazabicyclooctanes and thiadiazabicyclooctenes, to processes for the preparation thereof, to compositions comprising them as active ingredients, and to the use thereof for controlling weeds, especially selectively in crops of useful plants.

Thiadiazabicyclo derivatives having herbicidal activity are generally known. Such compounds are disclosed, for example, in European Patent Applications EP-A-0 238 711 and EP-A-0 304 920 as well as in U.S. Pat. Nos. 4,885,023, 4,684,397 and 4,801,408.

Novel thiadiazabicyclooctanes and thiadiazabicyclooctenes having herbicidal activity have now been found.

The thiadiazabicyclooctanes and thiadiazabicyclooctenes according to the invention correspond to formula I

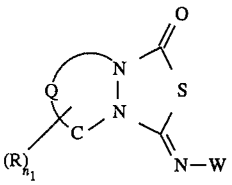

(I)

wherein

Z is oxygen or sulfur;

Q is —C—C— or C═C—;

R is $C_1$–$C_6$alkyl, $C_3$–$C_6$cycloalkyl, $C_1$–$C_6$haloalkyl, $C_3$–$C_6$alkenyl, $C_3$–$C_6$alkynyl, $C_3$–$C_6$haloalkenyl, $C_3$–$C_6$haloalkynyl, phenyl, benzyl, phenyl substituted by $C_1$–$C_4$alkyl, $C_1$–$C_4$alkoxy, $C_1$–$C_4$haloalkyl or by halogen, benzyl substituted by $C_1$–$C_4$alkyl, $C_1$–$C_4$alkoxy, $C_1$–$C_4$haloalkyl or by halogen, it being possible for the unsubstituted and substituted phenyl and benzyl groups to occur in each case only once;

W is

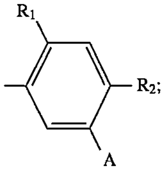

($W_1$)

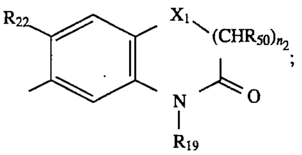

($W_2$)

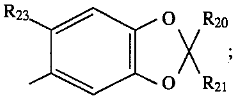

($W_3$)

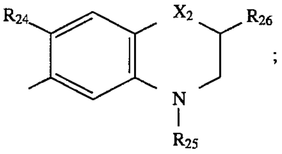

($W_4$)

-continued

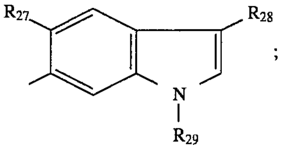

($W_5$)

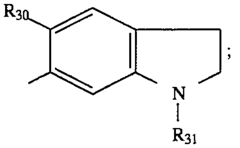

($W_6$)

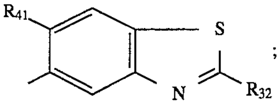

($W_7$)

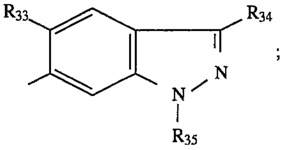

($W_8$)

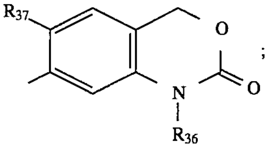

($W_9$)

or

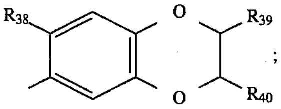

($W_{10}$)

$R_1$, $R_{22}$, $R_{23}$, $R_{24}$, $R_{27}$, $R_{30}$, $R_{33}$, $R_{37}$, $R_{38}$ and $R_{41}$ are each independently of the others hydrogen or halogen;

$R_2$ is hydrogen, cyano, nitro, halogen, $C_1$–$C_4$alkyl, $C_1$–$C_4$haloalkoxy or $C_1$–$C_4$haloalkyl;

A is hydrogen, cyano, nitro, $COR_3$, $X_3R_4$,

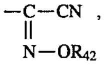 , $—COR_8$, 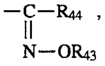 , 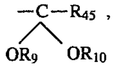 ,

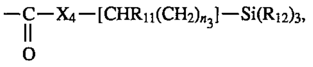

$—N(R_{13})—SO_2—R_{14}$, 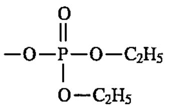 or

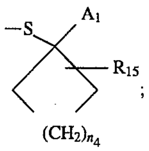

$A_1$ is cyano or $—COR_{16}$;

$R_3$ is halogen, $X_4$-$R_5$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_3$–$C_4$alkenylamino, diallylamino, —N-pyrrolidino, —N-piperidino, —N-morpholino, —N-thiomorpholino, —N-piperidazino, —O—N=C($CH_3$)—$CH_3$, or —O—$CH_2$—$CH_2$—O—N=C($CH_3$)—$CH_3$;

$R_4$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl that is unsubstituted or substituted in the phenyl ring by up to three identical or different substituents from the group halogen, $C_1$–$C_4$alkyl, halo-$C_1$–$C_4$alkyl, halo-$C_1$–$C_4$alkoxy and $C_1$–$C_4$alkoxy; or is furanoyl, thienyl; or $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl, di-$C_1$–$C_4$alkylaminocarbonyl; or phenylaminocarbonyl that is unsubstituted or substituted in the phenyl ring by up to three identical or different substituents from the group halogen, $C_1$–$C_4$alkyl, halo-$C_1$–$C_4$alkyl, halo-$C_1$–$C_4$alkoxy and $C_1$–$C_4$alkoxy or that is monosubstituted by cyano or by nitro, or dioxolan-2-yl that is unsubstituted or substituted by one or two $C_1$–$C_4$alkyl radicals, or dioxan-2-yl that is unsubstituted or substituted by one or two $C_1$–$C_4$alkyl radicals, or is $C_1$–$C_4$alkyl substituted by cyano, nitro, carboxy or by $C_1$–$C_8$alkylthio-$C_1$–$C_8$alkoxycarbonyl;

$R_5$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, halo-$C_3$–$C_8$alkenyl, $C_3$–$C_8$alkynyl, $C_3$–$C_7$cycloalkyl, $C_3$–$C_7$cycloalkyl-$C_1C_4$alkyl, halo-$C_3$–$C_7$cycloalkyl, or benzyl that is unsubstituted or substituted in the phenyl ring by up to three identical or different substituents from the group halogen, $C_1$–$C_4$alkyl, halo-$C_1$–$C_4$alkyl, halo-$C_1$–$C_4$alkoxy and $C_1$–$C_4$alkoxy, or alkali metal ions, alkaline earth metal ions and ammonium ions, or the group —[$CHR_6(CH_2)_{n_5}$]—$COOR_7$;

$R_6$, $R_{20}$, $R_{21}$, $R_{26}$, $R_{28}$, $R_{32}$, $R_{34}$, $R_{39}$, $R_{40}$, $R_{46}$, $R_{47}$, $R_{49}$, $R_{50}$, $R_{51}$ and $R_{52}$ are each independently of the others hydrogen or $C_1$–$C_4$alkyl;

$R_7$ and $R_{48}$ are each independently of the other hydrogen, $C_1$–$C_6$alkyl, $C_3$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

$R_8$, $R_{44}$ and $R_{45}$ are each independently of the others hydrogen, $C_1$–$C_4$alkyl, halo-$C_1$–$C_4$alkyl or $C_1$–$C_4$alkoxy-$C_1$–$C_4$alkyl;

$R_9$ and $R_{10}$ are each independently of the other $C_1$–$C_4$alkyl, $C_2$–$C_4$haloalkyl or $C_2$–$C_8$alkoxyalkyl, or $R_9$ and $R_{10}$ together are an ethano, propano or a cyclohexane-1,2-diyl bridge, those groups being either unsubstituted or substituted by one or two radicals from the group $C_1$–$C_4$alkyl, $C_1$–$C_4$haloalkyl and $C_1$–$C_4$hydroxyalkyl;

$R_{11}$ is hydrogen, $C_1$–$C_5$alkyl or $C_3$–$C_7$alkenyl;

the radicals $R_{12}$ are each independently of the others hydrogen or $C_1$–$C_8$alkyl;

$R_{13}$ is hydrogen, $C_1$–$C_5$alkyl, benzyl, halo-$C_1$–$C_4$alkyl, $C_3$–$C_8$alkenyl or $C_3$–$C_8$alkynyl;

$R_{14}$ is $C_1$–$C_6$alkyl, halo-$C_1$–$C_5$alkyl or di-$C_1$–$C_4$alkylamino;

$R_{15}$ is hydrogen, fluorine, chlorine, bromine, $C_1$–$C_4$alkyl or trifluoromethyl;

$R_{16}$ is chlorine, $X_5$-$R_{17}$, amino, $C_1$–$C_4$alkylamino, di-$C_1$–$C_4$alkylamino, $C_2$–$C_4$haloalkylamino, di-$C_2$-$C_4$haloalkylamino, $C_1$–$C_4$alkoxyalkylamino, di-$C_1$–$C_4$alkoxyalkylamino, $C_3$–$C_4$alkenylamino, diallylamino, —N-pyrrolidino, —N-piperidino, —N-morpholino, —N-thiomorpholino, —N-piperidazino, the group —O—N=C—($CH_3$)—$CH_3$, —O—$CH_2$—$CH_2$—O—N=C($CH_3$)—$CH_3$ or the group —N($OR_{46}$)—$R_6$;

$R_{17}$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, halo-$C_3$–$C_8$alkenyl, $C_3$–$C_8$alkynyl, $C_3$–$C_7$cycloalkyl, $C_3$–$C_7$cycloalkyl-$C_1$–$C_4$alkyl, halo-$C_3$–$C_7$cycloalkyl, or benzyl that is unsubstituted or substituted in the phenyl ring by up to three identical or different substituents from the group halogen, $C_1$–$C_4$alkyl, halo-$C_1$–$C_4$alkyl, halo-$C_1$–$C_4$alkoxy and $C_1$–$C_4$alkoxy, or alkali metal ions, alkaline earth metal ions and ammonium ions, the group —[$CHR_{47}$—$(CH_2)_m$]—$COOR_{48}$, or the group [$CHR_{49}$—$(CH_2)_t$—$Si(R_8)_3$];

m is 0, 1, 2, 3 or 4;

t is 0, 1, 2, 3 or 4;

$R_{18}$ is $C_1$–$C_4$alkyl;

$R_{19}$ is hydrogen, $C_1$–$C_6$alkyl, $C_2$–$C_4$alkenyl or $C_2$–$C_6$alkynyl; halo-substituted $C_1$–$C_6$alkyl, $C_2$–$C_4$alkenyl or $C_3$–$C_6$alkynyl; $C_1$–$C_4$alkoxy-$C_1$–$C_4$alkyl, $C_1$–$C_4$alkoxy-$C_1$–$C_2$alkoxy-$C_1$–$C_2$alkyl, 1-phenylpropen-3-yl, cyano- or $C_3$–$C_6$cycloalkyl-substituted $C_1$–$C_6$alkyl; carboxy-$C_1$–$C_4$alkyl, $C_1$–$C_6$alkoxycarbonyl-$C_1$–$C_4$alkyl, halo-$C_1$–$C_6$alkoxycarbonyl-$C_1$–$C_4$alkyl, $C_1$–$C_4$alkoxy-$C_1$–$C_2$alkoxycarbonyl-$C_1$–$C_4$alkyl, $C_1$–$C_6$alkoxycarbonyl-$C_1C_2$alkoxycarbonyl-$C_1$–$C_4$alkyl, $C_3$–$C_6$cycloalkyl-$C_1$–$C_2$alkoxycarbonyl-$C_1$–$C_4$alkyl, $C_1$–$C_5$alkylaminocarbonyl-$C_1$–$C_4$alkyl, di-$C_1$–$C_5$alkylaminocarbonyl-$C_1$–$C_4$alkyl, $C_3$–$C_6$cycloalkyl, $C_1$–$C_4$alkylthio-$C_1$–$C_4$alkyl, benzyl or halo-substituted benzyl, $C_1$–$C_4$alkylsulfonyl, $C_3$–$C_6$alkenyloxy-$C_1$–$C_4$alkyl, $C_1$–$C_8$alkylcarbonyl,

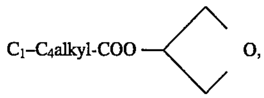
,

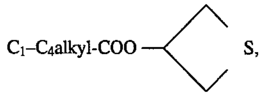
, 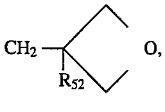
, $C_1$–$C_4$alkylthiocarbonyl-$C_1$–$C_4$alkyl, or the group

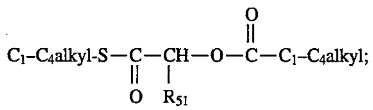
;

$R_{25}$, $R_{29}$, $R_{31}$, $R_{35}$ and $R_{36}$ are each independently of the others hydrogen, $C_1$–$C_4$alkyl, $C_3$–$C_8$alkenyl, halo-$C_3$–$C_8$alkenyl, $C_3$–$C_8$alkynyl, $C_1$–$C_4$alkoxy-$C_1$–$C_8$alkyl, cyano-$C_1$–$C_4$alkyl, $C_1$–$C_8$alkoxycarbonyl-$C_1$–$C_4$alkyl, $C_3$–$C_7$cycloalkyl, $C_3$–$C_7$cycloalkyl-$C_1$–$C_4$alkyl, benzyl, —N-morpholino-, —N-thiomorpholino- or —N-piperidazino-substituted $C_1$–$C_4$alkyl, di-$C_1$–$C_4$alkylamino-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_1$–$C_4$alkoxycarbonyl or $C_1$–$C_4$alkylcarbonyl;

$X_1$, $X_2$, $X_3$, $X_4$ and $X_5$ are each independently of the others oxygen or sulfur; and $n_1$, $n_2$, $n_3$, $n_4$ and $n_5$ are each independently of the others 0, 1, 2, 3 or 4; including the salts and complexes with acids, bases or complexing agents, as well as the stereoisomeric compounds.

In the definitions used in this description, the genetic terms indicated, as well as the individual meanings of the substituents obtainable by combining individual subsidiary terms, include, for example, the following individual substituents, but this list does not constitute a limitation of the invention.

In the above definitions, halogen is to be understood as being fluorine, chlorine, bromine and iodine, preferably fluorine, chlorine and bromine.

Alkyl is methyl, ethyl, isopropyl, n-propyl, n-butyl, isobutyl, sec-butyl, tert-butyl as well as the various isomeric pentyl, hexyl, heptyl, octyl, nonyl and decyl radicals.

Examples of haloalkyl radicals are fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl, trifluoromethyl and dichlorofluoromethyl.

Alkoxy is, for example, methoxy, ethoxy, propoxy, isopropoxy, n-butoxy, isobutoxy, sec-butoxy and tert-butoxy; preferably methoxy and ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, 2-chloroethoxy and trifluoromethoxy.

Alkylthio is, for example, methylthio, ethylthio, propylthio, isopropylthio, n-butylthio, isobutylthio, sec-butylthio, tert-butylthio or the isomers of pentylthio; preferably methylthio and ethylthio.

Alkenyl is to be understood as being straight-chained or branched alkenyl, for example vinyl, allyl, methallyl, 1-methylvinyl, but-2-en-1-yl, pentenyl, 2-hexenyl or 3-heptenyl. Alkenyl radicals having a chain length of 2 or 3 carbon atoms are preferred.

The alkynyl radicals that occur in the definitions of the substituents may be straight-chained or branched, for example ethynyl, propargyl, 3-butynyl, 1-methylpropargyl, 1-pentynyl or 2-hexynyl. Ethynyl and propargyl are preferred.

Cycloalkyl is, for example, cyclopropyl, dimethylcyclopropyl, cyclobutyl, cyclopentyl, methylcyclopentyl, cyclohexyl or cycloheptyl, but is preferably cyclopropyl, cyclopentyl or cyclohexyl.

Alkoxycarbonyl is, for example: methoxycarbonyl, ethoxycarbonyl, n-propoxycarbonyl, isopropoxycarbonyl and n-butoxycarbonyl, preferably methoxycarbonyl and ethoxycarbonyl.

Alkoxyalkyl is, for example: methoxymethyl, ethoxymethyl, propoxymethyl, methoxyethyl, ethoxyethyl, propoxyethyl, methoxypropyl; ethoxypropyl or propoxypropyl.

Alkylthioalkyl is, for example: methylthiomethyl, ethylthiomethyl, methylthioethyl, ethylthioethyl or isopropylthioethyl.

Alkylaminoalkyl is, for example: methylaminoethyl, dimethylaminoethyl, ethylaminoethyl or diethylaminoethyl.

Cyanoalkyl is, for example: cyanomethyl, cyanoethyl or cyanopropyl.

Halocycloalkyl is, for example: 2,2-dichlorocyclopropyl or pentachlorocyclohexyl.

Alkylsulfonyl is, for example: methylsulfonyl, ethylsulfonyl, propylsulfonyl or butylsulfonyl. Methylsulfonyl and ethylsulfonyl are preferred.

Phenyl, also as part of a substituent such as phenoxy, phenylthio, phenoxycarbonyl, phenylaminocarbonyl, benzyl or benzoyl, may generally be unsubstituted or substituted by other substituents. In that case the substituents may be in the ortho-, meta- and/or para-position. Preferred positions for the substituents are the ortho- and para-positions with respect to the ring linkage site. Preferred substituents are halogen atoms.

In the further substituents, which are composed of several elements, the subsidiary elements have the meanings indicated by means of examples above. In these cases too, the lists do not constitute a limitation of the invention, but are given by way of illustration. Of the compounds of formula I, preference is given to those wherein Q is the group —C—C—.

Mention is also to be made of compounds of formula I wherein Z is oxygen.

In a further preferred group of compounds of formula I is $R_{19}$ hydrogen, $C_1$–$C_4$alkyl, $C_3$–$C_8$alkenyl, halo-$C_3$–$C_8$alkenyl, $C_3$–$C_8$alkynyl, $C_1$–$C_4$alkoxy-$C_1$–$C_8$alkyl, cyano-$C_1$–$C_4$alkyl, $C_1$–$C_8$alkoxycarbonyl-$C_1$–$C_4$alkyl, $C_3$–$C_7$cycloalkyl, $C_3$–$C_7$cycloalkyl-$C_1$–$C_4$alkyl, benzyl, —N-morpholino-, —N-thiomorpholino- or —N-piperidazino-substituted $C_1$–$C_4$alkyl. di-$C_1$–$C_4$alkylamino-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_1$–$C_4$alkoxycarbonyl or $C_1$–$C_4$alkylcarbonyl.

Special preference is given to those compounds of formula I wherein $n_1$ is 0 or 1.

In the compounds of formula I, W is preferably $W_1$. Of this group of compounds, special preference is given to those wherein A is $X_3R_4$, $—COR_8$, $—COR_3$,

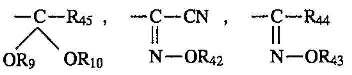

or $—N(R_{13})—SO_2—R_{14}$, wherein $X_3$ is especially sulfur and $R_4$ is $C_1$–$C_6$alkoxycarbonyl-substituted $C_1$–$C_4$alkyl.

In very especially preferred compounds of formula I, $R_1$ and $R_2$ are halogen, especially fluorine in the case of $R_1$ and chlorine in the case of $R_2$.

In another especially prominent group of compounds of formula I, R is hydrogen, $C_1$–$C_6$alkyl or $C_1$–$C_6$haloalkyl, but is preferably hydrogen, methyl or trifluoromethyl.

There may be mentioned as an individual compound within the scope of formula I: 8-(4-chloro-2-fluoro-5-methoxycarbonylmethylthiophenylimino)-7-thia-1,5-diazabicyclo[3.3.0]octan-6-one.

The compounds of formula Ia

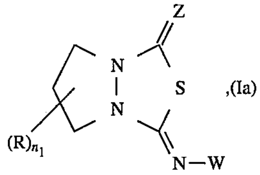

,(Ia)

wherein R, $n_1$, W and Z are as defined under formula I and Q is the group —C—C—, are prepared by converting an isothiocyanate of formula II

S=C=N—W (II), wherein W is as defined under formula I, by means of a compound of formula IIIa (IIIa)

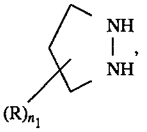

wherein R and $n_1$ are as defined under formula I, into the compound of formula IVa (IVa)

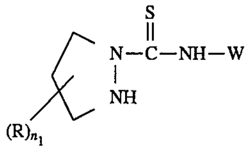

and then reacting the latter with a compound of formula V $CZCl_2$ (V), wherein Z is oxygen or sulfur, in the presence of a base.

The compounds of formula Ib (Ib)

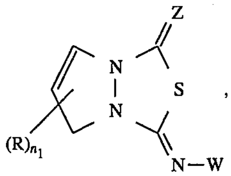

wherein R, $n_1$, W and Z are as defined under formula I and Q is the group —C=C—, are prepared by convening an isothiocyanate of formula II

S=C=N—W (II), wherein W is as defined under formula I, by means of a compound of formula IIIb (IIIb)

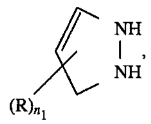

wherein R and $n_1$ are as defined under formula I, into the compound of formula IVb (IVb)

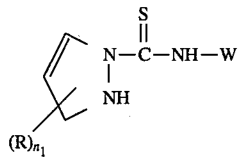

and then reacting the latter with a compound of formula V $CZCl_2$ (V), wherein Z is oxygen or sulfur, in the presence of a base.

Compounds of formula Ia can also be prepared by hydrogenating compounds of formula Ib. Such hydrogenation processes are known to the person skilled in the art. They may be carried out, for example, with hydrogen in the presence of noble metal catalysts, such as platinum.

The reaction of the isothiocyanates of formula II with the compounds of formulae IIIa and IIIb is advantageously carded out in an inert solvent at temperatures of from −5° C. to the boiling point of the solvent, especially from 0° to +50° C., especially preferably at room temperature. Suitable solvents for this reaction are, for example, toluene, xylene, ethyl acetate and acetonitrile.

The reaction of the compounds of formulae IVa and IVb with the compound of formula V is advantageously carded out in an inert solvent at low temperatures, preferably at from 0° to +50° C., especially preferably at from 0° to +15° C. Suitable bases for this reaction are, for example, pyridine, triethylamine and N,N-dimethylaniline. Suitable solvents are, for example, 1,2-dichloroethane, dichloromethane and toluene.

The compounds of formulae IIIa and IIIb used as starting materials for the compounds of formula I according to the invention are known or can be prepared analogously to methods known in the literature. The preparation of such compounds from 1,3-dibromopropanes and hydrazine is described, for example, in J.A.C.S. 88, 3959–3963 (1966). The preparation of the compounds of formulae IIIa and IIIb may also be carried out analogously to the process for preparing 1,2-diazacycloheptenes from the 1,2-dicarbalkoxy-1,2-diazacyclopentane starting materials, which is described in J. Org. Chem. 46, 442–446 (1981).

Compounds of formula IIIa wherein R is in the 4-position and $n_1$ is 0, 1 or 2 can also be prepared according to reaction scheme 1:

Reaction scheme 1:

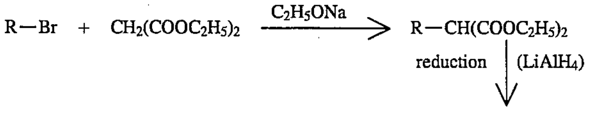

-continued

Reaction scheme 1:

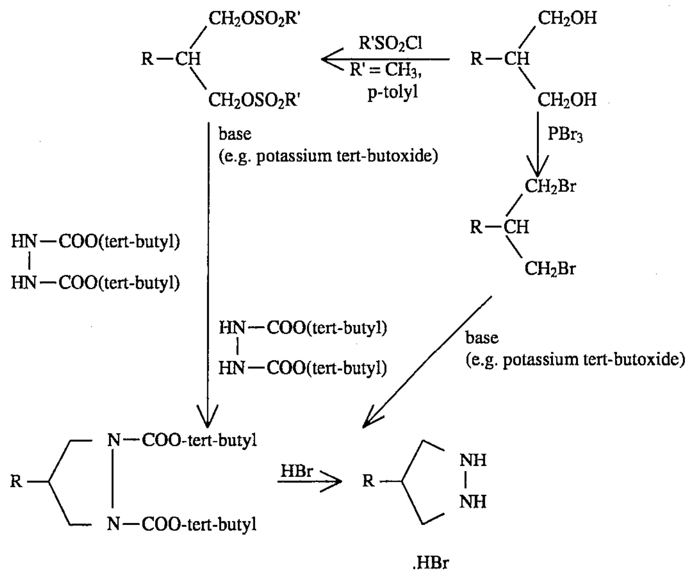

The isothiocyanates of formula II are known or can be prepared analogously to known methods. Such compounds are described, for example, in EP-A-0 304 920, EP-A-0 238 711, EP-A-0 409 025, EP-A-0 373 461, EP-A-0 311 135 and DE-OS-3 724 098.

The compounds of formula I are generally employed successfully at rates of application of from 0.001 to 4 kg/ha, especially from 0.005 to 1 kg/ha. The rate of application required to achieve the desired effect may be determined by experiments. It is dependent on the type of action, the stage of development of the cultivated plant and of the weeds, and the application (place, time, method) and, in dependence on those parameters, may vary within a wide range.

At relatively low rates of application the compounds of formula I are distinguished by growth-inhibiting and herbicidal properties, which render them excellently suitable for use in crops of useful plants, especially in cereals, cotton, soybeans, rape, maize and rice, their use in soybean crops being very especially preferred.

The invention relates also to herbicidal compositions comprising a novel compound of formula I, and to methods of inhibiting plant growth.

For the use of the compounds of formula I, or of compositions comprising them, for regulating plant growth, various methods and techniques come into consideration, such as, for example, the following:

i) Seed dressing a) Dressing the seeds with an active ingredient formulated as a wettable powder, by shaking in a container until the formulation is uniformly distributed over the surface of the seeds (dry dressing). In this case, up to 4 g of compound of formula I (for a 50% formulation: up to 8.0 g of wettable powder) are used per 1 kg of seed.

b) Dressing the seeds with an emulsifiable concentrate of the active ingredient or with an aqueous solution of the compound of formula I formulated as a wettable powder according to method a) (wet dressing).

c) Dressing by immersing the seeds for from 1 to 72 hours in a mixture comprising up to 1000 ppm of compound of formula I and, where appropriate, subsequently drying the seeds (seed soaking).

Dressing the seeds or treating the germinated seedling are naturally the preferred methods of application, because the active ingredient treatment is aimed entirely at the target crop. From 0.001 g to 4.0 g of active ingredient are generally used per 1 kg of seed, it being possible to use amounts which exceed or fall short of the given concentration limits, depending on the method employed, which also permits the addition of other active ingredients or micronutrients (repetition dressing).

ii) Controlled release of active ingredient

The active ingredient is applied in solution to granulated mineral carriers or polymerised granules (urea/formaldehyde) and allowed to dry. Where appropriate, a coating may be applied (coated granules), which allows the active ingredient to be released in metered amounts over a specific period of time.

The compounds of formula I are used in unmodified form, as obtainable from the synthesis, or, preferably, together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, wetting, scattering, or pouring, are chosen in accordance with the intended objectives and the prevailing circumstances.

The formulations, i.e. the compositions, preparations or mixtures comprising the compound (active ingredient) of formula I and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and esters thereof, such as rape oil, castor oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers am porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described inter alia in the following publications:

"McCutcheon's Detergents and Emulsifiers Annual", MC Publishing Corp., Glen Rock, N.J., 1988.

M. and J. Ash, "Encyclopedia of Surfactants", Vol. I–III, Chemical Publishing Co., New York, 1980–1981.

Dr. Helmut Stache, "Tensid-Taschenbuch", Carl Hanser Verlag, Munich/Vienna, 1981.

The pesticidal compositions usually comprise 0.1 to 99%, preferably 0.1 to 95%, of a compound of formula I, 1 to 99% of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries such as stabilisers, e.g. vegetable oils or epoxidised vegetable oils (epoxidised coconut oil, rape oil or soybean oil), anti-foams, e.g. silicone oil, preservatives, viscosity regulators, binders, tackifiers as well as fertilisers or other active ingredients for obtaining special effects.

Preferred formulations have especially the following composition (throughout, percentages are by weight):

| | |
|---|---|
| Emulsifiable concentrates: | |
| active ingredient: | 1 to 20%, preferably 5 to 10% |
| surface-active agent: | 5 to 30%, preferably 10 to 20% |
| liquid carrier: | 15 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

PREPARATION EXAMPLES

Example P1

Preparation of hydrazine-N,N'-dicarboxylic acid di-tert-butyl ester (formula V)

A solution of 98.1 g (0.45 mol) of $(BOC)_{2O}$ in 225 ml of tetrahydrofuran is added dropwise at a temperature of from +20° to +30° C. to a solution of 59.4 g (0.45 mol) of hydrazinecarboxylic acid tert-butyl ester in 225 ml of THF. The mixture is stirred for 12 hours to complete the reaction and then the solution is concentrated, yielding 103.2 g (98.9%) of (V) in the form of white crystals having a melting point of 123°–125° C.

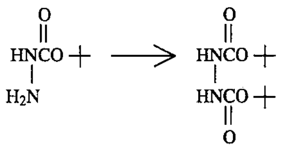

VI V

Example P2

Preparation of pyrazolidine-N,N'-dicarboxylic acid di-tert-butyl ester (formula VII)

9 g (0.08 mol) of potassium tert-butoxide are added in portions at a maximum of 35° C. to a solution of 9.3 g (0.04 mol) of VI in 40 ml of THF and 40 ml of tert-butanol. The mixture is stirred for one hour at RT and is then concentrated and dried under a high vacuum at a temperature of 50° C. The resulting potassium salt is suspended in 80 ml of DMF. Then 4.5 ml (0.044 mol) of 1,3-dibromopropane are added dropwise thereto at a maximum temperature of 33° C. and the mixture is stirred at room temperature for 18 hours. The resulting suspension is concentrated, 300 ml of diethyl ether are added thereto, and the mixture is washed with water, dried and then concentrated, yielding 8.1 g (74.4%) of (VII) in the form of a yellow oil.

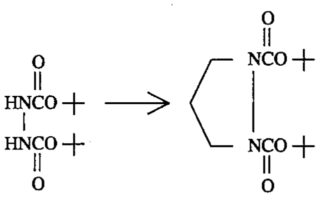

V VII

Example P3

Preparation of pyrazolidine dihydrobromide (formula VIII)

27 ml (0.11 mol) of a 33% solution of HBr in glacial acetic acid are added dropwise at room temperature to a solution of 14.3 g (0.05 mol) of 95% pyrazolidine-N,N'-dicarboxylic acid di-tert-butyl ester in 150 ml of ether. The mixture is stirred at room temperature for 18 hours and then the resulting white suspension is diluted with 100 ml of ether and filtered using a suction filter, yielding 9.7 g (82.9%) of pyrazolidine dihydrobromide in the form of white hygroscopic crystals.

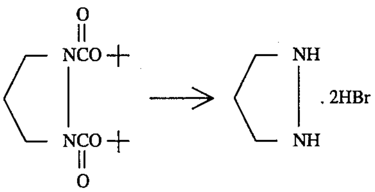

VII VIII

Example P4

Preparation of α-[2-chloro-4-fluoro-5-(pyrazolidinylthiocarbonylamino)phenylthio]acetic acid methyl ester (formula IX)

14 g (0.1 mol) of $K_2CO_3$ are added to a suspension of 5 g (0.021 mol) of pyrazolidine dihydrobromide in 200 ml of THF, and the mixture is stirred at room temperature for one hour. 5.8 g (0.02 mol) of an isothiocyanate of formula IIa are then added, and the mixture is stirred at room temperature for 18 hours. Filtering, concentrating and purifying by column chromatography yield 3.6 g (50%) of α-[2-chloro-4-fluoro-5-(pyrazolidinylthiocarbonylamino)phenylthio] acetic acid methyl ester (formula IX) having a melting point of 137°–141 ° C. in the form of white crystals.

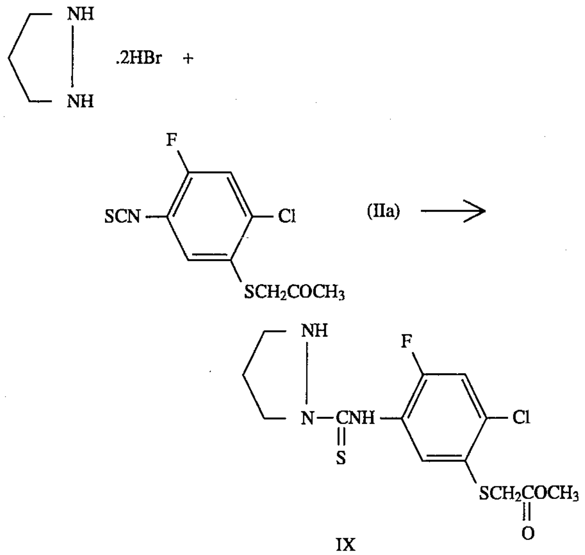

(IIa)

IX

Example P5

Preparation of 8-(4-chloro-2-fluoro-5-methoxycarbonylmethylthiophenylimino)-7-thia-1,5-diazabicyclo[3.3.0]octan-6-one (formula X)

4.1 g (8 mmol) of a 20% phosgene solution in toluene are added dropwise at a temperature of 0° to +5° C. to a suspension of 2.6 g (7 mmol) of IX in 50 ml of toluene, and the mixture is stirred at room temperature for 18 hours. After the addition of 200 ml of THF, the mixture is washed with saturated sodium chloride solution, concentrated and purified by column chromatography, yielding 2.1 g (77%) of 8-(4-chloro-2-fluoro-5-methoxycarbonylmethylthiophenylimino)-7-thia-1,5-diazabicyclo[3.3.0]octan-6-one in the form of white crystals having a melting point of 97°–98° C.

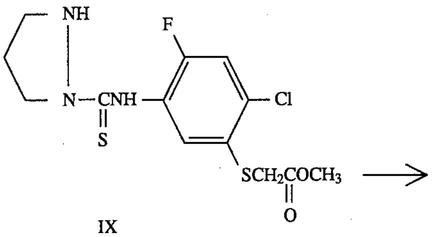

IX

-continued

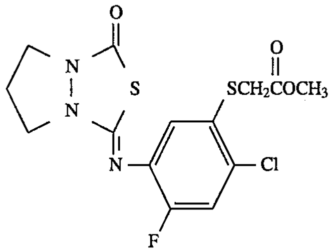

X

TABLE 1

Compounds Of formula Ic:

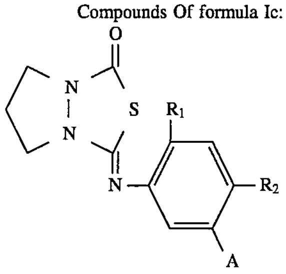

(Ic)

| Comp. No. | $R_1$ | $R_2$ | A | Phys. data |
|---|---|---|---|---|
| 1.001 | F | Cl | $-H$ | |
| 1.002 | F | Cl | $-CN$ | |
| 1.003 | F | Cl | $-NO_2$ | |
| 1.004 | F | Cl | $-COOH$ | m.p. > 190° C. (d) |
| 1.005 | F | Cl | $-COOCH_3$ | m.p. 126–128° C. |
| 1.006 | F | Cl | $-COOC_2H_5$ | |
| 1.007 | F | Cl | $-COOC_3H_7$ | |
| 1.008 | F | Cl | $-COOCH(CH_3)_2$ | m.p. 82–84° C. |
| 1.009 | F | Cl | $-COOC_4H_9$ | |
| 1.010 | F | Cl | $-COOCH-\underset{CH_3}{\underset{\mid}{CH_2}}-CH_3$ | |
| 1.011 | F | Cl | $-COOCH-CH_2-CH\begin{smallmatrix}CH_3\\CH_3\end{smallmatrix}$ | |
| 1.012 | F | Cl | $-COOC_5H_{11}$ | |
| 1.013 | F | Cl | $-COOCH_2-CH_2-O-CH_3$ | |
| 1.014 | F | Cl | $-COOCH_2-CH_2-O-C_2H_5$ | |
| 1.015 | F | Cl | $-COOCH-(CH_3)-CH_2-OCH_3$ | |
| 1.016 | F | Cl | $-COOCH_2-CH_2-S-CH_3$ | |
| 1.017 | F | Cl | $-COOCH-(CH_3)-CH_2-S-CH_3$ | |
| 1.018 | F | Cl | $COOCH-(CH_3)-CH_2-S-C_2H_5$ | |
| 1.019 | F | Cl | $COOCH-(CH_3)-CH_2-S-C_3H_7$ | |
| 1.020 | F | Cl | $COOCH(CH_3)-CH_2-S-CH\begin{smallmatrix}CH_3\\CH_3\end{smallmatrix}$ | |
| 1.021 | F | Cl | $COOCH(CH_3)-CH_2-S-C_4H_9$ | |
| 1.022 | F | Cl | $COOCH(CH_3)-CH_2-S-\underset{n}{C_5}H_{11}$ | |
| 1.023 | F | Cl | $COOCH(CH_3)-CH_2-N\begin{smallmatrix}CH_3\\CH_3\end{smallmatrix}$ | |

TABLE 1-continued
Compounds Of formula Ic:
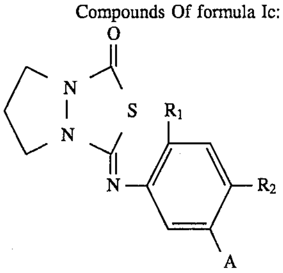
(Ic)
| Comp. No. | $R_1$ | $R_2$ | A | Phys. data |
|---|---|---|---|---|
| 1.024 | F | Cl | 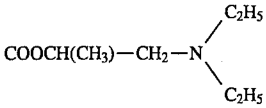 | |
| 1.025 | F | Cl | $-CONH_2$ | |
| 1.026 | F | Cl | $CONH-CH_3$ | |
| 1.027 | F | Cl | 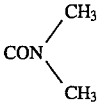 | m.p. > 65° C. |
| 1.028 | F | Cl | 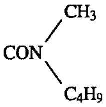 | (waxy) |
| 1.029 | F | Cl | 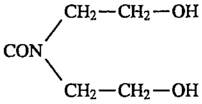 | |
| 1.030 | F | Cl | $CONH-CH_2-CH=CH_2$ | |
| 1.031 | F | Cl | $CON(CH_2-CH=CH_2)$ | |
| 1.032 | F | Cl | 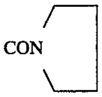 | |
| 1.033 | F | Cl | 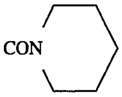 | |
| 1.034 | F | Cl | 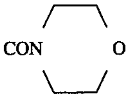 | |
| 1.035 | F | Cl | 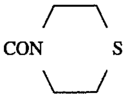 | |
| 1.036 | F | Cl | 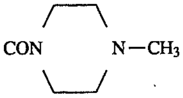 | |
| 1.037 | F | Cl | 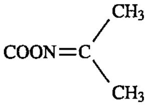 | |
| 1.038 | F | Cl | $COOCH_2-CH_2-Cl$ | |
| 1.039 | F | Cl | $COOCH_2-CN$ | |

TABLE 1-continued
Compounds Of formula Ic:
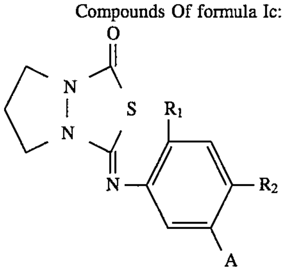
(Ic)
| Comp. No. | $R_1$ | $R_2$ | A | Phys. data |
|---|---|---|---|---|
| 1.040 | F | Cl | 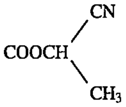 | |
| 1.041 | F | Cl | $COOCH_2-CH_2=CH_2$ | |
| 1.042 | F | Cl | $COOCH_2-CH_2=CHCl$ | |
| 1.043 | F | Cl | 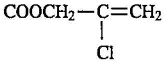 | |
| 1.044 | F | Cl | $COOCH_2-C\equiv CH$ | |
| 1.045 | F | Cl | 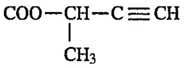 | |
| 1.046 | F | Cl | 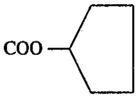 | |
| 1.047 | F | Cl | 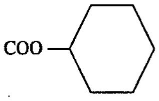 | |
| 1.048 | F | Cl | 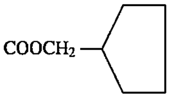 | |
| 1.049 | F | Cl | 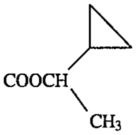 | |
| 1.050 | F | Cl | 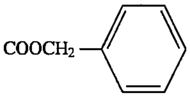 | |
| 1.051 | F | Cl | 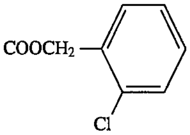 | |
| 1.052 | F | Cl | 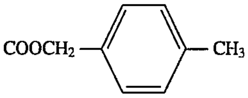 | |
| 1.053 | F | Cl | $COSCH_3$ | |
| 1.054 | F | Cl | $COSC_2H_5$ | |
| 1.055 | F | Cl | $COSC_3H_7$ | |
| 1.056 | F | Cl | $COS-CH_2-CH=CH_2$ | |
| 1.057 | F | Cl | $COS-CH_2-COOCH_3$ | (amorphous) |

TABLE 1-continued

Compounds Of formula Ic:

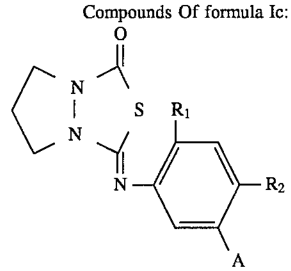

(Ic)

| Comp. No. | $R_1$ | $R_2$ | A | Phys. data |
|---|---|---|---|---|
| 1.058 | F | Cl | $COS-CH_2-COOC_2H_5$ | |
| 1.059 | F | Cl | $COS-CH_2-COOC_5H_{11}$ | |
| 1.060 | F | Cl | $COS-CH-COOCH_3$<br>$CH_3$ | |
| 1.061 | F | Cl | $COS-CH-COOC_2H_5$<br>$CH_3$ | |
| 1.062 | F | Cl | $COS-CH-COOC_3H_7$<br>$CH_3$ | |
| 1.063 | F | Cl | $COS-CH_2-CH_2-COOCH_3$ | |
| 1.064 | F | Cl | $COS-CH_2-COOCH_2-CH_2-O-CH_3$ | |
| 1.065 | F | Cl | $COOCH_2-COOCH_3$ | |
| 1.066 | F | Cl | $COOCH-COOCH_3$<br>$CH_3$ | |
| 1.067 | F | Cl | $COOCH_2-COOC_5H_{11}$ | |
| 1.068 | F | Cl | $COOCH_2-CH_2-Si(CH_3)_3$ | |
| 1.069 | F | Cl | COONa | |
| 1.070 | F | Cl | $CH_3$<br>$COOCH_2-CH_2-O-N=C$<br>$CH_3$ | |
| 1.071 | F | Cl | OH | |
| 1.072 | F | Cl | $OCH_3$ | |
| 1.073 | F | Cl | $OC_2H_5$ | |
| 1.074 | F | Cl | $OC_3H_7$ | |
| 1.075 | F | Cl | $CH_3$<br>OCH<br>$CH_3$ | m.p. 120–121° C. |
| 1.076 | F | Cl | $OC_4H_9$ | |
| 1.077 | F | Cl | $OCH-C_2H_5$<br>$CH_3$ | |
| 1.078 | F | Cl | $CH_3$<br>$O-CH_2-CH$<br>$CH_3$ | |
| 1.079 | F | Cl | $OCH_2CH=CH_2$ | |
| 1.080 | F | Cl | $OCH_2-C=CH_2$<br>Cl | |
| 1.081 | F | Cl | $OCH_2CH=CHCl$ | |
| 1.082 | F | Cl | $OCH_2C\equiv CH$ | |

TABLE 1-continued

Compounds Of formula Ic:

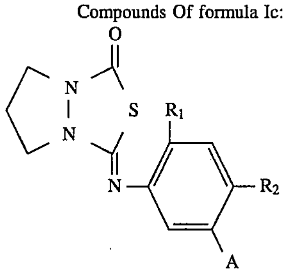

(Ic)

| Comp. No. | $R_1$ | $R_2$ | A | Phys. data |
|---|---|---|---|---|
| 1.083 | F | Cl | $OCH-C\equiv CH$<br>$CH_3$ | |
| 1.084 | F | Cl | $-OCH_2-COOCH_3$ | |
| 1.085 | F | Cl | $-O-CH_2-COOC_5H_{11}$ | |
| 1.086 | F | Cl | $O-CH-COOCH_3$<br>$CH_3$ | |
| 1.087 | F | Cl | $O-CH_2-COOC_2H_5$ | |
| 1.088 | F | Cl | $O-CH-COOC_2H_5$<br>$CH_3$ | |
| 1.089 | F | Cl | $O-CH_2-CH_2-O-CH_3$ | |
| 1.090 | F | Cl | $O-CH-CH_2-S-CH_3$<br>$CH_3$ | |
| 1.091 | F | Cl | $O-CH-CH_2-S-C_2H_5$<br>$CH_3$ | |
| 1.092 | F | Cl | $O-CH-CH_2-S-C_3H_7$<br>$CH_3$ | |
| 1.093 | F | Cl | $O-CH_2-CH_2-Cl$ | |
| 1.094 | F | Cl | $O-CH_2-CN$ | |
| 1.095 | F | Cl | $O-CH-CN$<br>$CH_3$ | |
| 1.096 | F | Cl | $S-CH_3$ | |
| 1.097 | F | Cl | $S-C_2H_5$ | |
| 1.098 | F | Cl | $S-C_3H_7$ | |
| 1.099 | F | Cl | $CH_3$<br>$S-CH$<br>$CH_3$ | |
| 1.100 | F | Cl | $S-CH_2-CH-CH_2$ | |
| 1.101 | F | Cl | $S-CH_2-C=CH_2$<br>$Cl$ | |
| 1.102 | F | Cl | $S-CH_2-CH=CHCl$ | |
| 1.103 | F | Cl | $S-CH_2-C\equiv CH$ | |
| 1.104 | F | Cl | $S-CH-C\equiv CH$<br>$CH_3$ | |
| 1.105 | F | Cl | $S-CH_2-COOCH_3$ | m.p. 97–98° C. |
| 1.106 | F | Cl | $S-CH_2-COOC_2H_5$ | |
| 1.107 | F | Cl | $S-CH_2-COOC_5H_{11}$ | |

TABLE 1-continued

Compounds Of formula Ic:

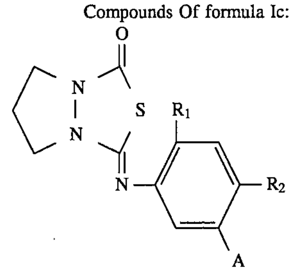

(Ic)

| Comp. No. | $R_1$ | $R_2$ | A | Phys. data |
|---|---|---|---|---|
| 1.108 | F | Cl | $S-CH-COOCH_3$<br>$\quad\;\; \vert$<br>$\quad\; CH_3$ | |
| 1.109 | F | Cl | $S-CH-COOC_2H_5$<br>$\quad\;\; \vert$<br>$\quad\; CH_3$ | |
| 1.110 | F | Cl | $S-CH_2-COOCHl-CH_2-O-CH_3$ | |
| 1.111 | F | Cl | 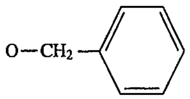 | |
| 1.112 | F | Cl | 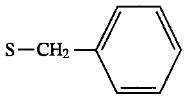 | |
| 1.114 | F | Cl | $-C-CN$<br>$\;\Vert$<br>$N-O-CH_3$ | |
| 1.115 | F | Cl | $-C-CN$<br>$\;\Vert$<br>$N-O-CH_2-COOCH_3$ | |
| 1.116 | F | Cl | $-C-CN$<br>$\;\Vert$<br>$N-O-CH_2-C\equiv CH$ | |
| 1.117 | F | Cl | $-C-CH_3$<br>$\;\Vert$<br>$N-O-CH_3$ | |
| 1.118 | F | Cl | $-C-CH_3$<br>$\;\Vert$<br>$N-O-CH_2-C\equiv CH$ | |
| 1.119 | F | Cl | $-C-CH_2-O-CH_3$<br>$\;\Vert$<br>$N-O-CH_3$ | |
| 1.120 | F | Cl | $\quad O-CH_3$<br>$\;\;/$<br>$-C$<br>$\vert\;\;\backslash$<br>$\vert\quad O-CH_3$<br>$CH_3$ | |
| 1.121 | F | Cl | $\quad O-C_2H_5$<br>$\;\;/$<br>$-C$<br>$\vert\;\;\backslash$<br>$\vert\quad O-C_2H_5$<br>$CH_3$ | |
| 1.122 | F | Cl | 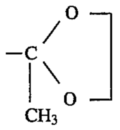 | |

TABLE 1-continued
Compounds Of formula Ic:
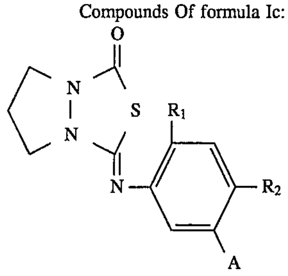
(Ic)
| Comp. No. | $R_1$ | $R_2$ | A | Phys. data |
|---|---|---|---|---|
| 1.123 | F | Cl | 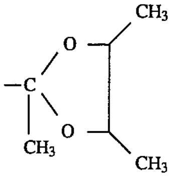 | |
| 1.124 | F | Cl | 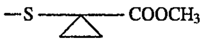 | |
| 1.125 | F | Cl | 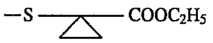 | m.p. 127–130° C. |
| 1.126 | F | Cl | 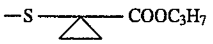 | |
| 1.127 | F | Cl | 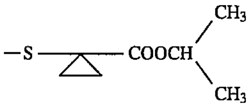 | |
| 1.128 | F | Cl | 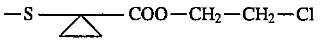 | |
| 1.129 | F | Cl | 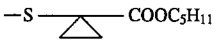 | |
| 1.130 | F | Cl | 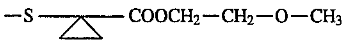 | |
| 1.131 | F | Cl | 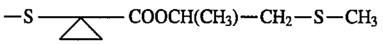 | |
| 1.132 | F | Cl | 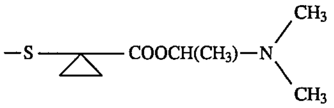 | |
| 1.133 | F | Cl | 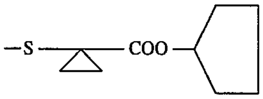 | |
| 1.134 | F | Cl | 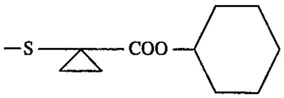 | |
| 1.135 | F | Cl | 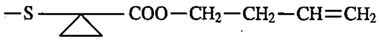 | |
| 1.136 | F | Cl | 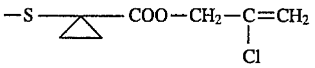 | |
| 1.137 | F | Cl | 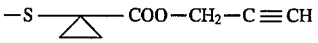 | |
| 1.138 | F | Cl | 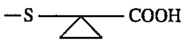 | m.p. >180° C. (decomp.) |

TABLE 1-continued
Compounds Of formula Ic:
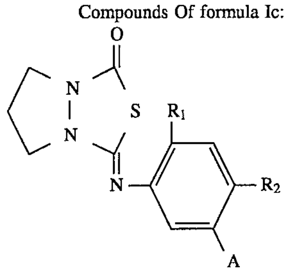
(Ic)
| Comp. No. | $R_1$ | $R_2$ | A | Phys. data |
|---|---|---|---|---|
| 1.139 | F | Cl | 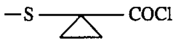 | |
| 1.140 | F | Cl | 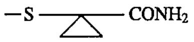 | |
| 1.141 | F | Cl | 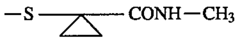 | |
| 1.142 | F | Cl | 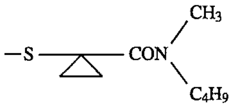 | |
| 1.143 | F | Cl | 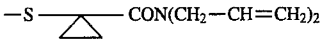 | |
| 1.144 | F | Cl | 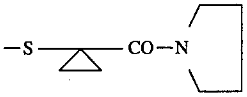 | |
| 1.145 | F | Cl | 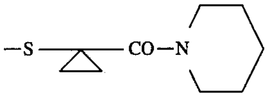 | |
| 1.146 | F | Cl | 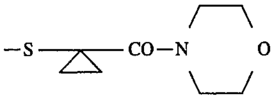 | |
| 1.147 | F | Cl | 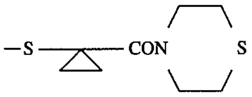 | |
| 1.148 | F | Cl | 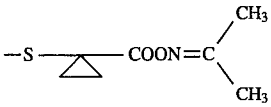 | |
| 1.149 | F | Cl | 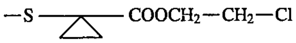 | |
| 1.150 | F | Cl | 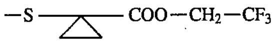 | |
| 1.151 | F | Cl | 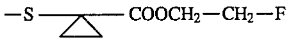 | |
| 1.152 | F | Cl | 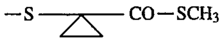 | |
| 1.153 | F | Cl | 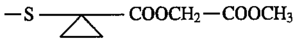 | |
| 1.154 | F | Cl | 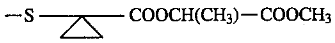 | |
| 1.155 | F | Cl | 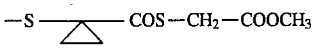 | |

TABLE 1-continued
Compounds Of formula Ic:
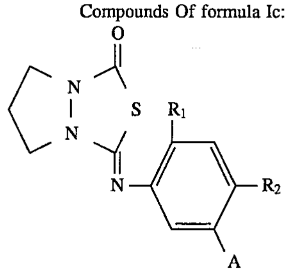
(Ic)
| Comp. No. | $R_1$ | $R_2$ | A | Phys. data |
|---|---|---|---|---|
| 1.156 | F | Cl | 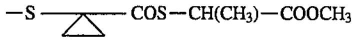 | |
| 1.157 | F | Cl | 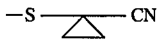 | |
| 1.158 | F | Cl | 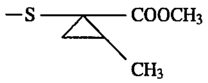 | |
| 1.159 | F | Cl | 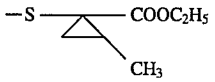 | |
| 1.160 | F | Cl | 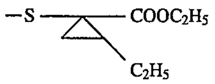 | |
| 1.161 | F | Cl | 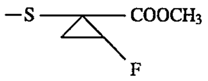 | |
| 1.162 | F | Cl | 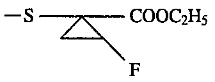 | |
| 1.163 | F | Cl | 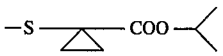 | |
| 1.164 | F | Cl | 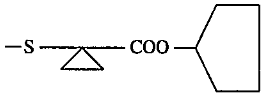 | |
| 1.165 | F | Cl | 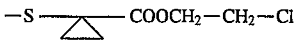 | |
| 1.166 | F | Cl | 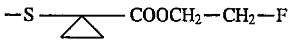 | |
| 1.167 | F | Cl | 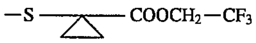 | |
| 1.168 | F | Cl | 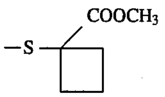 | |
| 1.169 | F | Cl | 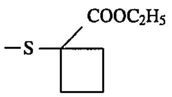 | |
| 1.170 | F | Cl | 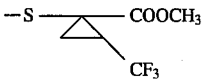 | |
| 1.171 | F | Cl | 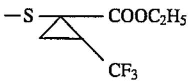 | |

TABLE 1-continued
Compounds Of formula Ic:
(Ic)
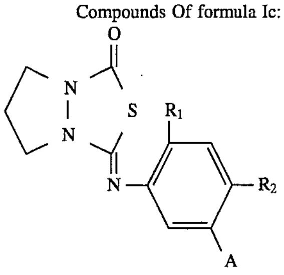
| Comp. No. | $R_1$ | $R_2$ | A | Phys. data |
|---|---|---|---|---|
| 1.172 | F | Cl | 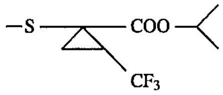 | |
| 1.173 | F | Cl | 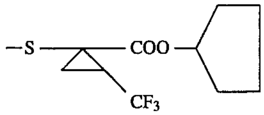 | |
| 1.174 | F | Cl | 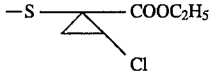 | |
| 1.175 | F | Cl | 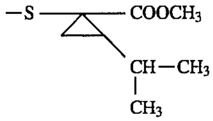 | |
| 1.176 | F | Cl | 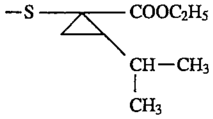 | |
| 1.177 | F | Cl | $-NH-SO_2-CH_3$ | |
| 1.178 | F | Cl | $-NH-SO_2-C_2H_5$ | |
| 1.179 | F | Cl | $-NH-SO_2-Cl$ | |
| 1.180 | F | Cl | 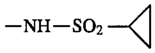 | |
| 1.181 | F | Cl | 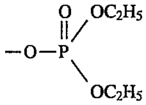 | |
| 1.182 | H | Cl | $-COOH$ | |
| 1.183 | H | Cl | $-COOCH_3$ | |
| 1.184 | H | Cl | 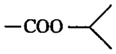 | |
| 1.185 | H | Cl | $-COO-C_5H_{11}$ | |
| 1.186 | H | Cl | $-COO-CH_2-CH_2-O-CH_3$ | |
| 1.187 | H | Cl | $-COOCH_2-S-CH_3$ | |
| 1.188 | H | Cl | $-COOCH-(CH)_3-CH_2-S-CH_3$ | |
| 1.189 | H | Cl | 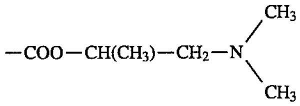 | |
| 1.190 | H | Cl | 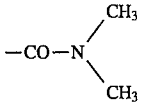 | |

TABLE 1-continued
Compounds Of formula Ic:
(Ic)
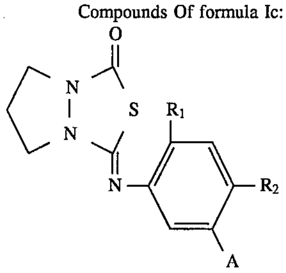
| Comp. No. | $R_1$ | $R_2$ | A | Phys. data |
|---|---|---|---|---|
| 1.191 | H | Cl | 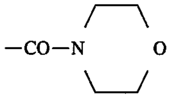 | |
| 1.192 | H | Cl | 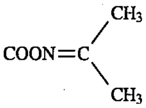 | |
| 1.193 | H | Cl | 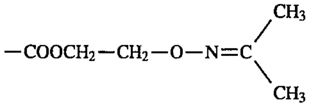 | |
| 1.194 | H | Cl | 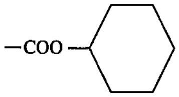 | |
| 1.195 | H | Cl | 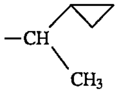 | |
| 1.196 | H | Cl | $-S-C_3H_7$ | |
| 1.197 | H | Cl | $-COOCH_2-COOCH_3$ | |
| 1.198 | H | Cl | $-COOCH(CH_3)-COOCH_3$ | |
| 1.199 | H | Cl | $-COS-CH_2-COOCH_3$ | |
| 1.200 | H | Cl | $-COS-CH(CH_3)-COOCH_3$ | |
| 1.201 | H | Cl | OH | |
| 1.202 | H | Cl | $OCH_3$ | |
| 1.203 | H | Cl | $O-C_2H_5$ | |
| 1.204 | H | Cl | 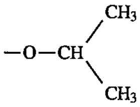 | |
| 1.205 | H | Cl | $-O-CH_2-C{\equiv}CH$ | |
| 1.206 | H | Cl | $-O-CH_2-CH_2{=}CHCl$ | |
| 1.207 | H | Cl | 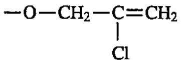 | |
| 1.208 | H | Cl | 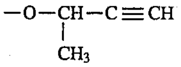 | |
| 1.209 | H | Cl | $-O-CH_2-COOCH_3$ | |
| 1.210 | H | Cl | $-O-CH_2-COOC_2H_{11}$ | |
| 1.211 | H | Cl | $-O-CH(CH_3)-COOCH_3$ | |
| 1.212 | H | Cl | $-SH$ | |
| 1.213 | H | Cl | $-SCH_3$ | |
| 1.214 | H | Cl | $-SC_2H_5$ | |
| 1.215 | H | Cl | 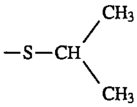 | |

TABLE 1-continued
Compounds Of formula Ic:
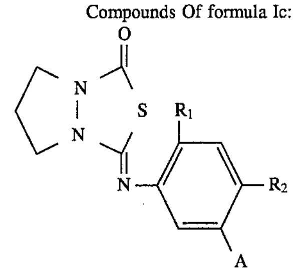
(Ic)
| Comp. No. | $R_1$ | $R_2$ | A | Phys. data |
|---|---|---|---|---|
| 1.216 | H | Cl | $-S-CH_2-COOCH_3$ | |
| 1.217 | H | Cl | $-S-CH(CH_3)COOCH_3$ | |
| 1.218 | H | Cl | $-S-CH_2-COOC_2H_5$ | |
| 1.219 | H | Cl | 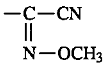 | |
| 1.220 | H | Cl | 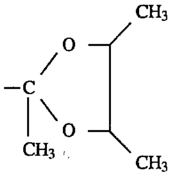 | |
| 1.221 | H | Cl | 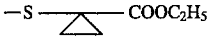 | |
| 1.222 | H | Cl | 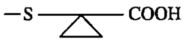 | |
| 1.223 | H | Cl | 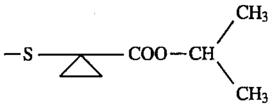 | |
| 1.224 | H | Cl | 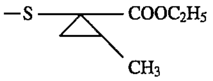 | |
| 1.225 | H | Cl | 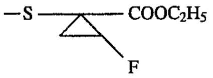 | |
| 1.226 | H | Cl | 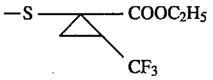 | |
| 1.227 | H | Cl | 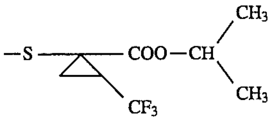 | |
| 1.228 | H | Cl | 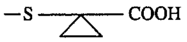 | |
| 1.229 | H | Cl | 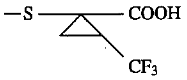 | |
| 1.230 | H | Cl | 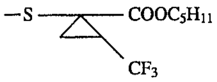 | |
| 1.231 | H | Cl | 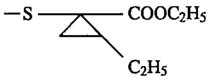 | |

TABLE 1-continued
Compounds Of formula Ic:
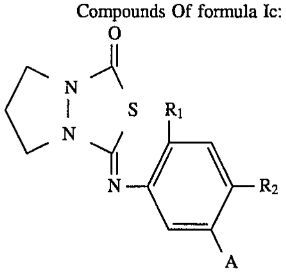
(Ic)
| Comp. No. | $R_1$ | $R_2$ | A | Phys. data |
|---|---|---|---|---|
| 1.232 | H | Cl | 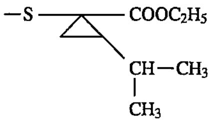 | |
| 1.233 | H | Cl | $-NH-SO_2-C_2H_5$ | |
| 1.234 | H | Cl | $-NH-SO_2-CH_2-Cl$ | |
| 1.235 | H | Cl | 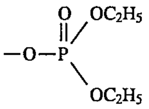 | |
| 1.236 | F | CN | $-COOH$ | |
| 1.237 | F | CN | 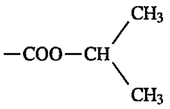 | |
| 1.238 | F | CN | 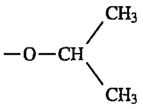 | |
| 1.239 | F | CN | $-O-CH_2-C\equiv CH$ | |
| 1.240 | F | CN | $-O-CH(CH_3)-C\equiv CH$ | |
| 1.241 | F | CN | $-S-CH_2-COOCH_3$ | |
| 1.242 | F | CN | $-S-CH(CH_3)-COOCH_3$ | |
| 1.243 | F | CN | $-O-CH_2-COOCH_3$ | |
| 1.244 | F | CN | $-O-CH_2-COOC_5H_{11}$ | |
| 1.245 | F | CN | $-O-CH(CH_3)$-$COOC_2H_5$ | |
| 1.246 | F | CN | 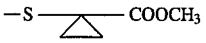 | |
| 1.247 | F | CN | 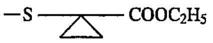 | |
| 1.248 | F | CN | 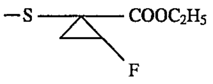 | |
| 1.249 | F | CN | 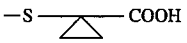 | |
| 1.250 | F | CN | 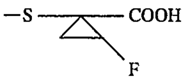 | |
| 1.251 | F | CN | 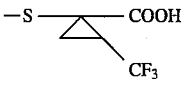 | |
| 1.252 | F | CN | 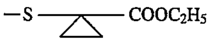 | |
| 1.253 | F | Br | $-COOH$ | |

TABLE 1-continued
Compounds Of formula Ic:
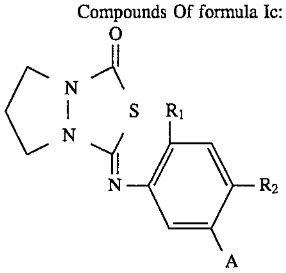
(Ic)
| Comp. No. | $R_1$ | $R_2$ | A | Phys. data |
|---|---|---|---|---|
| 1.254 | F | Br | 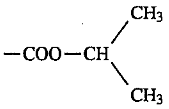 | |
| 1.255 | F | Br | $-OH$ | |
| 1.256 | F | Br | 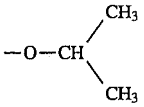 | |
| 1.257 | F | Br | $-O-CH_2-C{\equiv}CH$ | |
| 1.258 | F | Br | $-O-CH(CH_3)-C{\equiv}CH$ | |
| 1.259 | F | Br | $-O-CH_2COOCH_3$ | |
| 1.260 | F | Br | $-O-CH_2-COOC_5H_{11}$ | |
| 1.261 | F | Br | $S-CH_2-COOCH_3$ | |
| 1.262 | F | Br | 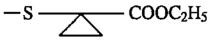 | |
| 1.263 | F | Br | 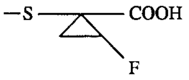 | |
| 1.264 | F | Br | 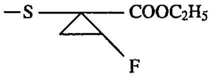 | |
TABLE 2
Compounds of formula Id:
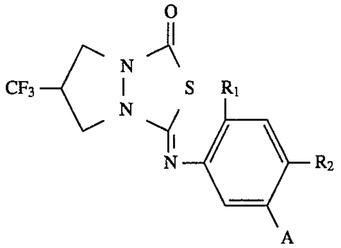
(Id)
| Comp. No. | $R_1$ | $R_2$ | A | Phys. data |
|---|---|---|---|---|
| 2.001 | F | Cl | $-H$ | |
| 2.002 | F | Cl | $-CN$ | |
| 2.003 | F | Cl | $-NO_2$ | |
| 2.004 | F | Cl | $-COOH$ | |
| 2.005 | F | Cl | $-COOCH_3$ | |
| 2.006 | F | Cl | $-COOC_2H_5$ | |
| 2.007 | F | Cl | $-COOC_3H_7$ | |
| 2.008 | F | Cl | $-COOCH(CH_3)_2$ | |
| 2.009 | F | Cl | $-COOC_4H_9$ | |

TABLE 2-continued
Compounds of formula Id:
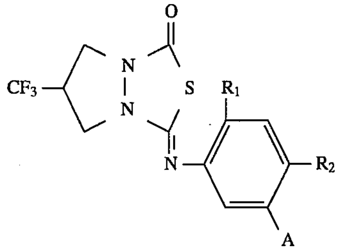
(Id)
| Comp. No. | $R_1$ | $R_2$ | A | Phys. data |
|---|---|---|---|---|
| 2.010 | F | Cl | 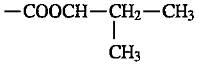 | |
| 2.011 | F | Cl | 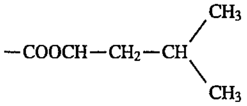 | |
| 2.012 | F | Cl | $-COOC_5H_{11}$ | |
| 2.013 | F | Cl | $-COOCH_2-CH_2-O-CH_3$ | |
| 2.014 | F | Cl | $-COOCH_2-CH_2-O-C_2H_5$ | |
| 2.015 | F | Cl | $-COOCH-(CH_3)-CH_2-OCH_3$ | |
| 2.016 | F | Cl | $-COOCH_2-CH_2-S-CH_3$ | |
| 2.017 | F | Cl | $-COOCH-(CH_3)-CH_2-S-CH_3$ | |
| 2.018 | F | Cl | $COOCH-(CH_3)-CH_2-S-C_2H_5$ | |
| 2.019 | F | Cl | $COOCH-(CH_3)-CH_2-S-C_3H_7$ | |
| 2.020 | F | Cl | 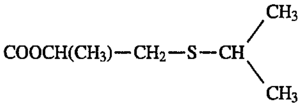 | |
| 2.021 | F | Cl | $COOCH(CH_3)-CH_2-S-C_4H_9$ | |
| 2.022 | F | Cl | $COOCH(CH_3)-CH_2-S-C_5H_{11}$ | |
| 2.023 | F | Cl | 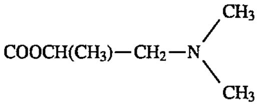 | |
| 2.024 | F | Cl | 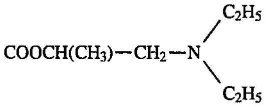 | |
| 2.025 | F | Cl | $-CONH_2$ | |
| 2.026 | F | Cl | $CONH-CH_3$ | |
| 2.027 | F | Cl | 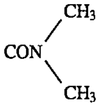 | |
| 2.028 | F | Cl | 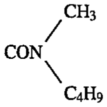 | |
| 2.029 | F | Cl | 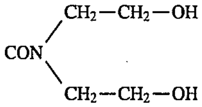 | |
| 2.030 | F | Cl | $CONH-CH_2-CH=CH_2$ | |
| 2.031 | F | Cl | $CON(CH_2-CH=CH_2)$ | |

TABLE 2-continued
Compounds of formula Id:
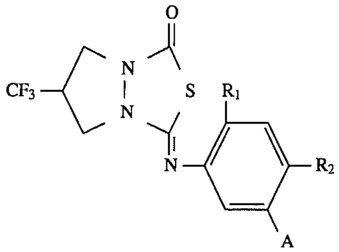
(Id)
| Comp. No. | $R_1$ | $R_2$ | A | Phys. data |
|---|---|---|---|---|
| 2.032 | F | Cl | 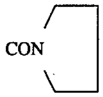 | |
| 2.033 | F | Cl | 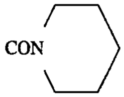 | |
| 2.034 | F | Cl | 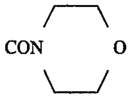 | |
| 2.035 | F | Cl | 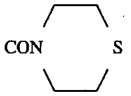 | |
| 2.036 | F | Cl | 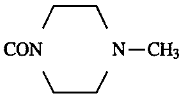 | |
| 2.037 | F | Cl | 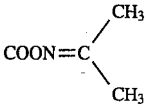 | |
| 2.038 | F | Cl | $COOCH_2-CH_2-Cl$ | |
| 2.039 | F | Cl | $COOCH_2-CN$ | |
| 2.040 | F | Cl | 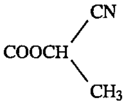 | |
| 2.041 | F | Cl | $COOCH_2-CH_2=CH_2$ | |
| 2.042 | F | Cl | $COOCH_2-CH_2=CHCl$ | |
| 2.043 | F | Cl | 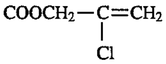 | |
| 2.044 | F | Cl | $COOCH_2-C\equiv CH$ | |
| 2.045 | F | Cl | 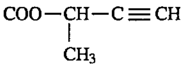 | |
| 2.046 | F | Cl | 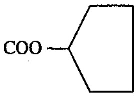 | |

TABLE 2-continued

Compounds of formula Id:

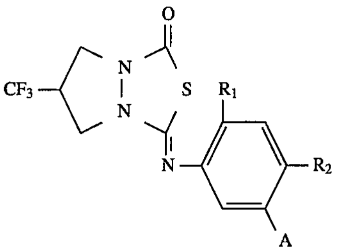

(Id)

| Comp. No. | $R_1$ | $R_2$ | A | Phys. data |
|---|---|---|---|---|
| 2.047 | F | Cl | COO 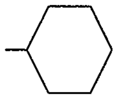 | |
| 2.048 | F | Cl | $COOCH_2$ 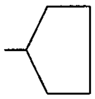 | |
| 2.049 | F | Cl | COOCH 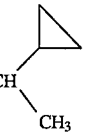 $CH_3$ | |
| 2.050 | F | Cl | $COOCH_2$ 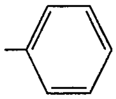 | |
| 2.051 | F | Cl | $COOCH_2$ 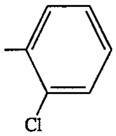 Cl | |
| 2.052 | F | Cl | $COOCH_2$ 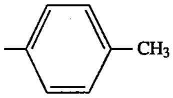 $CH_3$ | |
| 2.053 | F | Cl | $COSCH_3$ | |
| 2.054 | F | Cl | $COSC_2H_5$ | |
| 2.055 | F | Cl | $COSC_3H_7$ | |
| 2.056 | F | Cl | $COS-CH_2-CH=CH_2$ | |
| 2.057 | F | Cl | $COS-CH_2-COOCH_3$ | |
| 2.058 | F | Cl | $COS-CH_2-COOC_2H_5$ | |
| 2.059 | F | Cl | $COS-CH_2-COOC_5H_{11}$ | |
| 2.060 | F | Cl | $COS-\underset{\displaystyle CH_3}{\underset{\vert}{CH}}-COOCH_3$ | |
| 2.061 | F | Cl | $COS-\underset{\displaystyle CH_3}{\underset{\vert}{CH}}-COOC_2H_5$ | |
| 2.062 | F | Cl | $COS-\underset{\displaystyle CH_3}{\underset{\vert}{CH}}-COOC_3H_7$ | |
| 2.063 | F | Cl | $COS-CH_2-CH_2-COOCH_3$ | |
| 2.064 | F | Cl | $COS-CH_2-COOCH_2-CH_2-O-CH_3$ | |
| 2.065 | F | Cl | $COOCH_2-COOCH_3$ | |
| 2.066 | F | Cl | $COO\underset{\displaystyle CH_3}{\underset{\vert}{CH}}-COOCH_3$ | |

TABLE 2-continued

Compounds of formula Id:

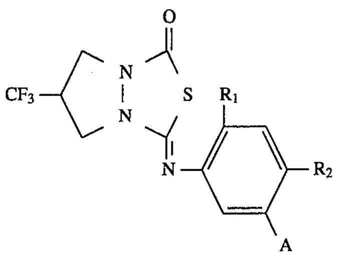

(Id)

| Comp. No. | $R_1$ | $R_2$ | A | Phys. data |
|---|---|---|---|---|
| 2.067 | F | Cl | $COOCH_2-COOC_5H_{11}$ | |
| 2.068 | F | Cl | $COOCH_2-CH_2-Si(CH_3)_3$ | |
| 2.069 | F | Cl | COONa | |
| 2.070 | F | Cl | $COOCH_2-CH_2-O-N=C(CH_3)_2$ | |
| 2.071 | F | Cl | OH | |
| 2.072 | F | Cl | $OCH_3$ | |
| 2.073 | F | Cl | $OC_2H_5$ | |
| 2.074 | F | Cl | $OC_3H_7$ | |
| 2.075 | F | Cl | $OCH(CH_3)_2$ | |
| 2.076 | F | Cl | $OC_4H_9$ | |
| 2.077 | F | Cl | $OCH(CH_3)-C_2H_5$ | |
| 2.078 | F | Cl | $O-CH_2-CH(CH_3)_2$ | |
| 2.079 | F | Cl | $OCH_2CH=CH_2$ | |
| 2.080 | F | Cl | $OCH_2-C(Cl)=CH_2$ | |
| 2.081 | F | Cl | $OCH_2CH=CHCl$ | |
| 2.082 | F | Cl | $OCH_2C\equiv CH$ | |
| 2.083 | F | Cl | $OCH(CH_3)-C\equiv CH$ | |
| 2.084 | F | Cl | $-OCH_2-COOCH_3$ | |
| 2.085 | F | Cl | $-O-CH_2-COOC_5H_{11}$ | |
| 2.086 | F | Cl | $O-CH(CH_3)-COOCH_3$ | |
| 2.087 | F | Cl | $O-CH_2-COOC_2H_5$ | |
| 2.088 | F | Cl | $O-CH(CH_3)-COOC_2H_5$ | |
| 2.089 | F | Cl | $O-CH_2-CH_2-O-CH_3$ | |

TABLE 2-continued

Compounds of formula Id:

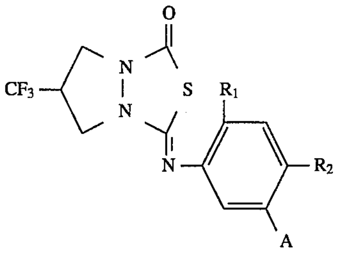

(Id)

| Comp. No. | $R_1$ | $R_2$ | A | Phys. data |
|---|---|---|---|---|
| 2.090 | F | Cl | $O-CH-CH_2-S-CH_3$<br>$CH_3$ | |
| 2.091 | F | Cl | $O-CH-CH_2-S-C_2H_5$<br>$CH_3$ | |
| 2.092 | F | Cl | $O-CH-CH_2-S-C_3H_7$<br>$CH_3$ | |
| 2.093 | F | Cl | $O-CH_2-CH_2-Cl$ | |
| 2.094 | F | Cl | $O-CH_2-CN$ | |
| 2.095 | F | Cl | $O-CH-CN$<br>$CH_3$ | |
| 2.096 | F | Cl | $S-CH_3$ | |
| 2.097 | F | Cl | $S-C_2H_5$ | |
| 2.098 | F | Cl | $S-C_3H_7$ | |
| 2.099 | F | Cl | $CH_3$<br>$S-CH$<br>$CH_3$ | |
| 2.100 | F | Cl | $S-CH_2-CH=CH_2$ | |
| 2.101 | F | Cl | $S-CH_2-C=CH_2$<br>$Cl$ | |
| 2.102 | F | Cl | $S-CH_2-CH=CHCl$ | |
| 2.103 | F | Cl | $S-CH_2-C\equiv CH$ | |
| 2.104 | F | Cl | $S-CH-C\equiv CH$<br>$CH_3$ | |
| 2.105 | F | Cl | $S-CH_2-COOCH_3$ | |
| 2.106 | F | Cl | $S-CH_2-COOC_2H_5$ | |
| 2.107 | F | Cl | $S-CH_2-COOC_5H_{11}$ | |
| 2.108 | F | Cl | $S-CH-COOCH_3$<br>$CH_3$ | |
| 2.109 | F | Cl | $S-CH-COOC_2H_5$<br>$CH_3$ | |
| 2.110 | F | Cl | $S-CH_2-COOCH_2-CH_2-O-CH_3$ | |
| 2.111 | F | Cl | 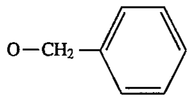 | |

TABLE 2-continued
Compounds of formula Id:
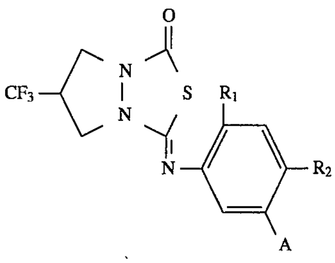
(Id)
| Comp. No. | $R_1$ | $R_2$ | A | Phys. data |
|---|---|---|---|---|
| 2.112 | F | Cl | 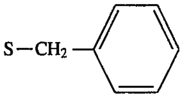 | |
| 2.114 | F | Cl | 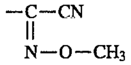 | |
| 2.115 | F | Cl | 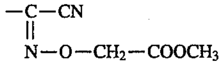 | |
| 2.116 | F | Cl | 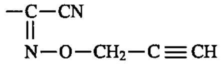 | |
| 2.117 | F | Cl | 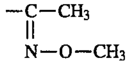 | |
| 2.118 | F | Cl | 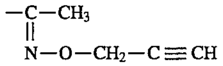 | |
| 2.119 | F | Cl | 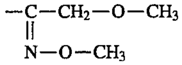 | |
| 2.120 | F | Cl | 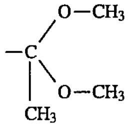 | |
| 2.121 | F | Cl | 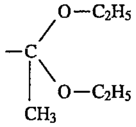 | |
| 2.122 | F | Cl | 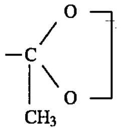 | |
| 2.123 | F | Cl | 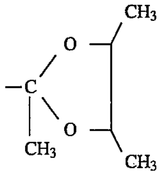 | |
| 2.124 | F | Cl | 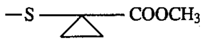 | |
| 2.125 | F | Cl | 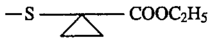 | |

TABLE 2-continued
Compounds of formula Id:
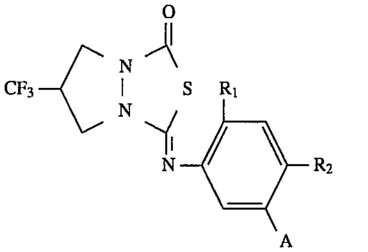
(Id)
| Comp. No. | $R_1$ | $R_2$ | A | Phys. data |
|---|---|---|---|---|
| 2.126 | F | Cl | 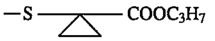 | |
| 2.127 | F | Cl | 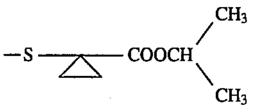 | |
| 2.128 | F | Cl | 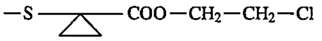 | |
| 2.129 | F | Cl | 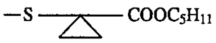 | |
| 2.130 | F | Cl | 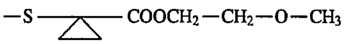 | |
| 2.131 | F | Cl | 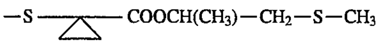 | |
| 2.132 | F | Cl | 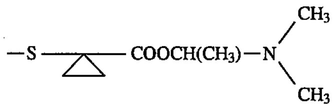 | |
| 2.133 | F | Cl | 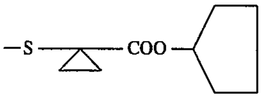 | |
| 2.134 | F | Cl | 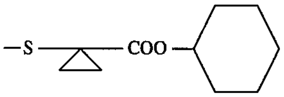 | |
| 2.135 | F | Cl | 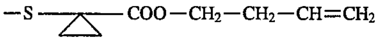 | |
| 2.136 | F | Cl | 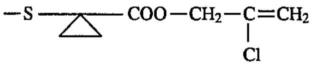 | |
| 2.137 | F | Cl | 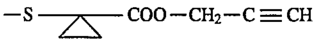 | |
| 2.138 | F | Cl | 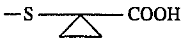 | |
| 2.139 | F | Cl | 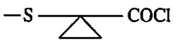 | |
| 2.140 | F | Cl | 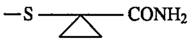 | |
| 2.141 | F | Cl | 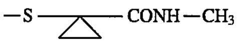 | |
| 2.142 | F | Cl | 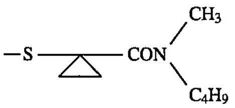 | |

TABLE 2-continued
Compounds of formula Id:
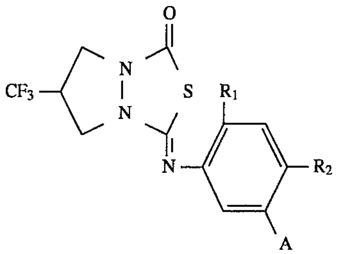
(Id)
| Comp. No. | $R_1$ | $R_2$ | A | Phys. data |
|---|---|---|---|---|
| 2.143 | F | Cl | 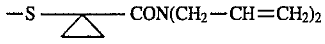 | |
| 2.144 | F | Cl | 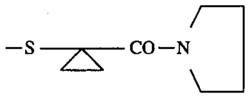 | |
| 2.145 | F | Cl | 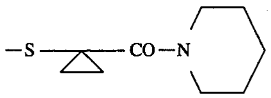 | |
| 2.146 | F | Cl | 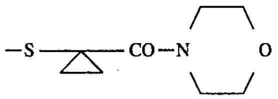 | |
| 2.147 | F | Cl | 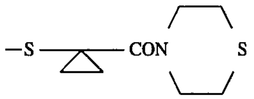 | |
| 2.148 | F | Cl | 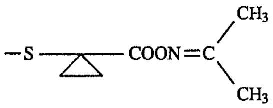 | |
| 2.149 | F | Cl | 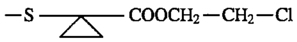 | |
| 2.150 | F | Cl | 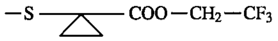 | |
| 2.151 | F | Cl | 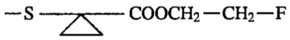 | |
| 2.152 | F | Cl | 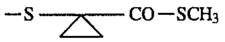 | |
| 2.153 | F | Cl | 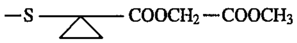 | |
| 2.154 | F | Cl | 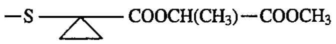 | |
| 2.155 | F | Cl | 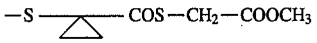 | |
| 2.156 | F | Cl | 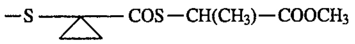 | |
| 2.157 | F | Cl | 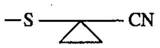 | |
| 2.158 | F | Cl | 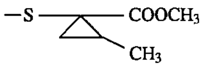 | |
| 2.159 | F | Cl | 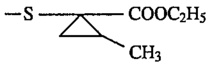 | |

TABLE 2-continued
Compounds of formula Id:
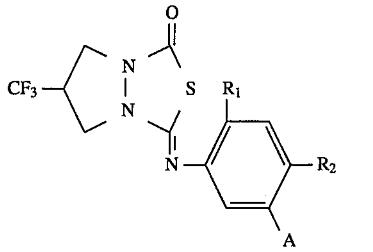
(Id)
| Comp. No. | $R_1$ | $R_2$ | A | Phys. data |
|---|---|---|---|---|
| 2.160 | F | Cl | 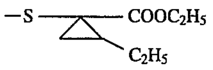 | |
| 2.161 | F | Cl | 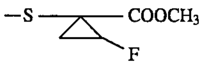 | |
| 2.162 | F | Cl | 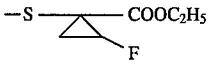 | |
| 2.163 | F | Cl | 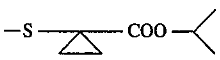 | |
| 2.164 | F | Cl | 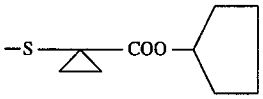 | |
| 2.165 | F | Cl | 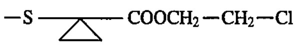 | |
| 2.166 | F | Cl | 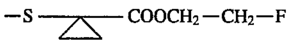 | |
| 2.167 | F | Cl | 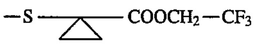 | |
| 2.168 | F | Cl | 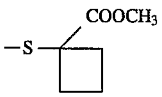 | |
| 2.169 | F | Cl | 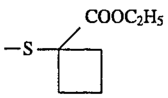 | |
| 2.170 | F | Cl | 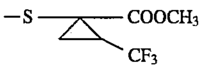 | |
| 2.171 | F | Cl | 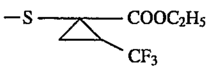 | |
| 2.172 | F | Cl | 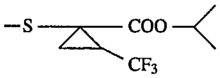 | |
| 2.173 | F | Cl | 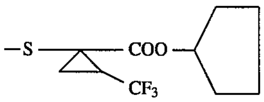 | |
| 2.174 | F | Cl | 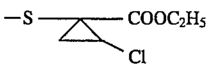 | |

TABLE 2-continued
Compounds of formula Id:
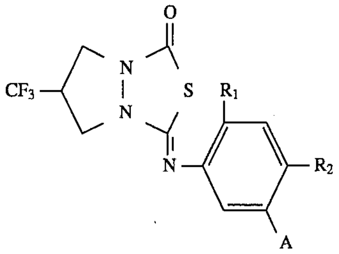
(Id)
| Comp. No. | $R_1$ | $R_2$ | A | Phys. data |
|---|---|---|---|---|
| 2.175 | F | Cl | 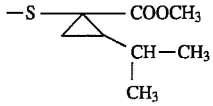 | |
| 2.176 | F | Cl | 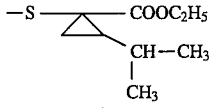 | |
| 2.177 | F | Cl | $-NH-SO_2-CH_3$ | |
| 2.178 | F | Cl | $-NH-SO_2-C_2H_5$ | |
| 2.179 | F | Cl | $-NH-SO_2-Cl$ | |
| 2.180 | F | Cl | 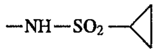 | |
| 2.181 | F | Cl | 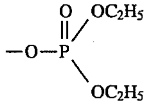 | |
| 2.182 | H | Cl | $-COOH$ | |
| 2.183 | H | Cl | $-COOCH_3$ | |
| 2.184 | H | Cl | 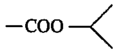 | |
| 2.185 | H | Cl | $-COO-C_5H_{11}$ | |
| 2.186 | H | Cl | $-COO-CH_2-CH_2-O-CH_3$ | |
| 2.187 | H | Cl | $-COOCH_2-S-CH_3$ | |
| 2.188 | H | Cl | $-COOCH-(CH)_3-CH_2-S-CH_3$ | |
| 2.189 | H | Cl | 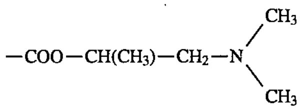 | |
| 2.190 | H | Cl | 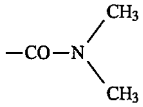 | |
| 2.191 | H | Cl | 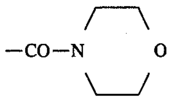 | |
| 2.192 | H | Cl | 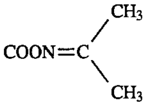 | |
| 2.193 | H | Cl | 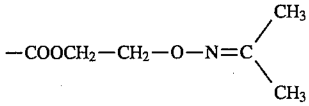 | |

TABLE 2-continued

Compounds of formula Id:

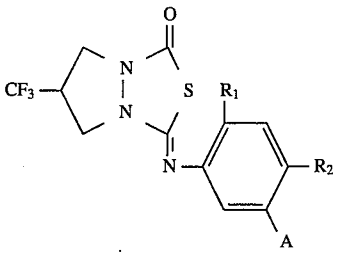

(Id)

| Comp. No. | $R_1$ | $R_2$ | A | Phys. data |
|---|---|---|---|---|
| 2.194 | H | Cl | 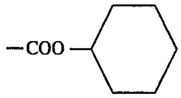 | |
| 2.195 | H | Cl | 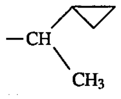 | |
| 2.196 | H | Cl | $-S-C_3H_7$ | |
| 2.197 | H | Cl | $-COOCH_2-COOCH_3$ | |
| 2.198 | H | Cl | $-COOCH(CH_3)-COOCH_3$ | |
| 2.199 | H | Cl | $-COS-CH_2-COOCH_3$ | |
| 2.200 | H | Cl | $-COS-CH(CH_3)-COOCH_3$ | |
| 2.201 | H | Cl | OH | |
| 2.202 | H | Cl | $OCH_3$ | |
| 2.203 | H | Cl | $O-C_2H_5$ | |
| 2.204 | H | Cl | 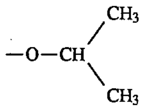 | |
| 2.205 | H | Cl | $-O-CH_2-C\equiv CH$ | |
| 2.206 | H | Cl | $-O-CH_2-CH_2=CHCl$ | |
| 2.207 | H | Cl | 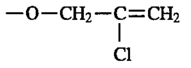 | |
| 2.208 | H | Cl | 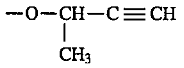 | |
| 2.209 | H | Cl | $-O-CH_2-COOCH_3$ | |
| 2.210 | H | Cl | $-O-CH_2-COOC_2H_{11}$ | |
| 2.211 | H | Cl | $-O-CH(CH_3)-COOCH_3$ | |
| 2.212 | H | Cl | $-SH$ | |
| 2.213 | H | Cl | $-SCH_3$ | |
| 2.214 | H | Cl | $-SC_2H_5$ | |
| 2.215 | H | Cl | 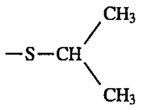 | |
| 2.216 | H | Cl | $-S-CH_2-COOCH_3$ | |
| 2.217 | H | Cl | $-S-CH(CH_3)-COOCH_3$ | |
| 2.218 | H | Cl | $-S-CH_2-COOC_2H_5$ | |
| 2.219 | H | Cl | 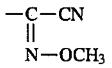 | |

TABLE 2-continued
Compounds of formula Id:
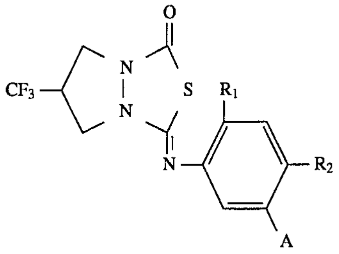
(Id)
| Comp. No. | $R_1$ | $R_2$ | A | Phys. data |
|---|---|---|---|---|
| 2.220 | H | Cl | 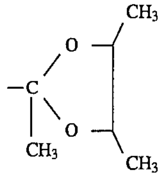 | |
| 2.221 | H | Cl | 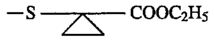 | |
| 2.222 | H | Cl | 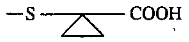 | |
| 2.223 | H | Cl | 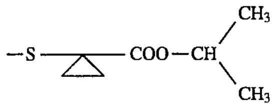 | |
| 2.224 | H | Cl | 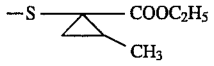 | |
| 2.225 | H | Cl | 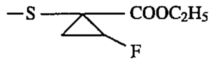 | |
| 2.226 | H | Cl | 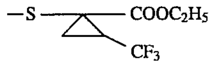 | |
| 2.227 | H | Cl | 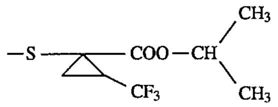 | |
| 2.228 | H | Cl | 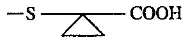 | |
| 2.229 | H | Cl | 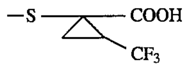 | |
| 2.230 | H | Cl | 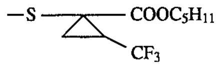 | |
| 2.231 | H | Cl | 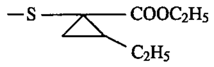 | |
| 2.232 | H | Cl | 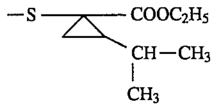 | |
| 2.233 | H | Cl | $-NH-SO_2-C_2H_5$ | |
| 2.234 | H | Cl | $-NH-SO_2-CH_2-Cl$ | |

TABLE 2-continued
Compounds of formula Id:
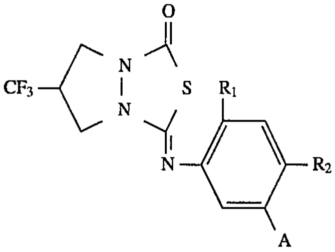
(Id)
| Comp. No. | $R_1$ | $R_2$ | A | Phys. data |
|---|---|---|---|---|
| 2.235 | H | Cl | 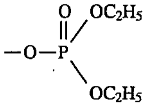 | |
| 2.236 | F | CN | $-COOH$ | |
| 2.237 | F | CN | 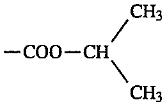 | |
| 2.238 | F | CN | 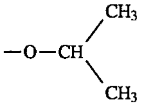 | |
| 2.239 | F | CN | $-O-CH_2-C\equiv CH$ | |
| 2.240 | F | CN | $-O-CH(CH_3)-C\equiv CH$ | |
| 2.241 | F | CN | $-S-CH_2-COOCH_3$ | |
| 2.242 | F | CN | $-S-CH(CH_3)-COOCH_3$ | |
| 2.243 | F | CN | $-O-CH_2-COOCH_3$ | |
| 2.244 | F | CN | $-O-CH_2-COOC_5H_{11}$ | |
| 2.245 | F | CN | $-O-CH(CH_3)-COOC_2H_5$ | |
| 2.246 | F | CN | 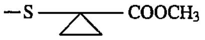 | |
| 2.247 | F | CN | 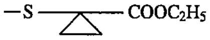 | |
| 2.248 | F | CN | 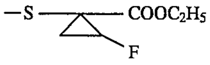 | |
| 2.249 | F | CN | 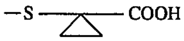 | |
| 2.250 | F | CN | 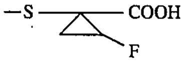 | |
| 2.251 | F | CN | 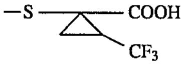 | |
| 2.252 | F | CN | 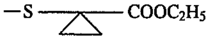 | |
| 2.253 | F | Br | $-COOH$ | |
| 2.254 | F | Br | 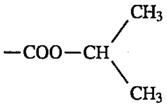 | |
| 2.255 | F | Br | $-OH$ | |

TABLE 2-continued
Compounds of formula Id:
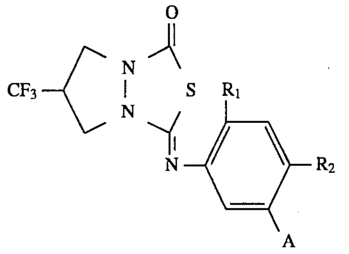
(Id)
| Comp. No. | $R_1$ | $R_2$ | A | Phys. data |
|---|---|---|---|---|
| 2.256 | F | Br | 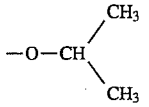 | |
| 2.257 | F | Br | $-O-CH_2-C\equiv CH$ | |
| 2.258 | F | Br | $-O-CH(CH_3)-C\equiv CH$ | |
| 2.259 | F | Br | $-O-CH_2COOCH_3$ | |
| 2.260 | F | Br | $-O-CH_2-COOC_5H_{11}$ | |
| 2.261 | F | Br | $S-CH_2-COOCH_3$ | |
| 2.262 | F | Br | 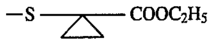 | |
| 2.263 | F | Br | 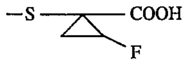 | |
| 2.264 | F | Br | 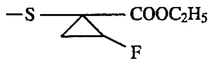 | |
TABLE 3
Compounds of formula Ie:
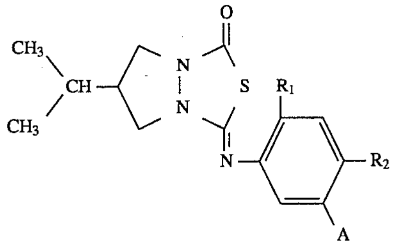
(Ie)
| Comp. No. | $R_1$ | $R_2$ | A | Phys. data |
|---|---|---|---|---|
| 3.001 | F | Cl | $-H$ | |
| 3.002 | F | Cl | $-CN$ | |
| 3.003 | F | Cl | $-NO_2$ | |
| 3.004 | F | Cl | $-COOH$ | |
| 3.005 | F | Cl | $-COOCH_3$ | |
| 3.006 | F | Cl | $-COOC_2H_5$ | |
| 3.007 | F | Cl | $-COOC_3H_7$ | |
| 3.008 | F | Cl | $-COOCH(CH_3)_2$ | |
| 3.009 | F | Cl | $-COOC_4H_9$ | |
| 3.010 | F | Cl | 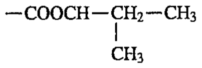 | |

TABLE 3-continued
Compounds of formula Ie:
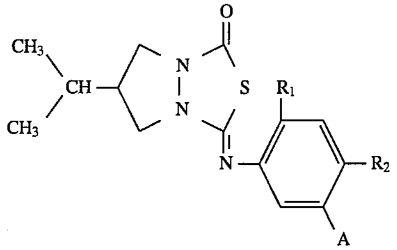
(Ie)
| Comp. No. | $R_1$ | $R_2$ | A | Phys. data |
|---|---|---|---|---|
| 3.011 | F | Cl | 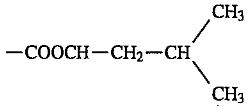 | |
| 3.012 | F | Cl | $-COOC_5H_{11}$ | |
| 3.013 | F | Cl | $-COOCH_2-CH_2-O-CH_3$ | |
| 3.014 | F | Cl | $-COOCH_2-CH_2-O-C_2H_5$ | |
| 3.015 | F | Cl | $-COOCH-(CH_3)-CH_2-OCH_3$ | |
| 3.016 | F | Cl | $-COOCH_2-CH_2-S-CH_3$ | |
| 3.017 | F | Cl | $-COOCH-(CH_3)-CH_2-S-CH_3$ | |
| 3.018 | F | Cl | $COOCH-(CH_3)-CH_2-S-C_2H_5$ | |
| 3.019 | F | Cl | $COOCH-(CH_3)-CH_2-S-C_3H_7$ | |
| 3.020 | F | Cl | 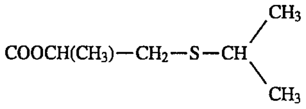 | |
| 3.021 | F | Cl | $COOCH(CH_3)-CH_2-S-C_4H_9$ | |
| 3.022 | F | Cl | $COOCH(CH_3)-CH_2-S-C_5H_{11}$ | |
| 3.023 | F | Cl | 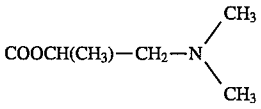 | |
| 3.024 | F | Cl | 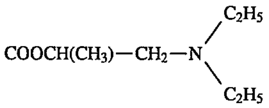 | |
| 3.025 | F | Cl | $-CONH_2$ | |
| 3.026 | F | Cl | $CONH-CH_3$ | |
| 3.027 | F | Cl | 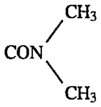 | |
| 3.028 | F | Cl | 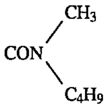 | |
| 3.029 | F | Cl | 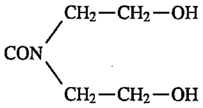 | |
| 3.030 | F | Cl | $CONH-CH_2-CH=CH_2$ | |
| 3.031 | F | Cl | $CON(CH_2-CH=CH_2)$ | |
| 3.032 | F | Cl | 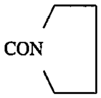 | |

TABLE 3-continued
Compounds of formula Ie:
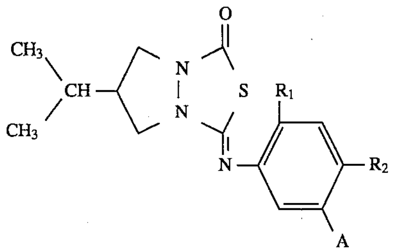
(Ie)
| Comp. No. | $R_1$ | $R_2$ | A | Phys. data |
|---|---|---|---|---|
| 3.033 | F | Cl | 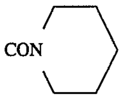 | |
| 3.034 | F | Cl | 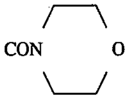 | |
| 3.035 | F | Cl | 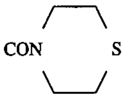 | |
| 3.036 | F | Cl | 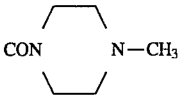 | |
| 3.037 | F | Cl | 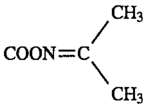 | |
| 3.038 | F | Cl | $COOCH_2-CH_2-Cl$ | |
| 3.039 | F | Cl | $COOCH_2-CN$ | |
| 3.040 | F | Cl | 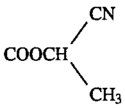 | |
| 3.041 | F | Cl | $COOCH_2-CH_2=CH_2$ | |
| 3.042 | F | Cl | $COOCH_2-CH_2=CHCl$ | |
| 3.043 | F | Cl | 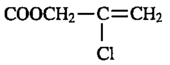 | |
| 3.044 | F | Cl | $COOCH_2-C\equiv CH$ | |
| 3.045 | F | Cl | 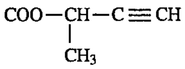 | |
| 3.046 | F | Cl | 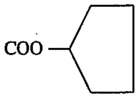 | |
| 3.047 | F | Cl | 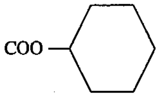 | |

TABLE 3-continued

Compounds of formula Ie:

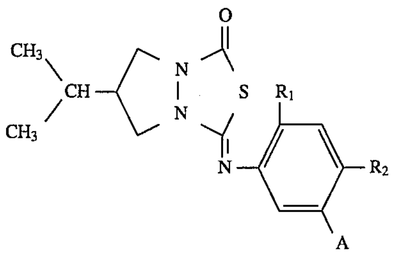

(Ie)

| Comp. No. | $R_1$ | $R_2$ | A | Phys. data |
|---|---|---|---|---|
| 3.048 | F | Cl | 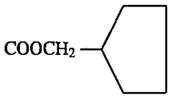 | |
| 3.049 | F | Cl | 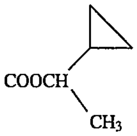 | |
| 3.050 | F | Cl | 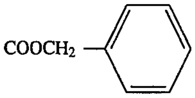 | |
| 3.051 | F | Cl | 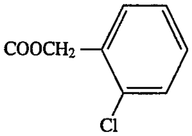 | |
| 3.052 | F | Cl | 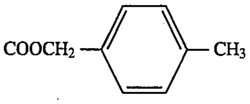 | |
| 3.053 | F | Cl | $COSCH_3$ | |
| 3.054 | F | Cl | $COSC_2H_5$ | |
| 3.055 | F | Cl | $COSC_3H_7$ | |
| 3.056 | F | Cl | $COS-CH_2-CH=CH_2$ | |
| 3.057 | F | Cl | $COS-CH_2-COOCH_3$ | |
| 3.058 | F | Cl | $COS-CH_2-COOC_2H_5$ | |
| 3.059 | F | Cl | $COS-CH_2-COOC_5H_{11}$ | |
| 3.060 | F | Cl | $COS-CH-COOCH_3$<br>$\vert$<br>$CH_3$ | |
| 3.061 | F | Cl | $COS-CH-COOC_2H_5$<br>$\vert$<br>$CH_3$ | |
| 3.062 | F | Cl | $COS-CH-COOC_3H_7$<br>$\vert$<br>$CH_3$ | |
| 3.063 | F | Cl | $COS-CH_2-CH_2-COOCH_3$ | |
| 3.064 | F | Cl | $COS-CH_2-COOCH_2-CH_2-O-CH_3$ | |
| 3.065 | F | Cl | $COOCH_2-COOCH_3$ | |
| 3.066 | F | Cl | $COOCH-COOCH_3$<br>$\vert$<br>$CH_3$ | |
| 3.067 | F | Cl | $COOCH_2-COOC_5H_{11}$ | |
| 3.068 | F | Cl | $COOCH_2-CH_2-Si(CH_3)_3$ | |
| 3.069 | F | Cl | COONa | |

TABLE 3-continued
Compounds of formula Ie:
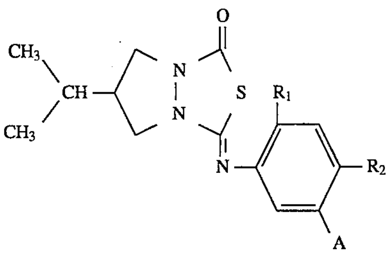
(Ie)
| Comp. No. | $R_1$ | $R_2$ | A | Phys. data |
|---|---|---|---|---|
| 3.070 | F | Cl | 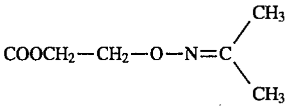 | |
| 3.071 | F | Cl | OH | |
| 3.072 | F | Cl | $OCH_3$ | |
| 3.073 | F | Cl | $OC_2H_5$ | |
| 3.074 | F | Cl | $OC_3H_7$ | |
| 3.075 | F | Cl | 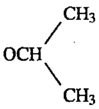 | |
| 3.076 | F | Cl | $OC_4H_9$ | |
| 3.077 | F | Cl | 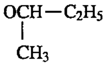 | |
| 3.078 | F | Cl | 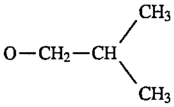 | |
| 3.079 | F | Cl | $OCH_2CH{=}CH_2$ | |
| 3.080 | F | Cl | 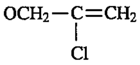 | |
| 3.081 | F | Cl | $OCH_2CH{=}CHCl$ | |
| 3.082 | F | Cl | $OCH_2C{\equiv}CH$ | |
| 3.083 | F | Cl | 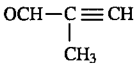 | |
| 3.084 | F | Cl | $-OCH_2-COOCH_3$ | |
| 3.085 | F | Cl | $-O-CH_2-COOC_5H_{11}$ | |
| 3.086 | F | Cl | 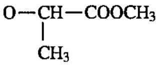 | |
| 3.087 | F | Cl | $O-CH_2-COOC_2H_5$ | |
| 3.088 | F | Cl | 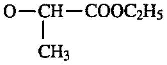 | |
| 3.089 | F | Cl | $O-CH_2-CH_2-O-CH_3$ | |
| 3.090 | F | Cl | 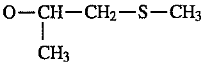 | |

TABLE 3-continued

Compounds of formula Ie:

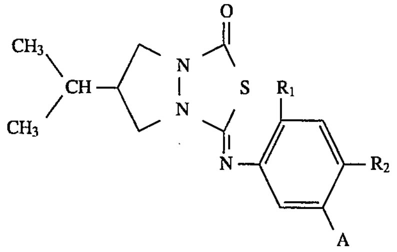

(Ie)

| Comp. No. | $R_1$ | $R_2$ | A | Phys. data |
|---|---|---|---|---|
| 3.091 | F | Cl | $O-CH-CH_2-S-C_2H_5$<br>\|<br>$CH_3$ | |
| 3.092 | F | Cl | $O-CH-CH_2-S-C_3H_7$<br>\|<br>$CH_3$ | |
| 3.093 | F | Cl | $O-CH_2-CH_2-Cl$ | |
| 3.094 | F | Cl | $O-CH_2-CN$ | |
| 3.095 | F | Cl | $O-CH-CN$<br>\|<br>$CH_3$ | |
| 3.096 | F | Cl | $S-CH_3$ | |
| 3.097 | F | Cl | $S-C_2H_5$ | |
| 3.098 | F | Cl | $S-C_3H_7$ | |
| 3.099 | F | Cl | 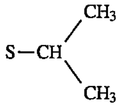 | |
| 3.100 | F | Cl | $S-CH_2-CH=CH_2$ | |
| 3.101 | F | Cl | $S-CH_2-C=CH_2$<br>\|<br>Cl | |
| 3.102 | F | Cl | $S-CH_2-CH=CHCl$ | |
| 3.103 | F | Cl | $S-CH_2-C\equiv CH$ | |
| 3.104 | F | Cl | $S-CH-C\equiv CH$<br>\|<br>$CH_3$ | |
| 3.105 | F | Cl | $S-CH_2-COOCH_3$ | |
| 3.106 | F | Cl | $S-CH_2-COOC_2H_5$ | |
| 3.107 | F | Cl | $S-CH_2-COOC_5H_{11}$ | |
| 3.108 | F | Cl | $S-CH-COOCH_3$<br>\|<br>$CH_3$ | |
| 3.109 | F | Cl | $S-CH-COOC_2H_5$<br>\|<br>$CH_3$ | |
| 3.110 | F | Cl | $S-CH_2-COOCH_2-CH_2-O-CH_3$ | |
| 3.111 | F | Cl | 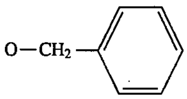 | |
| 3.112 | F | Cl | 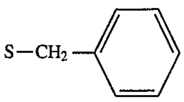 | |

TABLE 3-continued
Compounds of formula Ie:
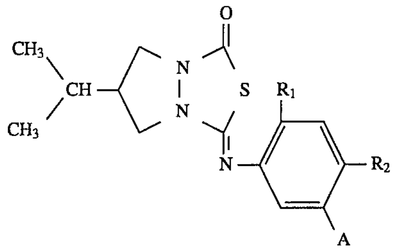
(Ie)
| Comp. No. | $R_1$ | $R_2$ | A | Phys. data |
|---|---|---|---|---|
| 3.114 | F | Cl | 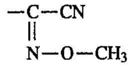 | |
| 3.115 | F | Cl | 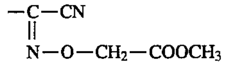 | |
| 3.116 | F | Cl | 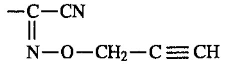 | |
| 3.117 | F | Cl | 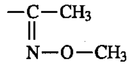 | |
| 3.118 | F | Cl | 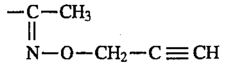 | |
| 3.119 | F | Cl | 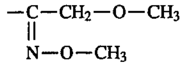 | |
| 3.120 | F | Cl | 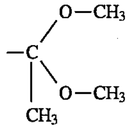 | |
| 3.121 | F | Cl | 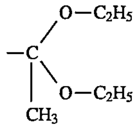 | |
| 3.122 | F | Cl | 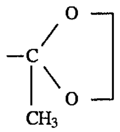 | |
| 3.123 | F | Cl | 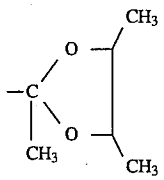 | |
| 3.124 | F | Cl | 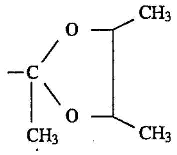 | |
| 3.125 | F | Cl | 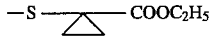 | |

TABLE 3-continued
Compounds of formula Ie:
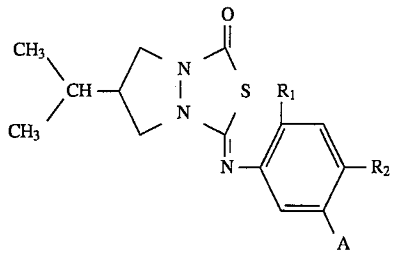
(Ie)
| Comp. No. | $R_1$ | $R_2$ | A | Phys. data |
| --- | --- | --- | --- | --- |
| 3.126 | F | Cl | 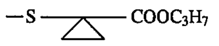 | |
| 3.127 | F | Cl | 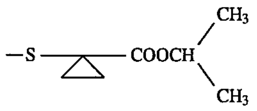 | |
| 3.128 | F | Cl | 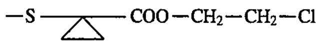 | |
| 3.129 | F | Cl | 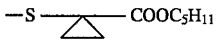 | |
| 3.130 | F | Cl | 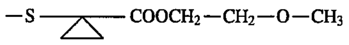 | |
| 3.131 | F | Cl | 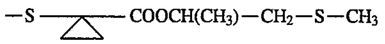 | |
| 3.132 | F | Cl | 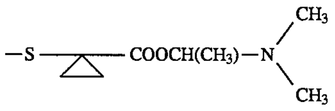 | |
| 3.133 | F | Cl | 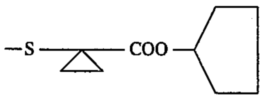 | |
| 3.134 | F | Cl | 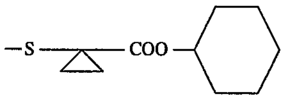 | |
| 3.135 | F | Cl | 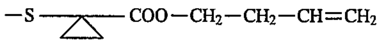 | |
| 3.136 | F | Cl | 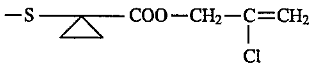 | |
| 3.137 | F | Cl | 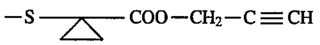 | |
| 3.138 | F | Cl | 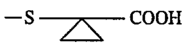 | |
| 3.139 | F | Cl | 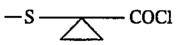 | |
| 3.140 | F | Cl | 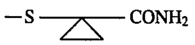 | |
| 3.141 | F | Cl | 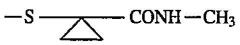 | |
| 3.142 | F | Cl | 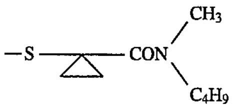 | |

TABLE 3-continued
Compounds of formula Ie:
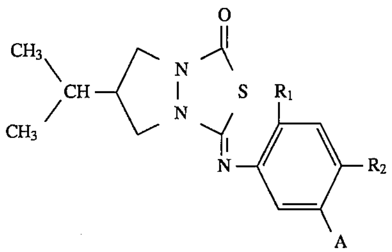
(Ie)
| Comp. No. | $R_1$ | $R_2$ | A | Phys. data |
|---|---|---|---|---|
| 3.143 | F | Cl | 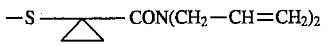 | |
| 3.144 | F | Cl | 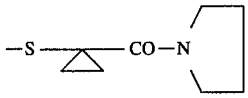 | |
| 3.145 | F | Cl | 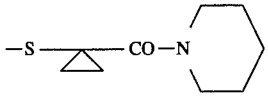 | |
| 3.146 | F | Cl | 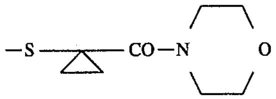 | |
| 3.147 | F | Cl | 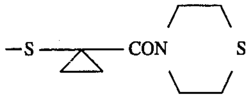 | |
| 3.148 | F | Cl | 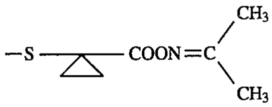 | |
| 3.149 | F | Cl | 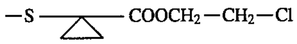 | |
| 3.150 | F | Cl | 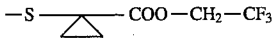 | |
| 3.151 | F | Cl | 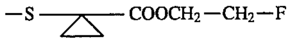 | |
| 3.152 | F | Cl | 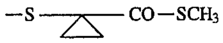 | |
| 3.153 | F | Cl | 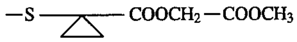 | |
| 3.154 | F | Cl | 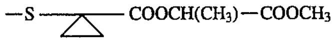 | |
| 3.155 | F | Cl | 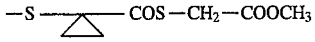 | |
| 3.156 | F | Cl | 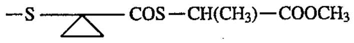 | |
| 3.157 | F | Cl | 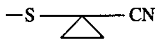 | |
| 3.158 | F | Cl | 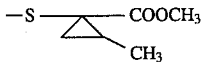 | |
| 3.159 | F | Cl | 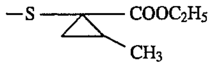 | |

TABLE 3-continued
Compounds of formula Ie:
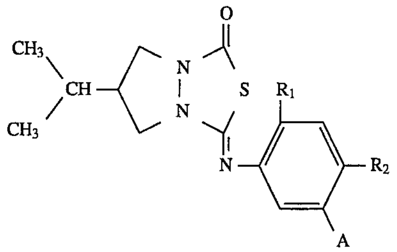
(Ie)
| Comp. No. | $R_1$ | $R_2$ | A | Phys. data |
|---|---|---|---|---|
| 3.160 | F | Cl | 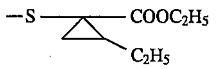 | |
| 3.161 | F | Cl | 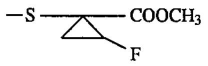 | |
| 3.162 | F | Cl | 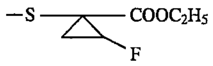 | |
| 3.163 | F | Cl | 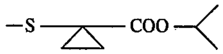 | |
| 3.164 | F | Cl | 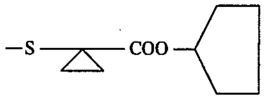 | |
| 3.165 | F | Cl | 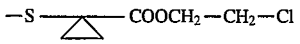 | |
| 3.166 | F | Cl | 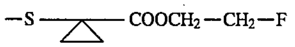 | |
| 3.167 | F | Cl | 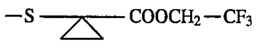 | |
| 3.168 | F | Cl | 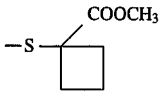 | |
| 3.169 | F | Cl | 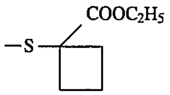 | |
| 3.170 | F | Cl | 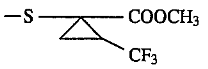 | |
| 3.171 | F | Cl | 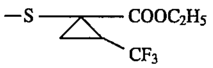 | |
| 3.172 | F | Cl | 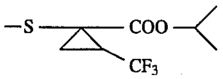 | |
| 3.173 | F | Cl | 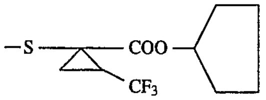 | |
| 3.174 | F | Cl | 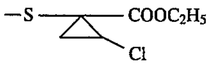 | |

TABLE 3-continued
Compounds of formula Ie:
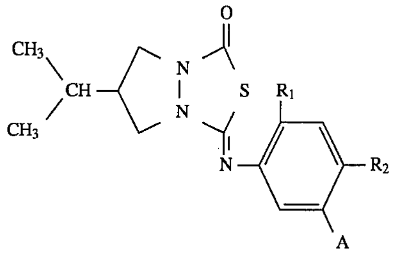
(Ie)
| Comp. No. | $R_1$ | $R_2$ | A | Phys. data |
|---|---|---|---|---|
| 3.175 | F | Cl | 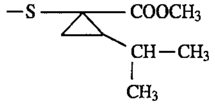 | |
| 3.176 | F | Cl | 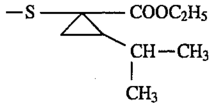 | |
| 3.177 | F | Cl | $-NH-SO_2-CH_3$ | |
| 3.178 | F | Cl | $-NH-SO_2-C_2H_5$ | |
| 3.179 | F | Cl | $-NH-SO_2-Cl$ | |
| 3.180 | F | Cl | 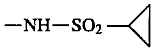 | |
| 3.181 | F | Cl | 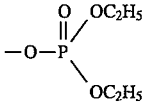 | |
| 3.182 | H | Cl | $-COOH$ | |
| 3.183 | H | Cl | $-COOCH_3$ | |
| 3.184 | H | Cl | 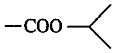 | |
| 3.185 | H | Cl | $-COO-C_5H_{11}$ | |
| 3.186 | H | Cl | $-COO-CH_2-CH_2-O-CH_3$ | |
| 3.187 | H | Cl | $-COOCH_2-S-CH_3$ | |
| 3.188 | H | Cl | $-COOCH-(CH)_3-CH_2-S-CH_3$ | |
| 3.189 | H | Cl | 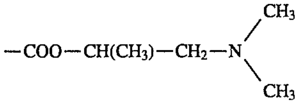 | |
| 3.190 | H | Cl | 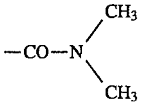 | |
| 3.191 | H | Cl | 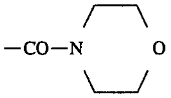 | |
| 3.192 | H | Cl | 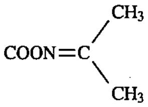 | |
| 3.193 | H | Cl | 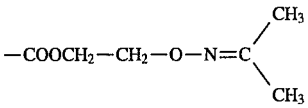 | |

TABLE 3-continued

Compounds of formula Ie:

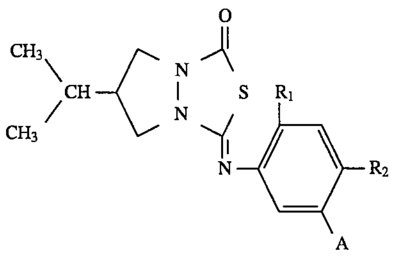

(Ie)

| Comp. No. | $R_1$ | $R_2$ | A | Phys. data |
|---|---|---|---|---|
| 3.194 | H | Cl | 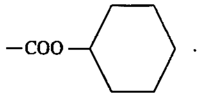 | |
| 3.195 | H | Cl | 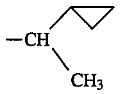 | |
| 3.196 | H | Cl | $-S-C_3H_7$ | |
| 3.197 | H | Cl | $-COOCH_2-COOCH_3$ | |
| 3.198 | H | Cl | $-COOCH(CH_3)-COOCH_3$ | |
| 3.199 | H | Cl | $-COS-CH_2-COOCH_3$ | |
| 3.200 | H | Cl | $-COS-CH(CH_3)-COOCH_3$ | |
| 3.201 | H | Cl | OH | |
| 3.202 | H | Cl | $OCH_3$ | |
| 3.203 | H | Cl | $O-C_2H_5$ | |
| 3.204 | H | Cl | 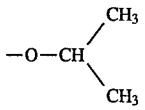 | |
| 3.205 | H | Cl | $-O-CH_2-C\equiv CH$ | |
| 3.206 | H | Cl | $-O-CH_2-CH_2=CHCl$ | |
| 3.207 | H | Cl | 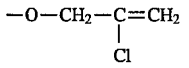 | |
| 3.208 | H | Cl | 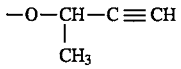 | |
| 3.209 | H | Cl | $-O-CH_2-COOCH_3$ | |
| 3.210 | H | Cl | $-O-CH_2-COOC_2H_{11}$ | |
| 3.211 | H | Cl | $-O-CH(CH_3)-COOCH_3$ | |
| 3.212 | H | Cl | $-SH$ | |
| 3.213 | H | Cl | $-SCH_3$ | |
| 3.214 | H | Cl | $-SC_2H_5$ | |
| 3.215 | H | Cl | 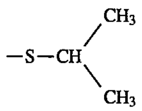 | |
| 3.216 | H | Cl | $-S-CH_2-COOCH_3$ | |
| 3.217 | H | Cl | $-S-CH(CH_3)-COOCH_3$ | |
| 3.218 | H | Cl | $-S-CH_2-COOC_2H_5$ | |
| 3.219 | H | Cl | 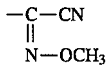 | |

TABLE 3-continued
Compounds of formula Ie:
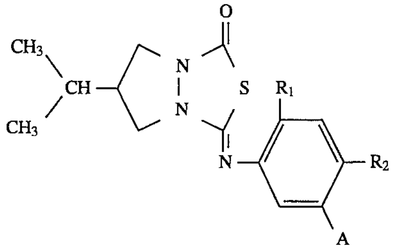
(Ie)
| Comp. No. | $R_1$ | $R_2$ | A | Phys. data |
|---|---|---|---|---|
| 3.220 | H | Cl | 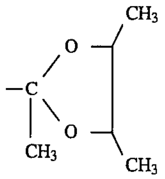 | |
| 3.221 | H | Cl | 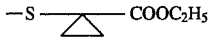 | |
| 3.222 | H | Cl | 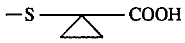 | |
| 3.223 | H | Cl | 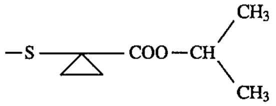 | |
| 3.224 | H | Cl | 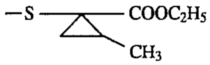 | |
| 3.225 | H | Cl | 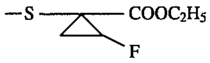 | |
| 3.226 | H | Cl | 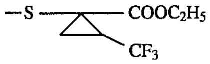 | |
| 3.227 | H | Cl | 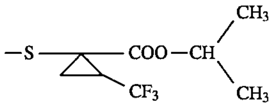 | |
| 3.228 | H | Cl | 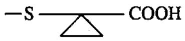 | |
| 3.229 | H | Cl | 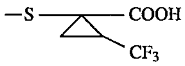 | |
| 3.230 | H | Cl | 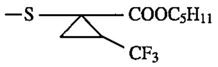 | |
| 3.231 | H | Cl | 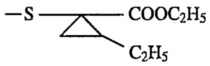 | |
| 3.232 | H | Cl | 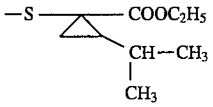 | |
| 3.233 | H | Cl | $-NH-SO_2-C_2H_5$ | |
| 3.234 | H | Cl | $-NH-SO_2-CH_2-Cl$ | |

TABLE 3-continued
Compounds of formula Ie:
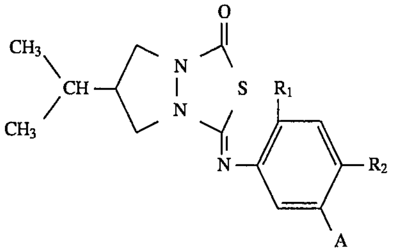
(Ie)
| Comp. No. | $R_1$ | $R_2$ | A | Phys. data |
|---|---|---|---|---|
| 3.235 | H | Cl | 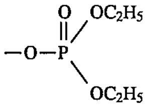 | |
| 3.236 | F | CN | $-COOH$ | |
| 3.237 | F | CN | 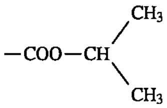 | |
| 3.238 | F | CN | 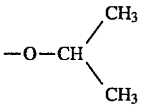 | |
| 3.239 | F | CN | $-O-CH_2-C{\equiv}CH$ | |
| 3.240 | F | CN | $-O-CH(CH_3)-C{\equiv}CH$ | |
| 3.241 | F | CN | $-S-CH_2-COOCH_3$ | |
| 3.242 | F | CN | $-S-CH(CH_3)-COOCH_3$ | |
| 3.243 | F | CN | $-O-CH_2-COOCH_3$ | |
| 3.244 | F | CN | $-O-CH_2-COOC_5H_{11}$ | |
| 3.245 | F | CN | $-O-CH(CH_3)-COOC_2H_5$ | |
| 3.246 | F | CN | 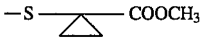 | |
| 3.247 | F | CN | 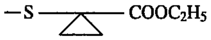 | |
| 3.248 | F | CN | 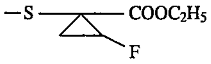 | |
| 3.249 | F | CN | 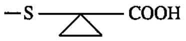 | |
| 3.250 | F | CN | 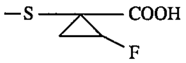 | |
| 3.251 | F | CN | 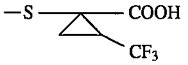 | |
| 3.252 | F | CN | 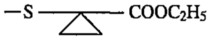 | |
| 3.253 | F | Br | $-COOH$ | |
| 3.254 | F | Br | 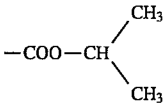 | |
| 3.255 | F | Br | $-OH$ | |

TABLE 3-continued

Compounds of formula Ie:

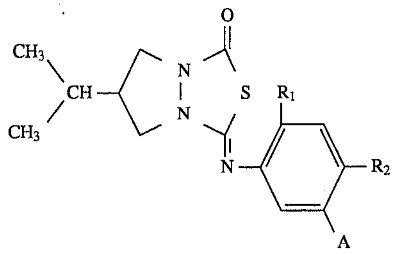

(Ie)

| Comp. No. | $R_1$ | $R_2$ | A | Phys. data |
|---|---|---|---|---|
| 3.256 | F | Br | 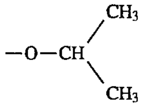 | |
| 3.257 | F | Br | $-O-CH_2-C\equiv CH$ | |
| 3.258 | F | Br | $-O-CH(CH_3)-C\equiv CH$ | |
| 3.259 | F | Br | $-O-CH_2COOCH_3$ | |
| 3.260 | F | Br | $-O-CH_2-COOC_5H_{11}$ | |
| 3.261 | F | Br | $S-CH_2-COOCH_3$ | |
| 3.262 | F | Br | 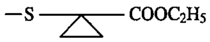 | |
| 3.263 | F | Br | 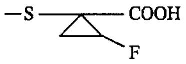 | |
| 3.264 | F | Br | 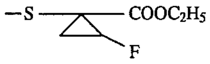 | |

TABLE 4

Compounds of formula If:

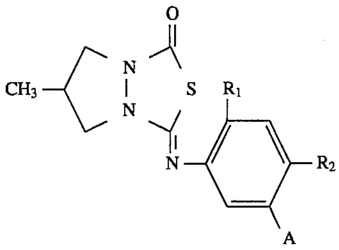

(If)

| Comp. No. | $R_1$ | $R_2$ | A | Phys. data |
|---|---|---|---|---|
| 4.01 | F | Cl | OH | |
| 4.02 | F | Cl | 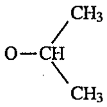 | (resin) |
| 4.03 | F | Cl | $O-CH_2-C\equiv CH$ | |
| 4.04 | F | Cl | 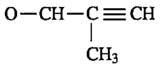 | |
| 4.05 | F | Cl | $S-CH_2-COOC_2H_5$ | (oil) |

TABLE 4-continued

Compounds of formula If:

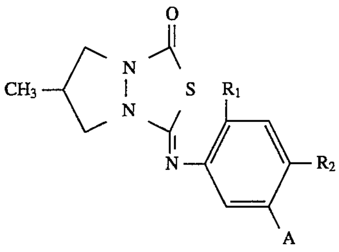

(If)

| Comp. No. | $R_1$ | $R_2$ | A | Phys. data |
|---|---|---|---|---|
| 4.06 | F | Cl | $O-CH_2-COOCH_3$ | |
| 4.07 | F | Cl | $S-CH(CH_3)COOCH_3$ | |
| 4.08 | F | Cl | $-OCH(CH_3)COOCH_3$ | |
| 4.09 | F | Cl | $-COOH$ | |
| 4.10 | F | Cl | 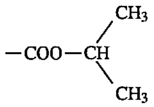 | |
| 4.11 | F | Cl | 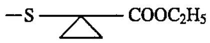 | |

TABLE 4-continued
Compounds of formula If:
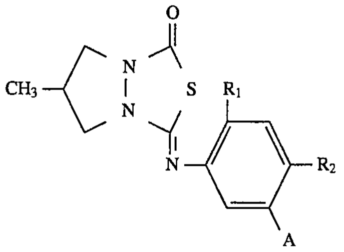
(If)
| Comp. No. | $R_1$ | $R_2$ | A | Phys. data |
|---|---|---|---|---|
| 4.12 | F | Cl | 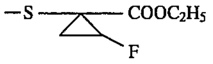 | |
| 4.13 | F | Cl | 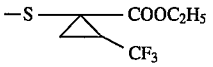 | |
| 4.14 | H | Cl | $-S-CH_2-COOCH_3$ | |
TABLE 5
Compounds of formula Ig
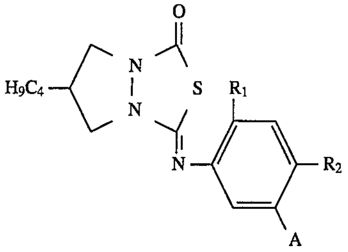
(Ig)
| Comp. No. | $R_1$ | $R_2$ | A | Phys. data |
|---|---|---|---|---|
| 5.01 | F | Cl | OH | |
| 5.02 | F | Cl | 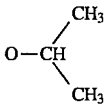 | |
TABLE 5-continued
Compounds of formula Ig
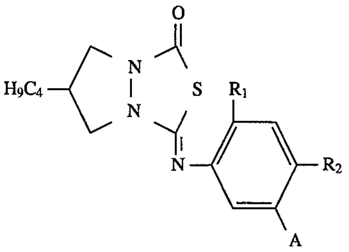
(Ig)
| Comp. No. | $R_1$ | $R_2$ | A | Phys. data |
|---|---|---|---|---|
| 5.03 | F | Cl | $O-CH_2-C\equiv CH$ | |
| 5.04 | F | Cl | 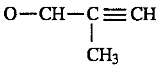 | |
| 5.05 | F | Cl | $S-CH_2-COOC_2H_5$ | |
| 5.06 | F | Cl | $O-CH_2-COOCH_3$ | |
| 5.07 | F | Cl | $S-CH(CH_3)COOCH_3$ | |
| 5.08 | F | Cl | $-OCH(CH_3)COOCH_3$ | |
| 5.09 | F | Cl | $-COOH$ | |
| 5.10 | F | Cl | 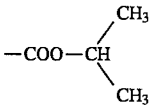 | |
| 5.11 | F | Cl | 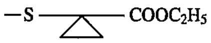 | |
| 5.12 | F | Cl | 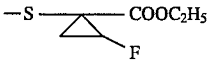 | |
| 5.13 | F | Cl | 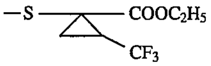 | |
| 5.14 | H | Cl | $-S-CH_2-COOCH_3$ | |

TABLE 6
Compounds of formula Ih
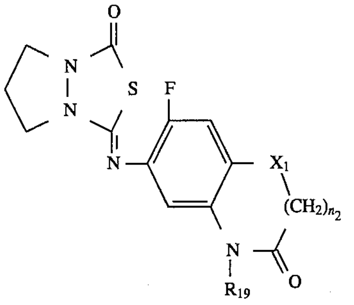
(Ih)
| Comp. No. | $X_1$ | $R_{19}$ | $n_2$ | Phys. data |
|---|---|---|---|---|
| 6.01 | O | H | 0 | |
| 6.02 | O | H | 1 | |
| 6.03 | O | $CH_3$ | 0 | |
| 6.04 | O | $C_2H_5$ | 0 | |
| 6.05 | O | $C_2H_5$ | 1 | |
| 6.06 | O | 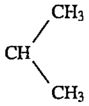 | 0 | |
| 6.07 | O | 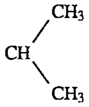 | 1 | |
| 6.08 | O | $CH_2-C\equiv CH$ | 0 | |
| 6.09 | O | $CH_2-C\equiv CH$ | 1 | m.p. 176–177° C. |
| 6.10 | O | H | 0 | |
| 6.11 | O | H | 1 | |
| 6.12 | O | $CH_3$ | 0 | |
| 6.13 | O | $C_2H_5$ | 0 | |
| 6.14 | O | $C_2H_5$ | 1 | |
| 6.15 | O | 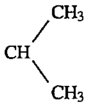 | 0 | |
| 6.16 | O | 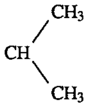 | 1 | |
| 6.17 | O | $CH_2-C\equiv CH$ | 0 | |
| 6.18 | O | $CH_2-C\equiv CH$ | 1 | |
| 6.19 | S | H | 0 | |
| 6.20 | S | $CH_3$ | 0 | |
| 6.21 | S | $C_2H_5$ | 0 | |
| 6.22 | S | $C_3H_7(n)$ | 0 | |
| 6.23 | S | 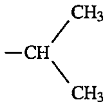 | 0 | m.p. 187–188° C. |
| 6.24 | S | $-C_4H_9(n)$ | 0 | |
| 6.25 | S | $-C_4H_9(S)$ | 0 | |
| 6.26 | S | $-C_4H_9(i)$ | 0 | |
| 6.27 | S | $-C_4H_9(t)$ | 0 | |
| 6.28 | S | $-CH_2-CH=CH$ | 0 | |
| 6.29 | S | $-CH_2-CH=CH_2-CH_3$ | 0 | |

TABLE 6-continued

Compounds of formula Ih

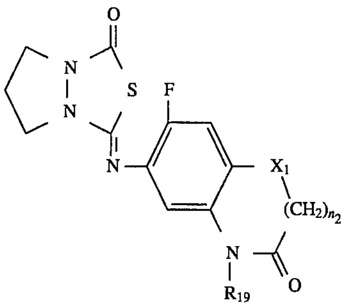

(Ih)

| Comp. No. | $X_1$ | $R_{19}$ | $n_2$ | Phys. data |
|---|---|---|---|---|
| 6.30 | S | $-CH_2-C(CH_3)=CH_2$ | 0 | |
| 6.31 | S | $-CH_2-C\equiv CH$ | 0 | |
| 6.32 | S | $-CH_2-C\equiv C-CH_3$ | 0 | |
| 6.33 | S | $-CH(CH_3)-C\equiv CH$ | 0 | |
| 6.34 | S | $-CH_2-C(Cl)=CHCl$ | 0 | |
| 6.35 | S | $-CH_2-C(Cl)=CH_2$ | 0 | |
| 6.36 | S | $-CH_2-CH=CHCl$ | 0 | |
| 6.37 | S | $-CH_2-CH=C(Cl)-CH_3$ | 0 | |
| 6.38 | S | $-CH_2-CH=CH-Br$ | 0 | |
| 6.39 | S | $-CH_2-C(Br)=CH-Br$ | 0 | |
| 6.40 | S | $-CH_2-C(Br)=CH_2$ | 0 | |
| 6.41 | S | $-CH_2-O-CH_3$ | 0 | |
| 6.42 | S | $-CH_2-O-C_3H_7$ | 0 | |
| 6.43 | S | $-CH_2-O-C_4H_9$ | 0 | |
| 6.44 | S | $-CH_2-CH_2-O-CH_3$ | 0 | |
| 6.45 | S | $-CH_2-CH_2-O-C_2H_5$ | 0 | |
| 6.46 | S | $-CH_2-CN$ | 0 | |
| 6.47 | S | $-CH_2-CH_2-CN$ | 0 | |
| 6.48 | S | $-C(CH_3)-CN$ | 0 | |
| 6.49 | S | $-CH_2-COOCH_3$ | 0 | |
| 6.50 | S | $-CH_2-COOC_2H_5$ | 0 | |
| 6.51 | S | $-CH_2-COO-CH(CH_3)_2$ | 0 | |
| 6.52 | S | $-CH_2-COOC_5H_{11}$ | 0 | |
| 6.53 | S | $-CH_2-CH_2-COOCH_3$ | 0 | |
| 6.54 | S | $-CH_2-CH_2-COOC_2H_5$ | 0 | |

TABLE 6-continued
Compounds of formula Ih
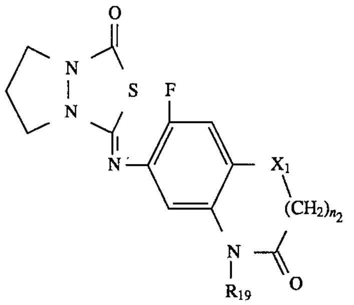
(Ih)
| Comp. No. | $X_1$ | $R_{19}$ | $n_2$ | Phys. data |
|---|---|---|---|---|
| 6.55 | S | 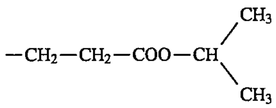 | 0 | |
| 6.56 | S | 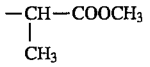 | 0 | |
| 6.57 | S | 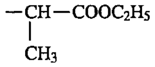 | 0 | m.p. 154–156° C. |
| 6.58 | S | 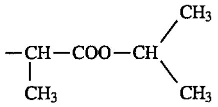 | 0 | |
| 6.59 | S | 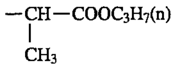 | 0 | |
| 6.60 | S | 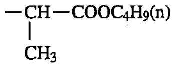 | 0 | |
| 6.61 | S | 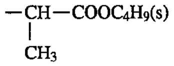 | 0 | |
| 6.62 | S | 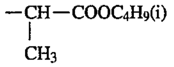 | 0 | |
| 6.63 | S | 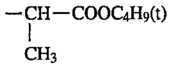 | 0 | |
| 6.64 | S | 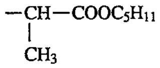 | 0 | |
| 6.65 | S | 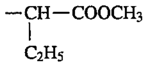 | 0 | |
| 6.66 | S | 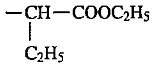 | 0 | |
| 6.67 | S | 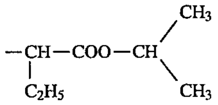 | 0 | |
| 6.68 | S | 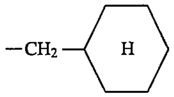 | 0 | |

TABLE 6-continued
Compounds of formula Ih
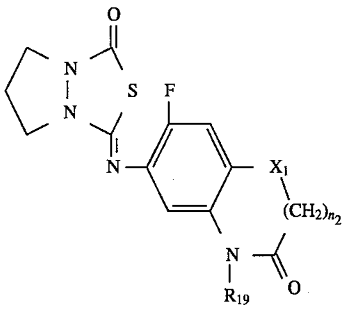
(Ih)
| Comp. No. | $X_1$ | $R_{19}$ | $n_2$ | Phys. data |
|---|---|---|---|---|
| 6.69 | S | 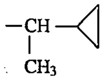 | 0 | |
| 6.70 | S | 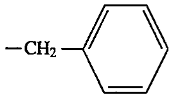 | 0 | |
| 6.71 | S | 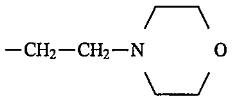 | 0 | |
| 6.72 | S | 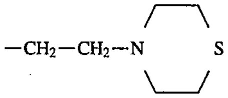 | 0 | |
| 6.73 | S | 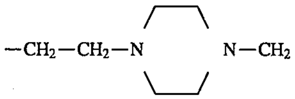 | 0 | |
| 6.74 | S | 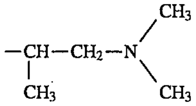 | 0 | |
| 6.75 | S | 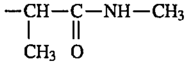 | 0 | |
| 6.76 | S | 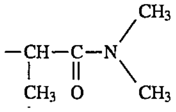 | 0 | |
| 6.77 | S | 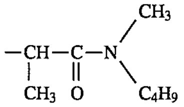 | 0 | |
| 6.78 | S | $FCH_2-$ | 0 | |
| 6.79 | S | $F_2CH-$ | 0 | |
| 6.80 | S | $FCH_2-CH_2-$ | 0 | |
| 6.81 | S | $CF_3-CH_2-$ | 0 | |
| 6.82 | S | $FCH_2-CH_2-CH_2-$ | 0 | |
| 6.83 | S | $Cl-CH_2-$ | 0 | |
| 6.84 | S | $Br-CH_2-$ | 0 | |
| 6.85 | S | $Cl_3C-$ | 0 | |
| 6.86 | S | $F_3C-$ | 0 | |
| 6.87 | S | $Cl-CH_2-CH_2-$ | 0 | |
| 6.88 | S | $Br-CH_2-CH_2-$ | 0 | |
| 6.89 | S | $CF_3-CF_2-$ | 0 | |
| 6.90 | S | $IC\equiv C-CH_2-$ | 0 | |

TABLE 6-continued

Compounds of formula Ih

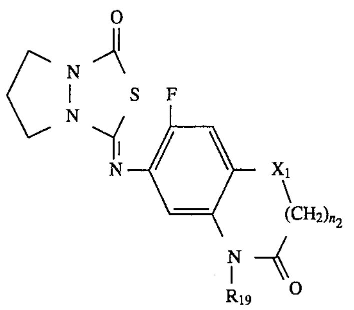

(Ih)

| Comp. No. | $X_1$ | $R_{19}$ | $n_2$ | Phys. data |
|---|---|---|---|---|
| 6.91 | S | $CH_3-O-CH_2-O-CH_2-$ | 0 | |
| 6.92 | S | $CH_3-O-CH_2-CH_2-O-CH_2-$ | 0 | |
| 6.93 | S | $C_2H_5-O-CH_2-O-CH_2-$ | 0 | |
| 6.94 | S | $CH_3-O-CH_2-O-CH_2-CH_2-$ | 0 | |
| 6.95 | S | $C_2H_5-O-CH_2-O-CH_2-CH_2-$ | 0 | |
| 6.96 | S | $C_2H_5-O-CH_2-CH_2-O-CH_2-$ | 0 | |
| 6.97 | S | $C_2H_5-O-CH_2-CH_2-O-CH_2-CH_2-$ | 0 | |
| 6.98 | S | $C_6H_5-CH=CH-CH_2-$ | 0 | |
| 6.99 | S | $-CH_2-COOH$ | 0 | |
| 6.100 | S | $-CH-COOH$<br>$CH_3$ | 0 | |
| 6.101 | S | $-CH-COOH$<br>$C_2H_5$ | 0 | |
| 6.102 | S | $-CH_2-CH_2-COOH$ | 0 | |
| 6.103 | S | O<br>$Cl-CH_2-CH_2-O-C-CH_2$ | 0 | |
| 6.104 | S | $F-CH_2-CH_2-O-C-CH_2-$<br>O | 0 | |
| 6.105 | S | $F-CH_2-CH_2-CH_2-O-C-CH_2-$<br>O | 0 | |
| 6.106 | S | $F_3-C_2-CH_2-O-C-CH_2-$<br>O | 0 | |
| 6.107 | S | $Cl-CH_2-CH_2-O-C-CH-$<br>O $CH_3$ | 0 | |
| 6.108 | S | $F-CH_2-CH_2-O-C-CH-$<br>O $CH_3$ | 0 | |
| 6.109 | S | $F-CH_2-CH_2-CH_2-O-C-CH-$<br>O $CH_3$ | 0 | |
| 6.110 | S | $CF_3-CH_2-O-C-CH$<br>O $CH_3$ | 0 | |
| 6.111 | S | $CH_3-O-CH_2-CH_2-O-C-CH_2$<br>O | 0 | |
| 6.112 | S | $C_2H_5-O-CH_2-CH_2-O-C-CH_2-$<br>O | 0 | |
| 6.113 | S | $C_3H_7-O-CH_2-CH_2-O-C-CH_2-$<br>O | 0 | |

TABLE 6-continued
Compounds of formula Ih
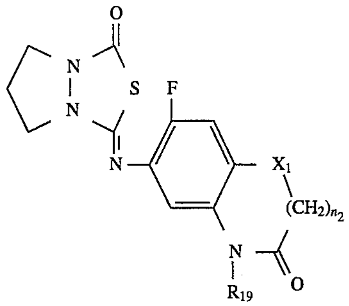
(Ih)
| Comp. No. | $X_1$ | $R_{19}$ | $n_2$ | Phys. data |
|---|---|---|---|---|
| 6.114 | S | 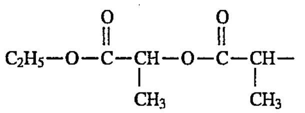 | 0 | |
| 6.115 | S | 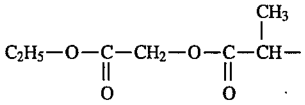 | 0 | |
| 6.116 | S | 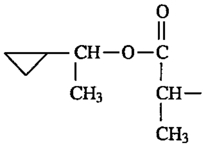 | 0 | |
| 6.117 | S | 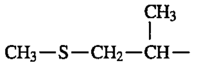 | 0 | |
| 6.118 | S | 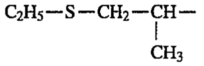 | 0 | |
| 6.119 | S | $CH_3-S-CH_2-CH_2$ | 0 | |
| 6.120 | S | 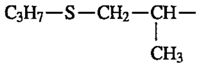 | 0 | |
| 6.121 | S | 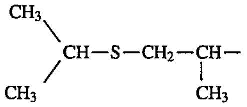 | 0 | |
| 6.122 | S | 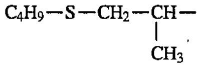 | 0 | |
| 6.123 | S | 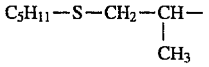 | 0 | |
| 6.124 | S | $CH_3-SO_2-$ | 0 | |
| 6.125 | S | $C_2H_5SO_2-$ | 0 | |
| 6.126 | S | $CH_2=CH-CH_2-O-CH_2-$ | 0 | |
| 6.127 | S | 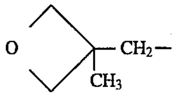 | 0 | |
| 6.128 | S | 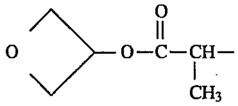 | 0 | |

TABLE 6-continued
Compounds of formula Ih
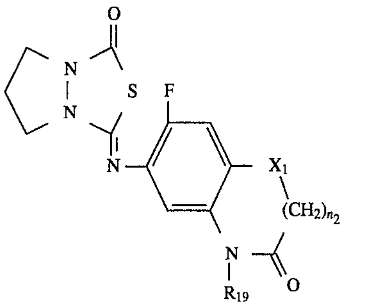
(Ih)
| Comp. No. | $X_1$ | $R_{19}$ | $n_2$ | Phys. data |
|---|---|---|---|---|
| 6.129 | S | 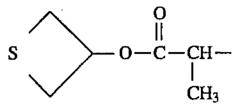 | 0 | |
| 6.130 | S | 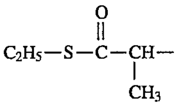 | 0 | |
| 6.131 | S | 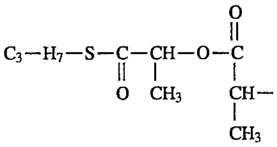 | 0 | |
| 6.132 | S | 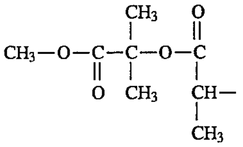 | 0 | |
TABLE 7
Compounds of formula Ii
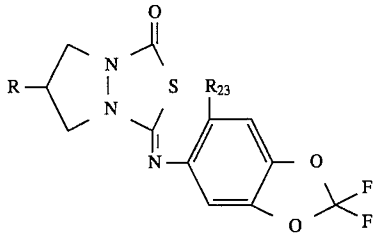
(Ii)
| Comp. No. | R | $R_{23}$ | Phys. data |
|---|---|---|---|
| 7.01 | H | F | |
| 7.02 | H | H | |
| 7.03 | $CH_3$ | F | |
| 7.04 | $CH_3$ | H | |
| 7.05 | $C_2H_5$ | F | |
| 7.06 | $C_2H_5$ | H | |
TABLE 7-continued
Compounds of formula Ii
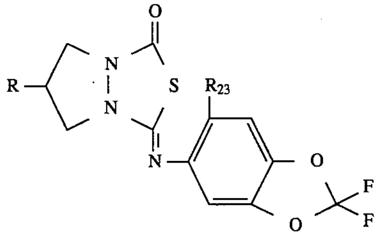
(Ii)
| Comp. No. | R | $R_{23}$ | Phys. data |
|---|---|---|---|
| 7.07 | 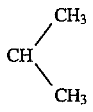 | F | |
| 7.08 | 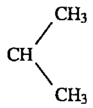 | H | |

TABLE 7-continued

Compounds of formula Ii

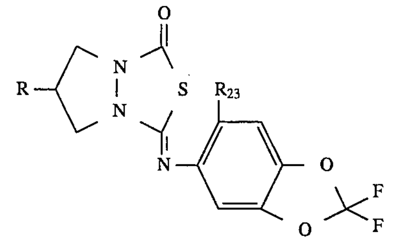

(Ii)

| Comp. No. | R | $R_{23}$ | Phys. data |
|---|---|---|---|
| 7.09 | $CF_3$ | F | |
| 7.10 | $CF_3$ | H | |

TABLE 8

Compounds of formula Ij

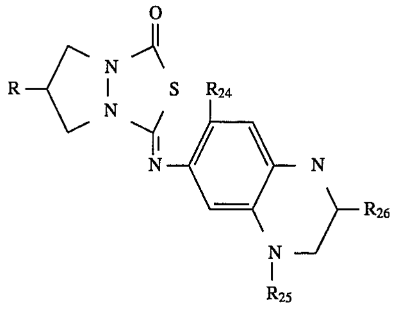

(Ij)

| Comp. No. | R | $R_{24}$ | $R_{25}$ | $R_{26}$ | Phys. data |
|---|---|---|---|---|---|
| 8.01 | H | H | H | H | |
| 8.02 | H | F | H | H | |
| 8.03 | H | F | $CH_3$ | H | |
| 8.04 | H | F | $CH_3$ | $CH_3$ | |
| 8.05 | H | F | 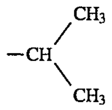 | H | |
| 8.06 | H | F | 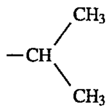 | $CH_3$ | |
| 8.07 | H | F | $-CH_2-C\equiv CH$ | $CH_3$ | |
| 8.08 | $CH_3$ | F | $-CH_2-C\equiv CH$ | H | |
| 8.09 | $CH_3$ | F | $-CH_2-C\equiv CH$ | $CH_3$ | |
| 8.10 | 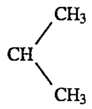 | F | $-CH_2-C\equiv CH$ | H | |

TABLE 8-continued

Compounds of formula Ij

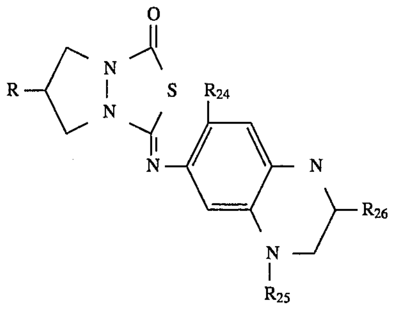

(Ij)

| Comp. No. | R | $R_{24}$ | $R_{25}$ | $R_{26}$ | Phys. data |
|---|---|---|---|---|---|
| 8.11 | 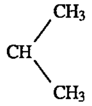 | F | $-CH_2-C\equiv CH$ | $CH_3$ | |
| 8.12 | $CF_3$ | F | $-CH_2-C\equiv CH$ | H | |
| 8.13 | $CF_3$ | F | $-CH_2-C\equiv CH$ | $CH_3$ | |

TABLE 9

Compounds of formula Ik

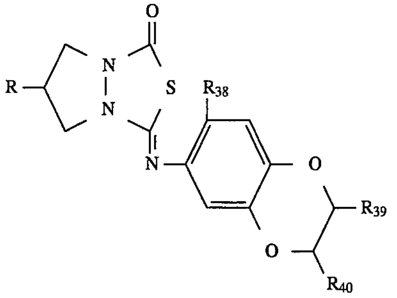

(Ik)

| Comp. No. | R | $R_{38}$ | $R_{39}/R_{40}$ | Phys. data |
|---|---|---|---|---|
| 9.01 | H | H | H | |
| 9.02 | H | F | H | |
| 9.03 | H | F | $CH_3$ | |
| 9.04 | $CH_3$ | H | H | |
| 9.05 | $CH_3$ | H | $CH_3$ | |
| 9.06 | 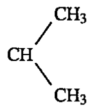 | F | $CH_3$ | |
| 9.07 | 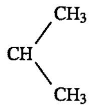 | H | H | |
| 9.08 | $CF_3$ | H | H | |
| 9.09 | $CF_3$ | F | $CH_3$ | |

TABLE 10

Compounds of formula Il

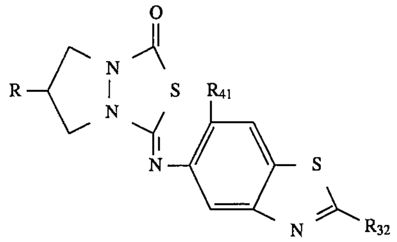

(Il)

| Comp. No. | R | $R_{41}$ | $R_{32}$ | Phys. data |
|---|---|---|---|---|
| 10.01 | H | H | H | |
| 10.02 | H | F | H | |
| 10.03 | H | F | $CH_3$ | |
| 10.04 | $CH_3$ | H | H | |
| 10.05 | $CH_3$ | F | H | |
| 10.06 | $CH_3$ | F | $CH_3$ | |
| 10.07 | 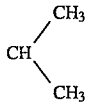 | H | H | |
| 10.08 | 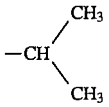 | F | H | |
| 10.09 | 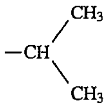 | F | $CH_3$ | |
| 10.10 | $CF_3$ | H | H | |
| 10.11 | $CF_3$ | F | H | |
| 10.12 | $CF_3$ | F | $CH_3$ | |

TABLE 11

Compounds of formula Im

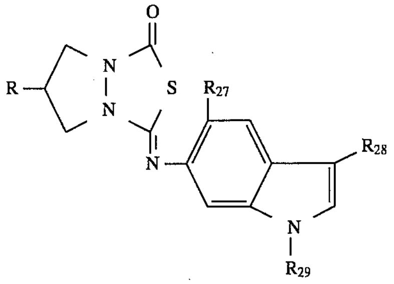

(Im)

| Comp. No. | R | $R_{27}$ | $R_{29}$ | $R_{28}$ | Phys. data |
|---|---|---|---|---|---|
| 11.01 | H | H | H | H | |
| 11.02 | H | F | H | H | |
| 11.03 | H | F | $CH_3$ | H | |
| 11.04 | $CH_3$ | F | $CH_3$ | H | |
| 11.05 | $CH_3$ | F | $CH_2-C\equiv CH$ | H | |
| 11.06 | H | F | $CH_2-C\equiv CH$ | H | |

TABLE 11-continued

Compounds of formula Im

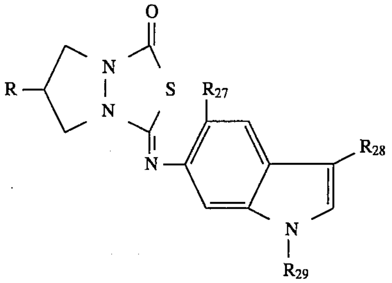

(Im)

| Comp. No. | R | $R_{27}$ | $R_{29}$ | $R_{28}$ | Phys. data |
|---|---|---|---|---|---|
| 11.07 | 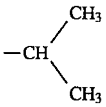 | F | $CH_2-C\equiv CH$ | H | |
| 11.08 | $CF_3$ | F | $CH_2-C\equiv CH$ | H | |
| 11.09 | $CF_3$ | F | $CH_2-C\equiv CH$ | $CH_3$ | |
| 11.10 | H | H | $CH_2-C\equiv CH$ | $CH_3$ | |
| 11.11 | H | F | $CH_2-C\equiv CH$ | $CH_3$ | |

TABLE 12

Compounds of formula In

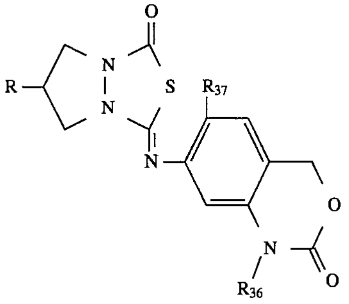

(In)

| Comp. No. | R | $R_{37}$ | $R_{36}$ |
|---|---|---|---|
| 12.01 | H | H | H |
| 12.02 | H | F | H |
| 12.03 | H | F | $CH_3$ |
| 12.04 | H | F | $CH_2-C\equiv CH$ |
| 12.05 | H | F | 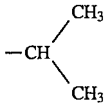 |
| 12.06 | $CF_3$ | F | $CH_2-C\equiv CH$ |

TABLE 13

Compounds of formula Io

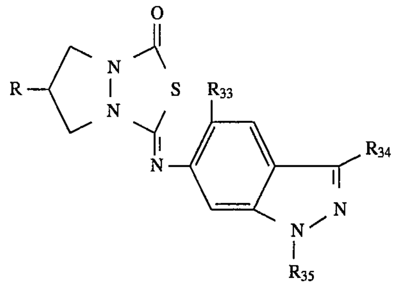

(Io)

| Comp. No. | R | $R_{33}$ | $R_{34}$ | $R_{35}$ |
|---|---|---|---|---|
| 13.01 | H | H | H | H |
| 13.02 | H | H | $CH_3$ | H |
| 13.03 | H | H | $CH_2-C\equiv CH$ | H |
| 13.04 | H | F | H | H |
| 13.05 | H | F | $CH_3$ | H |
| 13.06 | H | F | $CH_2-C\equiv CH$ | H |
| 13.07 | $CF_3$ | F | $CH_2-C\equiv CH$ | H |

TABLE 14

Compounds of formula Ip

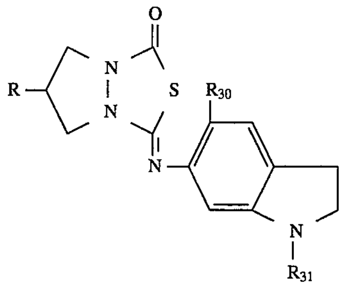

(Ip)

| Comp. No. | R | $R_{30}$ | $R_{31}$ |
|---|---|---|---|
| 14.01 | H | H | H |
| 14.02 | H | F | H |
| 14.03 | H | F | $CH_3$ |
| 14.04 | H | F | $-CH(CH_3)_2$ |
| 14.05 | H | F | $CH_2-C\equiv CH$ |
| 14.06 | $CH_3$ | F | $-O-CH_2-C\equiv CH$ |
| 14.07 | $-CH(CH_3)_2$ | F | $-O-CH_2-C\equiv CH$ |

TABLE 15

Compounds of formula Iq

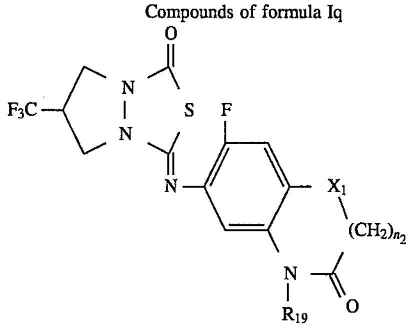

(Iq)

| Comp. No. | $X_1$ | $R_{19}$ | $n_2$ | Phys. data |
|---|---|---|---|---|
| 15.01 | O | H | 0 | |
| 15.02 | O | H | 1 | |
| 15.03 | O | $CH_3$ | 0 | |
| 15.04 | O | $C_2H_5$ | 0 | |
| 15.05 | O | $C_2H_5$ | 1 | |
| 15.06 | O | $CH(CH_3)_2$ | 0 | |
| 15.07 | O | $CH(CH_3)_2$ | 1 | |

TABLE 15-continued
Compounds of formula Iq
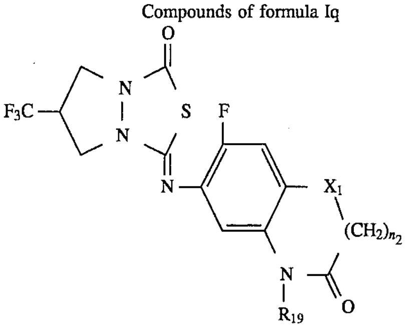
(Iq)
| Comp. No. | $X_1$ | $R_{19}$ | $n_2$ | Phys. data |
|---|---|---|---|---|
| 15.08 | O | $CH_2-C\equiv CH$ | 0 | |
| 15.09 | O | $CH_2-C\equiv CH$ | 1 | |
| 15.10 | O | H | 0 | |
| 15.11 | O | H | 1 | |
| 15.12 | O | $CH_3$ | 0 | |
| 15.13 | O | $C_2H_5$ | 0 | |
| 15.14 | O | $C_2H_5$ | 1 | |
| 15.15 | O | 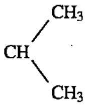 | 0 | |
| 15.16 | O | 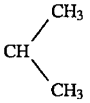 | 1 | |
| 15.17 | O | $CH_2-C\equiv CH$ | 0 | |
| 15.18 | O | $CH_2-C\equiv CH$ | 1 | |
| 15.19 | S | H | 0 | |
| 15.20 | S | $CH_3$ | 0 | |
| 15.21 | S | $C_2H_5$ | 0 | |
| 15.22 | S | $C_3H_7$(n) | 0 | |
| 15.23 | S | 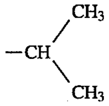 | 0 | |
| 15.24 | S | $-C_4H_9$(n) | 0 | |
| 15.25 | S | $-C_4H_9$(S) | 0 | |
| 15.26 | S | $-C_4H_9$(i) | 0 | |
| 15.27 | S | $-C_4H_9$(t) | 0 | |
| 15.28 | S | $-CH_2-CH=CH$ | 0 | |
| 15.29 | S | $-CH_2-CH=CH_2-CH_3$ | 0 | |
| 15.30 | S | 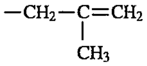 | 0 | |
| 15.31 | S | $-CH_2-C\equiv CH$ | 0 | |
| 15.32 | S | $-CH_2-C\equiv C-CH_3$ | 0 | |
| 15.33 | S | 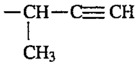 | 0 | |
| 15.34 | S | 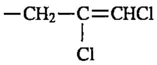 | 0 | |
| 15.35 | S | 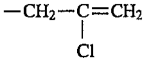 | 0 | |

TABLE 15-continued

Compounds of formula Iq

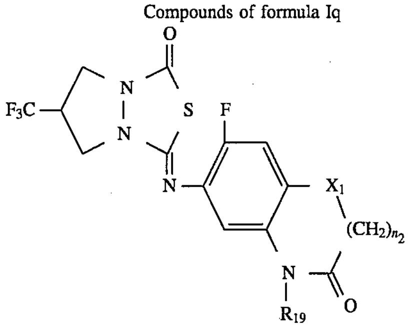

(Iq)

| Comp. No. | $X_1$ | $R_{19}$ | $n_2$ | Phys. data |
|---|---|---|---|---|
| 15.36 | S | $-CH_2-CH=CHCl$ | 0 | |
| 15.37 | S | $-CH_2-CH=C(Cl)-CH_3$ | 0 | |
| 15.38 | S | $-CH_2-CH=CH-Br$ | 0 | |
| 15.39 | S | $-CH_2-C(Br)=CH-Br$ | 0 | |
| 15.40 | S | $-CH_2-C(Br)=CH_2$ | 0 | |
| 15.41 | S | $-CH_2-O-CH_3$ | 0 | |
| 15.42 | S | $-CH_2-O-C_3H_7$ | 0 | |
| 15.43 | S | $-CH_2-O-C_4H_9$ | 0 | |
| 15.44 | S | $-CH_2-CH_2-O-CH_3$ | 0 | |
| 15.45 | S | $-CH_2-CH_2-O-C_2H_5$ | 0 | |
| 15.46 | S | $-CH_2-CN$ | 0 | |
| 15.47 | S | $-CH_2-CH_2-CN$ | 0 | |
| 15.48 | S | $-CH(CH_3)-CN$ | 0 | |
| 15.49 | S | $-CH_2-COOCH_3$ | 0 | |
| 15.50 | S | $-CH_2-COOC_2H_5$ | 0 | |
| 15.51 | S | $-CH_2-COO-CH(CH_3)_2$ | 0 | |
| 15.52 | S | $-CH_2-COOC_5H_{11}$ | 0 | |
| 15.53 | S | $-CH_2-CH_2-COOCH_3$ | 0 | |
| 15.54 | S | $-CH_2-CH_2-COOC_2H_5$ | 0 | |
| 15.55 | S | $-CH_2-CH_2-COO-CH(CH_3)_2$ | 0 | |
| 15.56 | S | $-CH_2-CH_2-COO-CH(CH_3)_2$ | 0 | |
| 15.57 | S | $-CH(CH_3)-COOC_2H_5$ | 0 | |
| 15.58 | S | $-CH(CH_3)-COO-CH(CH_3)_2$ | 0 | |

TABLE 15-continued
Compounds of formula Iq
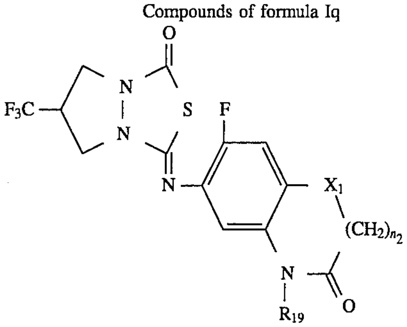
(Iq)
| Comp. No. | $X_1$ | $R_{19}$ | $n_2$ | Phys. data |
|---|---|---|---|---|
| 15.59 | S | 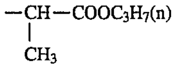 | 0 | |
| 15.60 | S | 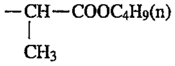 | 0 | |
| 15.61 | S | 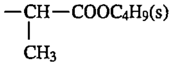 | 0 | |
| 15.62 | S | 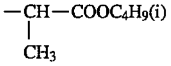 | 0 | |
| 15.63 | S | 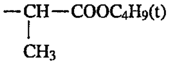 | 0 | |
| 15.64 | S | 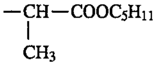 | 0 | |
| 15.65 | S | 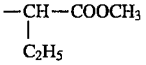 | 0 | |
| 15.66 | S | 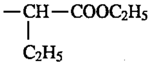 | 0 | |
| 15.67 | S | 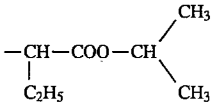 | 0 | |
| 15.68 | S | 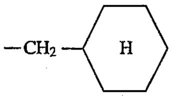 | 0 | |
| 15.69 | S | 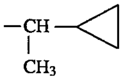 | 0 | |
| 15.70 | S | 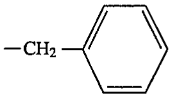 | 0 | |
| 15.71 | S | 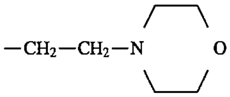 | 0 | |
| 15.72 | S | 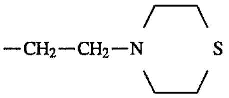 | 0 | |

TABLE 15-continued
Compounds of formula Iq
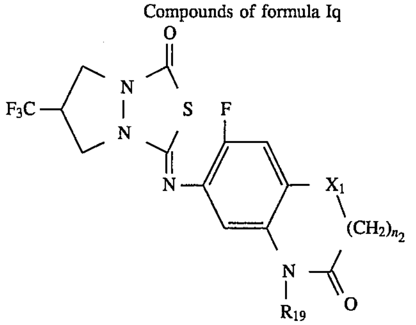
(Iq)
| Comp. No. | $X_1$ | $R_{19}$ | $n_2$ | Phys. data |
|---|---|---|---|---|
| 15.73 | S | 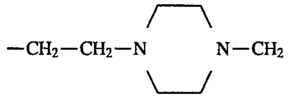 | 0 | |
| 15.74 | S | 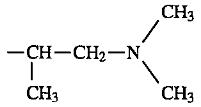 | 0 | |
| 15.75 | S | 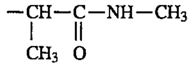 | 0 | |
| 15.76 | S | 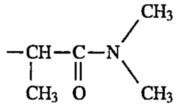 | 0 | |
| 15.77 | S | 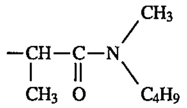 | 0 | |
| 15.78 | S | $FCH_2-$ | 0 | |
| 15.79 | S | $F_2CH-$ | 0 | |
| 15.80 | S | $FCH_2-CH_2-$ | 0 | |
| 15.81 | S | $CF_3-CH_2-$ | 0 | |
| 15.82 | S | $FCH_2-CH_2-CH_2-$ | 0 | |
| 15.83 | S | $Cl-CH_2-$ | 0 | |
| 15.84 | S | $Br-CH_2-$ | 0 | |
| 15.85 | S | $Cl_3C-$ | 0 | |
| 15.86 | S | $F_3C-$ | 0 | |
| 15.87 | S | $Cl-CH_2-CH_2-$ | 0 | |
| 15.88 | S | $Br-CH_2-CH_2-$ | 0 | |
| 15.89 | S | $CF_3-CF_2-$ | 0 | |
| 15.90 | S | $IC\equiv C-CH_2-$ | 0 | |
| 15.91 | S | $CH_3-O-CH_2-O-CH_2-$ | 0 | |
| 15.92 | S | $CH_3-O-CH_2-CH_2-O-CH_2-$ | 0 | |
| 15.93 | S | $C_2H_5-O-CH_2-O-CH_2-$ | 0 | |
| 15.94 | S | $CH_3-O-CH_2-O-CH_2-CH_2-$ | 0 | |
| 15.95 | S | $C_2H_5-O-CH_2-O-CH_2-CH_2-$ | 0 | |
| 15.96 | S | $C_2H_5-O-CH_2-CH_2-O-CH_2-$ | 0 | |
| 15.97 | S | $C_2H_5-O-CH_2-CH_2-O-CH_2-CH_2-$ | 0 | |
| 15.98 | S | $C_6H_5-CH=CH-CH_2-$ | 0 | |
| 15.99 | S | $-CH_2-COOH$ | 0 | |
| 15.100 | S | 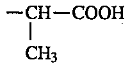 | 0 | |
| 15.101 | S | 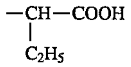 | 0 | |
| 15.102 | S | $-CH_2-CH_2-COOH$ | 0 | |
| 15.103 | S | 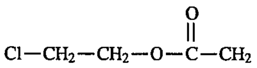 | 0 | |

TABLE 15-continued
Compounds of formula Iq
(Iq)
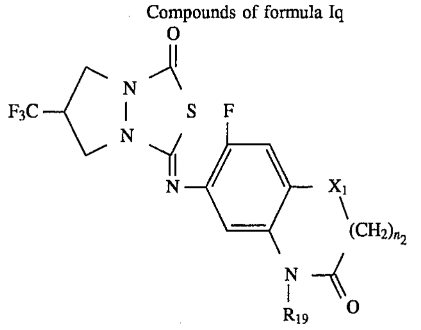
| Comp. No. | $X_1$ | $R_{19}$ | $n_2$ | Phys. data |
|---|---|---|---|---|
| 15.104 | S | $F-CH_2-CH_2-O-C(=O)-CH_2-$ | 0 | |
| 15.105 | S | $F-CH_2-CH_2-CH_2-O-C(=O)-CH_2-$ | 0 | |
| 15.106 | S | $F_3-C_2-CH_2-O-C(=O)-CH_2-$ | 0 | |
| 15.107 | S | $Cl-CH_2-CH_2-O-C(=O)-CH(CH_3)-$ | 0 | |
| 15.108 | S | $F-CH_2-CH_2-O-C(=O)-CH(CH_3)-$ | 0 | |
| 15.109 | S | $F-CH_2-CH_2-CH_2-O-C(=O)-CH(CH_3)-$ | 0 | |
| 15.110 | S | $CF_3-CH_2-O-C(=O)-CH(CH_3)$ | 0 | |
| 15.111 | S | $CH_3-O-CH_2-CH_2-O-C(=O)-CH_2$ | 0 | |
| 15.112 | S | $C_2H_5-O-CH_2-CH_2-O-C(=O)-CH_2-$ | 0 | |
| 15.113 | S | $C_3H_7-O-CH_2-CH_2-O-C(=O)-CH_2-$ | 0 | |
| 15.114 | S | $C_2H_5-O-C(=O)-CH(CH_3)-O-C(=O)-CH(CH_3)-$ | 0 | |
| 15.115 | S | $C_2H_5-O-C(=O)-CH_2-O-C(=O)-CH(CH_3)-$ | 0 | |
| 15.116 | S | 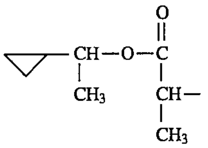 | 0 | |
| 15.117 | S | $CH_3-S-CH_2-CH(CH_3)-$ | 0 | |

TABLE 15-continued
Compounds of formula Iq
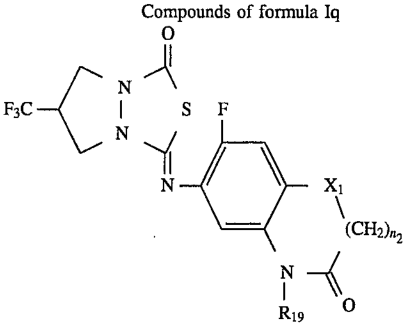
(Iq)
| Comp. No. | $X_1$ | $R_{19}$ | $n_2$ | Phys. data |
|---|---|---|---|---|
| 15.118 | S | $C_2H_5-S-CH_2-CH(CH_3)-$ | 0 | |
| 15.119 | S | $CH_3-S-CH_2-CH_2$ | 0 | |
| 15.120 | S | $C_3H_7-S-CH_2-CH(CH_3)-$ | 0 | |
| 15.121 | S | $(CH_3)_2CH-S-CH_2-CH(CH_3)-$ | 0 | |
| 15.122 | S | $C_4H_9-S-CH_2-CH(CH_3)-$ | 0 | |
| 15.123 | S | $C_5H_{11}-S-CH_2-CH(CH_3)-$ | 0 | |
| 15.124 | S | $CH_3-SO_2-$ | 0 | |
| 15.125 | S | $C_2H_5SO_2-$ | 0 | |
| 15.126 | S | $CH_2=CH-CH_2-O-CH_2-$ | 0 | |
| 15.127 | S | 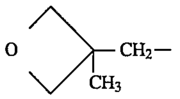 | 0 | |
| 15.128 | S | 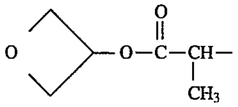 | 0 | |
| 15.129 | S | 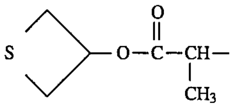 | 0 | |
| 15.130 | S | $C_2H_5-S-C(=O)-CH(CH_3)-$ | 0 | |
| 15.131 | S | $C_3-H_7-S-C(=O)-CH(CH_3)-O-C(=O)-CH(CH_3)-$ | 0 | |

TABLE 15-continued
Compounds of formula Iq
(Iq)
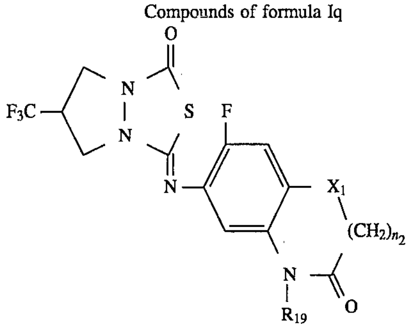
| Comp. No. | $X_1$ | $R_{19}$ | $n_2$ | Phys. data |
|---|---|---|---|---|
| 15.132 | S | 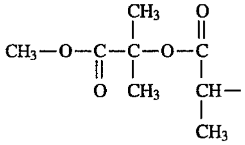 | 0 | |
TABLE 16
Compounds of formula Ir
(Ir)
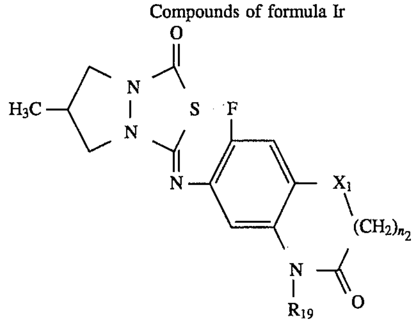
| Comp. No. | $X_1$ | $R_{19}$ | $n_2$ | Phys. data |
|---|---|---|---|---|
| 16.01 | O | H | 0 | |
| 16.02 | O | H | 1 | |
| 16.03 | O | $CH_3$ | 0 | |
| 16.04 | O | $C_2H_5$ | 0 | |
| 16.05 | O | $C_2H_5$ | 1 | |
| 16.06 | O | 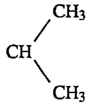 | 0 | |
| 16.07 | O | 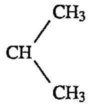 | 1 | |
| 16.08 | O | $CH_2-C\equiv CH$ | 0 | |
| 16.09 | O | $CH_2-C\equiv CH$ | 1 | |
| 16.10 | O | H | 0 | |
| 16.11 | O | H | 1 | |
| 16.12 | O | $CH_3$ | 0 | |
| 16.13 | O | $C_2H_5$ | 0 | |
| 16.14 | O | $C_2H_5$ | 1 | |
| 16.15 | O | 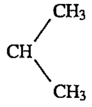 | 0 | |

TABLE 16-continued

Compounds of formula Ir

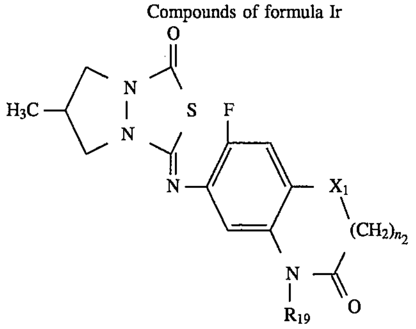

(Ir)

| Comp. No. | $X_1$ | $R_{19}$ | $n_2$ | Phys. data |
|---|---|---|---|---|
| 16.16 | O | —CH(CH$_3$)$_2$ | 1 | |
| 16.17 | O | CH$_2$—C≡CH | 0 | |
| 16.18 | O | CH$_2$—C≡CH | 1 | |
| 16.19 | S | H | 0 | |
| 16.20 | S | CH$_3$ | 0 | |
| 16.21 | S | C$_2$H$_5$ | 0 | |
| 16.22 | S | C$_3$H$_7$(n) | 0 | |
| 16.23 | S | —CH(CH$_3$)$_2$ | 0 | m.p. 136–137° C. |
| 16.24 | S | —C$_4$H$_9$(n) | 0 | |
| 16.25 | S | —C$_4$H$_9$(s) | 0 | |
| 16.26 | S | —C$_4$H$_9$(i) | 0 | |
| 16.27 | S | —C$_4$H$_9$(t) | 0 | |
| 16.28 | S | —CH$_2$—CH═CH | 0 | |
| 16.29 | S | —CH$_2$—CH═CH$_2$—CH$_3$ | 0 | |
| 16.30 | S | —CH$_2$—C(CH$_3$)═CH$_2$ | 0 | |
| 16.31 | S | —CH$_2$—C≡CH | 0 | |
| 16.32 | S | —CH$_2$—C≡C—CH$_3$ | 0 | |
| 16.33 | S | —CH(CH$_3$)—C≡CH | 0 | |
| 16.34 | S | —CH$_2$—C(Cl)═CHCl | 0 | |
| 16.35 | S | —CH$_2$—C(Cl)═CH$_2$ | 0 | |
| 16.36 | S | —CH$_2$—CH═CHCl | 0 | |
| 16.37 | S | —CH$_2$—CH═C(Cl)—CH$_3$ | 0 | |
| 16.38 | S | —CH$_2$—CH═CH—Br | 0 | |
| 16.39 | S | —CH$_2$—C(Br)═CH—Br | 0 | |
| 16.40 | S | —CH$_2$—C(Br)═CH$_2$ | 0 | |

TABLE 16-continued

Compounds of formula Ir (Ir)

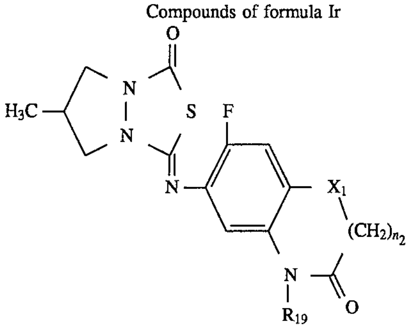

| Comp. No. | $X_1$ | $R_{19}$ | $n_2$ | Phys. data |
|---|---|---|---|---|
| 16.41 | S | $-CH_2-O-CH_3$ | 0 | |
| 16.42 | S | $-CH_2-O-C_3H_7$ | 0 | |
| 16.43 | S | $-CH_2-O-C_4H_9$ | 0 | |
| 16.44 | S | $-CH_2-CH_2-O-CH_3$ | 0 | |
| 16.45 | S | $-CH_2-CH_2-O-C_2H_5$ | 0 | |
| 16.46 | S | $-CH_2-CN$ | 0 | |
| 16.47 | S | $-CH_2-CH_2-CN$ | 0 | |
| 16.48 | S | $-CH(CH_3)-CN$ | 0 | |
| 16.49 | S | $-CH_2-COOCH_3$ | 0 | |
| 16.50 | S | $-CH_2-COOC_2H_5$ | 0 | |
| 16.51 | S | $-CH_2-COO-CH(CH_3)_2$ | 0 | |
| 16.52 | S | $-CH_2-COOC_5H_{11}$ | 0 | |
| 16.53 | S | $-CH_2-CH_2-COOCH_3$ | 0 | |
| 16.54 | S | $-CH_2-CH_2-COOC_2H_5$ | 0 | |
| 16.55 | S | $-CH_2-CH_2-COO-CH(CH_3)_2$ | 0 | |
| 16.56 | S | $-CH(CH_3)-COOCH_3$ | 0 | |
| 16.57 | S | $-CH(CH_3)-COOC_2H_5$ | 0 | (resinous) |
| 16.58 | S | $-CH(CH_3)-COO-CH(CH_3)_2$ | 0 | |
| 16.59 | S | $-CH(CH_3)-COOC_3H_7(n)$ | 0 | |
| 16.60 | S | $-CH(CH_3)-COOC_4H_9(n)$ | 0 | |
| 16.61 | S | $-CH(CH_3)-COOC_4H_9(s)$ | 0 | |
| 16.62 | S | $-CH(CH_3)-COOC_4H_9(i)$ | 0 | |
| 16.63 | S | $-CH(CH_3)-COOC_4H_9(t)$ | 0 | |

TABLE 16-continued
Compounds of formula Ir
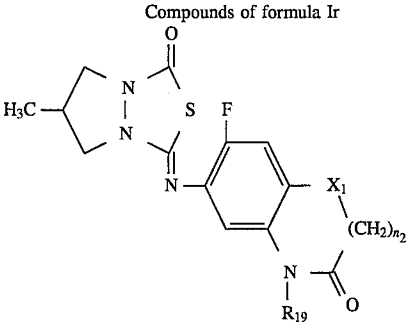
(Ir)
| Comp. No. | $X_1$ | $R_{19}$ | $n_2$ | Phys. data |
| --- | --- | --- | --- | --- |
| 16.64 | S | $-CH-COOC_5H_{11}$<br>\|<br>$CH_3$ | 0 | |
| 16.65 | S | $-CH-COOCH_3$<br>\|<br>$C_2H_5$ | 0 | |
| 16.66 | S | $-CH-COOC_2H_5$<br>\|<br>$C_2H_5$ | 0 | |
| 16.67 | S | 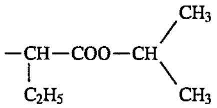 | 0 | |
| 16.68 | S | 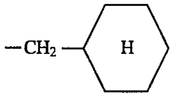 | 0 | |
| 16.69 | S | 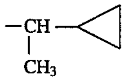 | 0 | |
| 16.70 | S | 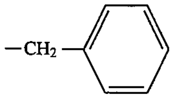 | 0 | |
| 16.71 | S | 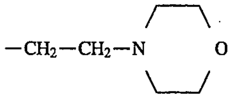 | 0 | |
| 16.72 | S | 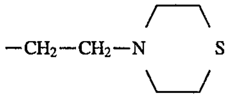 | 0 | |
| 16.73 | S | 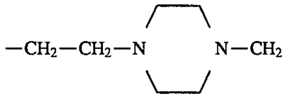 | 0 | |
| 16.74 | S | 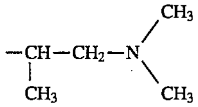 | 0 | |
| 16.75 | S | $-CH-C-NH-CH_3$<br>\| ‖<br>$CH_3$ O | 0 | |
| 16.76 | S | 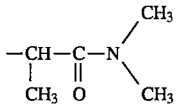 | 0 | |

TABLE 16-continued
Compounds of formula Ir
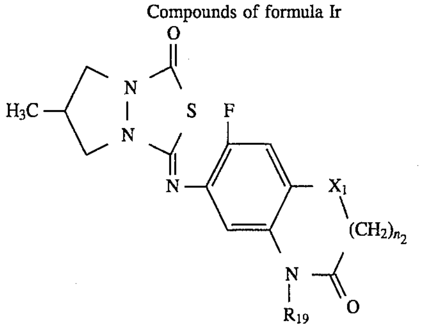
(Ir)
| Comp. No. | $X_1$ | $R_{19}$ | $n_2$ | Phys. data |
|---|---|---|---|---|
| 16.77 | S | 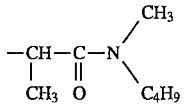 | 0 | |
| 16.78 | S | $FCH_2-$ | 0 | |
| 16.79 | S | $F_2CH-$ | 0 | |
| 16.80 | S | $FCH_2-CH_2-$ | 0 | |
| 16.81 | S | $CF_3-CH_2-$ | 0 | |
| 16.82 | S | $FCH_2-CH_2-CH_2-$ | 0 | |
| 16.83 | S | $Cl-CH_2-$ | 0 | |
| 16.84 | S | $Br-CH_2-$ | 0 | |
| 16.85 | S | $Cl_3C-$ | 0 | |
| 16.86 | S | $F_3C-$ | 0 | |
| 16.87 | S | $C-CH_2-CH_2-$ | 0 | |
| 16.88 | S | $Br-CH_2-CH_2-$ | 0 | |
| 16.89 | S | $CF_3-CF_2-$ | 0 | |
| 16.90 | S | $IC\equiv C-CH_2-$ | 0 | |
| 16.91 | S | $CH_3-O-CH_2-O-CH_2-$ | 0 | |
| 16.92 | S | $CH_3-O-CH_2-CH_2-O-CH_2-$ | 0 | |
| 16.93 | S | $C_2H_5-O-CH_2-O-CH_2-$ | 0 | |
| 16.94 | S | $CH_3-O-CH_2-O-CH_2-CH_2-$ | 0 | |
| 16.95 | S | $C_2H_5-O-CH_2-O-CH_2-CH_2-$ | 0 | |
| 16.96 | S | $C_2H_5-O-CH_2-CH_2-O-CH_2-$ | 0 | |
| 16.97 | S | $C_2H_5-O-CH_2-CH_2-O-CH_2-CH_2-$ | 0 | |
| 16.98 | S | $C_6H_5-CH=CH-CH_2-$ | 0 | |
| 16.99 | S | $-CH_2-COOH$ | 0 | |
| 16.100 | S | 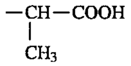 | 0 | |
| 16.101 | S | 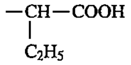 | 0 | |
| 16.102 | S | $-CH_2-CH_2-COOH$ | 0 | |
| 16.103 | S | 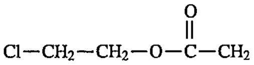 | 0 | |
| 16.104 | S | 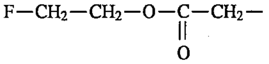 | 0 | |
| 16.105 | S | 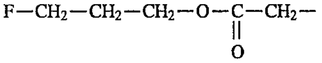 | 0 | |
| 16.106 | S | 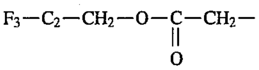 | 0 | |
| 16.107 | S | 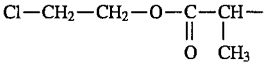 | 0 | |
| 16.108 | S | 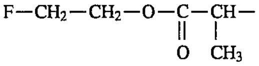 | 0 | |

TABLE 16-continued
Compounds of formula Ir
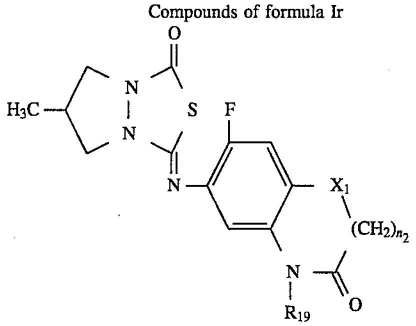
(Ir)
| Comp. No. | $X_1$ | $R_{19}$ | $n_2$ | Phys. data |
|---|---|---|---|---|
| 16.109 | S | $F-CH_2-CH_2-CH_2-O-C(=O)-CH(CH_3)-$ | 0 | |
| 16.110 | S | $CF_3-CH_2-O-C(=O)-CH(CH_3)$ | 0 | |
| 16.111 | S | $CH_3-O-CH_2-CH_2-O-C(=O)-CH_2$ | 0 | |
| 16.112 | S | $C_2H_5-O-CH_2-CH_2-O-C(=O)-CH_2-$ | 0 | |
| 16.113 | S | $C_3H_7-O-CH_2-CH_2-O-C(=O)-CH_2-$ | 0 | |
| 16.114 | S | $C_2H_5-O-C(=O)-CH(CH_3)-O-C(=O)-CH(CH_3)-$ | 0 | |
| 16.115 | S | $C_2H_5-O-C(=O)-CH_2-O-C(=O)-CH(CH_3)-$ | 0 | |
| 16.116 | S | 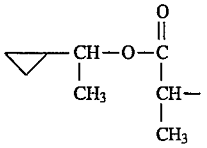 | 0 | |
| 16.117 | S | $CH_3-S-CH_2-CH(CH_3)-$ | 0 | |
| 16.118 | S | $C_2H_5-S-CH_2-CH(CH_3)-$ | 0 | |
| 16.119 | S | $CH_3-S-CH_2-CH_2$ | 0 | |
| 16.120 | S | $C_3H_7-S-CH_2-CH(CH_3)-$ | 0 | |
| 16.121 | S | $(CH_3)_2CH-S-CH_2-CH(CH_3)-$ | 0 | |
| 16.122 | S | $C_4H_9-S-CH_2-CH(CH_3)-$ | 0 | |

TABLE 16-continued

Compounds of formula Ir

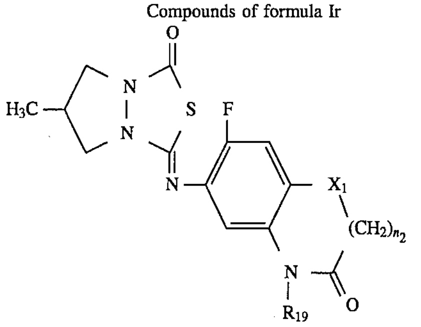

(Ir)

| Comp. No. | $X_1$ | $R_{19}$ | $n_2$ | Phys. data |
|---|---|---|---|---|
| 16.123 | S | 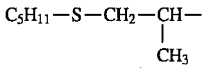 | 0 | |
| 16.124 | S | $CH_3-SO_2-$ | 0 | |
| 16.125 | S | $C_2H_5SO_2-$ | 0 | |
| 16.126 | S | $CH_2=CH-CH_2-O-CH_2-$ | 0 | |
| 16.127 | S | 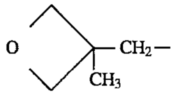 | 0 | |
| 16.128 | S | 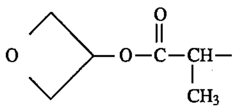 | 0 | |
| 16.129 | S | 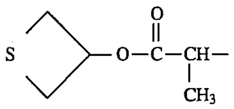 | 0 | |
| 16.130 | S | 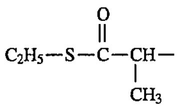 | 0 | |
| 16.131 | S | 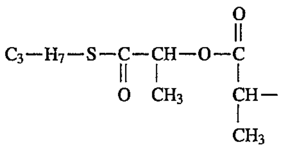 | 0 | |
| 16.132 | S | 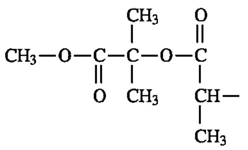 | 0 | |

BIOLOGICAL EXAMPLES

Example B 1

Preemergence herbicidal action

In a greenhouse, immediately after the test plants have been sown in seed trays, the surface of the soil is treated with an aqueous spray mixture corresponding to a rate of application of 4 kg of active ingredient/hectare. The seed trays are kept in the greenhouse at 22°–25° C. and 50–70% relative humidity.

The herbicidal action is evaluated after 3 weeks using a scale of nine ratings (1=total damage, 9=no damage), in comparison with an untreated control group.

Ratings from 1 to 4 (especially from 1 to 3) indicate a good to very good herbicidal action.

Ratings from 6 to 9 (especially from 7 to 9) indicate good tolerance (especially in cultivated plants).

In this test, the compounds of Tables 1–16 exhibit pronounced herbicidal activity. Examples of the good herbicidal activity are given in Table B 1:

TABLE B1

| Preemergence herbicidal action: | | | | |
|---|---|---|---|---|
| | Test plant: | | | |
| Compound no. | Avena | Sinapis | Setaria | Stellaria |
| 1.005 | 1 | 1 | 1 | 1 |
| 1.125 | 2 | 1 | 1 | 1 |
| 6.009 | 1 | 1 | 1 | 1 |

Example B2

Postemergence herbicidal action (contact herbicide)

A number of weeds, both monocotyledonous and dicotyledonous, are sprayed postemergence (in the 4- to 6-leaf stage) with an aqueous active ingredient dispersion at a rate of 4 kg of active ingredient per hectare and kept at 24°–26° C. and 45–60% relative humidity. The herbicidal action is evaluated 15 days after treatment using a scale of nine ratings (1=total damage, 9=no damage), in comparison with an untreated control group.

The compounds of Tables 1–16 exhibit pronounced herbicidal activity in this test too. Examples of the good herbicidal activity are given in Table B2:

TABLE B2

| Postemergence herbicidal action | | | | | |
|---|---|---|---|---|---|
| | Test plant: | | | | |
| Compound no. | Avena | Setaria | Lolium | Sinapis | Stellaria |
| 1.005 | 1 | 2 | 2 | 1 | 1 |
| 1.125 | 3 | 2 | 2 | 1 | 2 |
| 6.009 | 1 | 1 | — | 1 | 1 |

Example B3

Herbicidal action in wild rice (paddy rice)

The weeds *Echinochloa crus galli* and *Monocharia vag.*, which occur in water, are sown in plastic beakers (surface area: 60 $cm^2$; volume: 500 ml). After sowing, the beakers are filled with water up to the surface of the soil. 3 days after sowing, the water level is increased to slightly above the soil surface (3–5 mm). Application is effected 3 days after sowing by spraying the beakers with the test compounds. The dosage used corresponds to an amount of active ingredient of 2 kg a.i. per hectare. The beakers are then kept in a greenhouse under optimum growth conditions for rice weeds, i.e. at 25°–30° C. and at high humidity.

The evaluation of the tests takes place 3 weeks after application. The compounds of Tables 1 to 14 damage the weeds.

Example B4

Growth inhibition of tropical cover crops

The test plants *Centrosema pubescens* and *Psophocarpus palustris* are propagated by means of cuttings in 4 cm peat pots containing earth (45%), peat (45%) and zonolite (10%). The plants are reared in a greenhouse at a day temperature of 27° C. and a night temperature of 23° C. The plants are illuminated for at least 14 hours/day at an intensity of at least 7000 lux.

About 50 days after taking the cuttings, the plants are transplanted into 13 cm pots, 4–5 plants/pot. After a further 60 days the plants are cut back to a height of about 15 cm and treated. For that purpose they are sprayed with an aqueous spray mixture comprising from 0.1 to 300 g of active ingredient/ha (generally in the form of a 25% formulation). The amount of water applied is about 200 l/ha.

4 weeks after treatment, the weight of the new growth is determined and expressed as a percentage of the average of the untreated controls. The necrotic damage is expressed as a percentage of the total leaf area.

The new growth on the treated plants is considerably less than that on the untreated controls.

Formulation Examples for liquid active ingredients of formula I (throughout, percentages are by weight)

| 1. Emulsifiable concentrates | a) | b) | c) |
|---|---|---|---|
| a compound of Tables 1-16 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | a) | b) | c) | d) |
|---|---|---|---|---|
| a compound of Tables 1–16 | 80% | 10% | 5% | 95% |
| propylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

The solutions are suitable for application in the form of micro-drops.

| 3. Granules | a) | b) | c) | d) |
|---|---|---|---|---|
| a compound of Tables 1–16 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in methylene chloride, the solution is sprayed onto the carrier, and the solvent is subsequently evaporated off in vacuo.

| 4. Dusts | a) | b) |
|---|---|---|
| a compound of Tables 1–16 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for solid active ingredients of formula I (throughout, percentages are by weight)

| 5. Wettable powders | a) | b) | c) |
| --- | --- | --- | --- |
| a compound of Tables 1-16 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrate | |
| --- | --- |
| a compound of Tables 1-16 | 10% |
| octylphenol polyethylene glycol ether (4-5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

| 7. Dusts | a) | b) |
| --- | --- | --- |
| a compound of Tables 1-16 | 5% | 8% |
| talcum | 95% | — |
| kaolin | — | 92% |

Ready-for-use dusts are obtained by mixing the active ingredient with the carrier and grinding the mixture in a suitable mill.

| 8. Extruder granules | |
| --- | --- |
| a compound of Tables 1-16 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 9. Coated granules | |
| --- | --- |
| a compound of Tables 1-16 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

-continued

| 10. Suspension concentrate | |
| --- | --- |
| a compound of Tables 1-16 | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil in the form of a 75% aqueous emulsion | 1% |
| water | 32% |

The finely ground active ingredient is intimately mixed with the adjuvants, giving a suspension concentrate from which suspensions of any desired concentration can be obtained by dilution with water.

The compounds of formula I are used in unmodified form or, preferably, in the form of compositions together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering or pouring, are chosen in accordance with the intended objectives and the prevailing circumstances.

What is claimed is:

1. A thiadiazabicyclooctane or thiadiazabicyclooctene of formula I

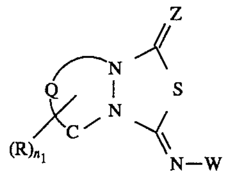

(I)

wherein

Z is oxygen or sulfur;

Q is —C—C—or —C═C—;

R is $C_1$–$C_6$alkyl, $C_3$–$C_6$cycloalkyl, $C_1$–$C_6$haloalkyl, $C_3$–$C_6$alkenyl, $C_3$–$C_6$alkynyl, $C_3$–$C_6$haloalkenyl, $C_3$–$C_6$haloalkynyl, phenyl, benzyl, phenyl substituted by $C_1$–$C_4$alkyl, $C_1$–$C_4$alkoxy, $C_1$–$C_4$haloalkyl or by halogen, benzyl substituted by $C_1$–$C_4$alkyl, $C_1$–$C_4$alkoxy, $C_1$–$C_4$haloalkyl or by halogen, it being possible for the unsubstituted and substituted phenyl and benzyl groups to occur in each case only once;

W is

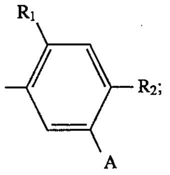

$(W_1)$

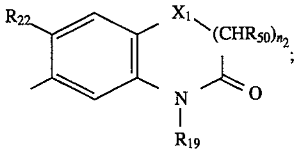

$(W_2)$

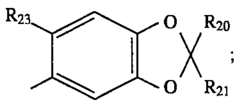

$(W_3)$

-continued

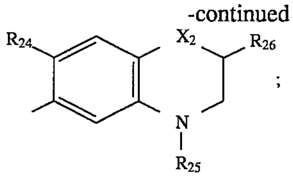
(W4)

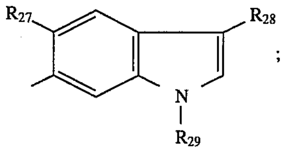
(W5)

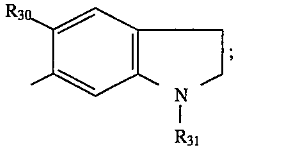
(W6)

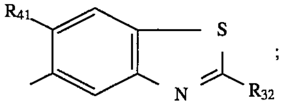
(W7)

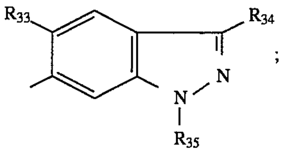
(W8)

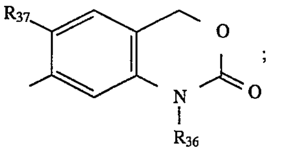
(W9)

or

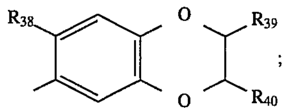
(W10)

$R_1$, $R_{22}$, $R_{23}$, $R_{24}$, $R_{27}$, $R_{30}$, $R_{33}$, $R_{37}$, $R_{38}$ and $R_{41}$ are each independently of the others hydrogen or halogen;

$R_2$ is hydrogen, cyano, nitro, halogen, $C_1$–$C_4$alkyl, $C_1$–$C_4$haloalkoxy or $C_1$–$C_4$haloalkyl;

A is hydrogen, cyano, nitro, $COR_3$, $X_3R_4$,

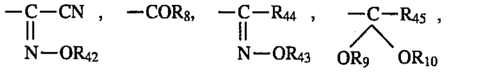

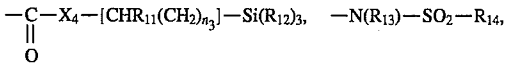

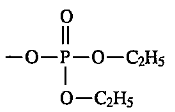
or
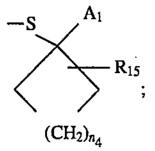
;

$A_1$ is cyano or —$COR_{16}$;

$R_3$ is halogen, $X_4$-$R_5$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_3$–$C_4$alkenylamino, diallylamino, —N-pyrrolidino, —N-piperidino, —N-morpholino, —N-thiomorpholino, —N-piperidazino, —O—N=C($CH_3$)—$CH_3$, or —O—$CH_2$—$CH_2$—O—N=C($CH_3$)—$CH_3$;

$R_4$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl that is unsubstituted or substituted in the phenyl ring by up to three identical or different substituents from the group halogen, $C_1$–$C_4$alkyl, halo-$C_1$–$C_4$alkyl, halo-$C_1$–$C_4$alkoxy and $C_1$–$C_4$alkoxy; or is furanoyl, thienyl; or $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl, di-$C_1$–$C_4$alkylaminocarbonyl; or phenylaminocarbonyl that is unsubstituted or substituted in the phenyl ring by up to three identical or different substituents from the group halogen, $C_1$–$C_4$alkyl, halo-$C_1$–$C_4$alkyl, halo-$C_1$–$C_4$alkoxy and $C_1$–$C_4$alkoxy or that is monosubstituted by cyano or by nitro, or dioxolan-2-yl that is unsubstituted or substituted by one or two $C_1$–$C_4$alkyl radicals, or dioxan-2-yl that is unsubstituted or substituted by one or two $C_1$–$C_4$alkyl radicals, or is $C_1$–$C_4$alkyl substituted by cyano, nitro, carboxy or by $C_1$–$C_8$alkylthio-$C_1$–$C_8$alkoxycarbonyl;

$R_5$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, halo-$C_3$–$C_8$alkenyl, $C_3$–$C_8$alkynyl, $C_3$–$C_7$cycloalkyl, $C_3$–$C_7$cycloalkyl-$C_1$–$C_4$alkyl, halo-$C_3$–$C_7$cycloalkyl, or benzyl that is unsubstituted or substituted in the phenyl ring by up to three identical or different substituents from the group halogen, $C_1$–$C_4$alkyl, halo-$C_1$–$C_4$alkyl, halo-$C_1$–$C_4$alkoxy and $C_1$–$C_4$alkoxy, or alkali metal ions, alkaline earth metal ions and ammonium ions or the group —[$CHR_6(CH_2)_{n_5}$]—$COOR_7$;

$R_6$, $R_{20}$, $R_{21}$, $R_{26}$, $R_{28}$, $R_{32}$, $R_{34}$, $R_{39}$, $R_{40}$, $R_{46}$, $R_{47}$, $R_{49}$, $R_{50}$, $R_{51}$ and $R_{52}$ are each independently of the others hydrogen or $C_1$–$C_4$alkyl;

$R_7$ and $R_{48}$ are each independently of the other hydrogen, $C_1$–$C_6$alkyl, $C_3$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

$R_8$, $R_{44}$ and $R_{45}$ are each independently of the others hydrogen, $C_1$–$C_4$alkyl, halo-$C_1$–$C_4$alkyl or $C_1$–$C_4$alkoxy-$C_1$–$C_4$alkyl;

$R_9$ and $R_{10}$ are each independently of the other $C_1$–$C_4$alkyl, $C_2$–$C_4$haloalkyl or $C_2$–$C_8$alkoxyalkyl, or $R_9$ and $R_{10}$ together are an ethano, propano or a cyclohexane-1,2-diyl bridge, those groups being either unsubstituted or substituted by one or two radicals from the group $C_1$–$C_4$alkyl, $C_1$–$C_4$haloalkyl and $C_1$–$C_4$hydroxyalkyl;

$R_{11}$ is hydrogen, $C_1$–$C_5$alkyl or $C_3$–$C_7$alkenyl;

the radicals $R_{12}$ are each independently of the others hydrogen or $C_1$–$C_8$alkyl;

$R_{13}$ is hydrogen, $C_1$–$C_5$alkyl, benzyl, halo-$C_1$–$C_4$alkyl, $C_3$–$C_8$alkenyl or $C_3$–$C_8$alkynyl;

$R_{14}$ is $C_1$–$C_6$alkyl, halo-$C_1$–$C_5$alkyl or di-$C_1$–$C_4$alkylamino;

$R_{15}$ is hydrogen, fluorine, chlorine, bromine, $C_1$–$C_4$alkyl or trifluoromethyl;

$R_{16}$ is chlorine, $X_5$-$R_{17}$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_3$–$C_4$alkenylamino, diallylamino, —N-pyrrolidino, —N-piperidino, —N-morpholino, —N-thiomorpholino, —N-piperidazino, the group $—O—N{=}C—(CH_3)—CH_3$, $—O—CH_2—CH_2—O—N{=}C(CH_3)—CH_3$ or the group $—N(OR_{46})—R_6$;

$R_{17}$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_3$–$C_8$alkenyl, halo-$C_3$–$C_8$alkenyl, $C_3$–$C_8$alkynyl, $C_3$–$C_7$cycloalkyl, $C_3$–$C_7$cycloalkyl-$C_1$–$C_4$alkyl, halo-$C_3$–$C_7$cycloalkyl, or benzyl that is unsubstituted or substituted in the phenyl ring by up to three identical or different substituents from the group halogen, $C_1$–$C_4$alkyl, halo-$C_1$–$C_4$alkyl, halo-$C_1$–$C_4$alkoxy and $C_1$–$C_4$alkoxy, or alkali metal ions, alkaline earth metal ions and ammonium ions, the group $—[CHR_{47}—(CH_2)_m]—COOR_{48}$, or the group $[CHR_{49}—(CH_2)_t—Si(R_8)_3]$;

m is 0, 1, 2, 3 or 4;

t is 0, 1, 2, 3 or 4;

$R_{18}$ is $C_1$–$C_4$alkyl;

$R_{19}$ is hydrogen, $C_1$–$C_6$alkyl, $C_2$–$C_4$alkenyl or $C_2$–$C_6$alkynyl; halo-substituted $C_1$–$C_6$alkyl, $C_2$–$C_4$alkenyl or $C_3$–$C_6$alkynyl; $C_1$–$C_4$alkoxy-$C_1$–$C_4$alkyl, $C_1$–$C_4$alkoxy-$C_1$–$C_2$alkoxy-$C_1$–$C_2$alkyl, 1-phenylpropen-3-yl, cyano- or $C_3$–$C_6$cycloalkyl-substituted $C_1$–$C_4$alkyl; carboxy-$C_1$–$C_4$alkyl, $C_1$–$C_6$alkoxycarbonyl-$C_1$–$C_4$alkyl, halo-$C_1$–$C_6$alkoxycarbonyl-$C_1$–$C_4$alkyl, $C_1$–$C_4$alkoxy-$C_1$–$C_2$alkoxycarbonyl-$C_1$–$C_4$alkyl, $C_1$–$C_6$alkoxycarbonyl-$C_1$–$C_2$alkoxycarbonyl-$C_1$–$C_4$alkyl, $C_3$–$C_6$cycloalkyl-$C_1$–$C_2$alkoxycarbonyl-$C_1$–$C_4$alkyl, $C_1$–$C_5$alkylaminocarbonyl-$C_1$–$C_4$alkyl, di-$C_1$–$C_5$alkylaminocarbonyl-$C_1$–$C_4$alkyl, $C_3$–$C_6$cycloalkyl, $C_1$–$C_4$alkylthio-$C_1$–$C_4$alkyl, benzyl or halo-substituted benzyl, $C_1$–$C_4$alkylsulfonyl, $C_3$–$C_6$alkenyloxy-$C_1$–$C_4$alkyl, $C_1$–$C_8$alkylcarbonyl,

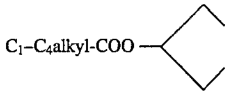,

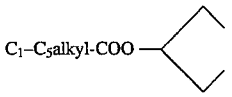, 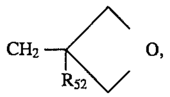, $C_1$–$C_4$alkylthiocarbonyl-$C_1$–$C_4$alkyl, or the group

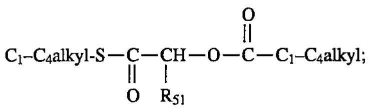;

$R_{25}$, $R_{29}$, $R_{31}$, $R_{35}$ and $R_{36}$ are each independently of the others hydrogen, $C_1$–$C_4$alkyl, $C_3$–$C_8$alkenyl, halo-$C_3$–$C_8$alkenyl, $C_3$–$C_8$alkynyl, $C_1$–$C_4$alkoxy-$C_1$–$C_8$alkyl, cyano-$C_1$–$C_4$alkyl, $C_1$–$C_8$alkoxycarbonyl-$C_1$–$C_4$alkyl, $C_3$–$C_7$cycloalkyl, $C_3$–$C_7$cycloalkyl-$C_1$–$C_4$alkyl, benzyl, —N-morpholino-, —N-thiomorpholino- or —N-piperidazino-substituted $C_1$–$C_4$alkyl, di-$C_1$–$C_4$alkylamino-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_1$–$C_4$alkoxycarbonyl or $C_1$–$C_4$alkylcarbonyl;

$R_{20}$, $R_{21}$, $R_{26}$, $R_{28}$, $R_{32}$, $R_{34}$, $R_{39}$ and $R_{40}$ are each independently of the others hydrogen or $C_1$–$C_4$alkyl;

$X_1$, $X_2$, $X_3$, $X_4$ and $X_5$ are each independently of the others oxygen or sulfur; and $n_1$, $n_2$, $n_3$, $n_4$ and $n_5$ are each independently of the others 0, 1, 2, 3 or 4;

or a salt or complex thereof with an acid, a base or a complexing agent, or a stereoisomer thereof.

2. A compound of formula I according to claim 1 wherein $R_9$ is hydrogen, $C_1$–$C_4$alkyl, $C_3$–$C_8$alkenyl, halo-$C_3$–$C_8$alkenyl, $C_3$–$C_8$alkynyl, $C_1$–$C_4$alkoxy-$C_1$–$C_8$alkyl, cyano-$C_1$–$C_4$alkyl, $C_1$–$C_8$alkoxycarbonyl-$C_1$–$C_4$alkyl, $C_3$–$C_7$cycloalkyl, $C_3$–$C_7$cycloalkyl-$C_1$–$C_4$alkyl, benzyl, —N-morpholino-, —N-thiomorpholino- or —N-piperidazino-substituted $C_1$–$C_4$alkyl, di-$C_1$–$C_4$alkylamino-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_1$–$C_4$alkoxycarbonyl or $C_1$–$C_4$alkylcarbonyl.

3. A compound of formula I according to claim 1 wherein Q is the group —C—C—.

4. A compound of formula I according to claim 1 wherein Z is oxygen.

5. A compound of formula I according to claim 1 wherein W is $W_1$.

6. A compound of formula I according to claim 1 wherein W is $W_2$.

7. A compound of formula I according to claim 5 wherein A is $X_3R_4$.

8. A compound of formula I according to claim 5 wherein A is $—COR_8$.

9. A compound of formula I according to claim 5 wherein A is $—COR_3$.

10. A compound of formula I according to claim 5 wherein A is

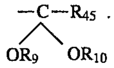.

11. A compound of formula I according to claim 5 wherein A is

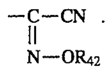.

12. A compound of formula I according to claim 5 wherein A is

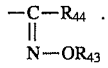.

13. A compound of formula I according to claim 5 wherein A is $—N(R_{13})—SO_2—R_{14}$.

14. A compound of formula I according to claim 6 wherein A is $—N(R_{13})—SO_2—R_{14}$.

15. A compound of formula I according to claim 7 wherein $X_3$ is sulfur and $R_4$ is $C_1$–$C_6$alkoxycarbonyl-substituted $C_1$–$C_4$alkyl.

16. A compound of formula I according to claim 5 wherein $R_1$ and $R_2$ are each halogen.

17. A compound of formula I according to claim 5 wherein $R_1$ is fluorine and $R_2$ is chlorine.

18. A compound of formula I according to claim 1 wherein R is hydrogen, $C_1$–$C_6$alkyl or $C_1$–$C_6$haloalkyl.

19. A compound of formula I according to claim 1 wherein $n_1$ is 0 or 1.

20. A compound of formula I according to claim 1 wherein R is hydrogen, methyl or trifluoromethyl.

21. 8-(4-Chloro-2-fluoro-5methoxycarbonylmethylthiophenylimino)-7-thia,1,5-diazabicyclo[3.3.0]octan-6-one according to claim 1.

22. A herbicidal and plant growth regulating composition which comprises one or more cycloalkanecarboxylic acid derivatives of formula I according to claim 1.

23. A composition according to claim 22 which comprises from 0.1% to 95% of a compound of formula I according to claim 1.

24. A method of controlling undesired plant growth, which comprises applying to the plants or to the locus thereof an effective amount of a compound of formula I according to claim 1 or of a composition according to claim 22 comprising such a compound.

25. A method according to claim 24 wherein an amount of active ingredient of from 0.001 to 4 kg per hectare is applied.

26. A method according to claim 24 of selectively controlling weeds pre- or post-emergence in crops of useful plants.

27. A method of inhibiting plant growth, which comprises applying to the plants or to the locus thereof an effective amount of a compound of formula I according to claim 1 or of a composition comprising such a compound.

* * * * *